US010590109B2

(12) United States Patent
Kong et al.

(10) Patent No.: US 10,590,109 B2
(45) Date of Patent: Mar. 17, 2020

(54) HETEROCYCLIC COMPOUNDS USED AS FGFR INHIBITORS

(71) Applicant: Nanjing InnoCare Pharma Tech Co., Ltd., Nanjing (CN)

(72) Inventors: Norman Xianglong Kong, Nanjing (CN); Chao Zhou, Nanjing (CN); Zhixiang Zheng, Nanjing (CN)

(73) Assignee: Nanjing InnoCare Pharma Tech Co., Ltd., Nanjing (CN)

( * ) Notice: Subject to any disclaimer, the term of this patent is extended or adjusted under 35 U.S.C. 154(b) by 0 days.

(21) Appl. No.: 16/246,236

(22) Filed: Jan. 11, 2019

(65) Prior Publication Data
US 2019/0144427 A1  May 16, 2019

Related U.S. Application Data

(63) Continuation-in-part of application No. PCT/CN2017/088038, filed on Jun. 13, 2017.

(30) Foreign Application Priority Data

Jul. 13, 2016 (CN) .......................... 2016 1 0550151

(51) Int. Cl.
*C07D 401/14* (2006.01)
*C07D 401/12* (2006.01)
*C07D 213/75* (2006.01)
*C07D 413/14* (2006.01)
*A61P 35/00* (2006.01)
*A61K 31/506* (2006.01)
*A61K 31/5377* (2006.01)
*A61K 31/444* (2006.01)
*A61K 31/4545* (2006.01)
*A61K 31/496* (2006.01)
*C07D 213/84* (2006.01)

(52) U.S. Cl.
CPC .......... *C07D 401/14* (2013.01); *A61K 31/444* (2013.01); *A61K 31/4545* (2013.01); *A61K 31/496* (2013.01); *A61K 31/506* (2013.01); *A61K 31/5377* (2013.01); *A61P 35/00* (2018.01); *C07D 213/75* (2013.01); *C07D 213/84* (2013.01); *C07D 401/12* (2013.01); *C07D 413/14* (2013.01)

(58) Field of Classification Search
CPC .. C07D 401/14; C07D 401/12; C07D 213/75; C07D 413/14; A61P 35/00
See application file for complete search history.

(56) References Cited

U.S. PATENT DOCUMENTS

| 7,541,373 | B2 | 6/2009 | Polisetti et al. |
| 7,989,439 | B2 | 8/2011 | Bjergarde et al. |
| 8,058,290 | B2 | 11/2011 | Bjergarde et al. |
| 8,367,715 | B2 | 2/2013 | Abecassis et al. |
| 8,410,286 | B2 | 4/2013 | Bjergarde et al. |
| 8,420,824 | B2 | 4/2013 | Bjergarde et al. |
| 2006/0183783 | A1 | 8/2006 | Polisetti et al. |
| 2008/0182844 | A1 | 7/2008 | Bjergarde et al. |
| 2009/0291984 | A1 | 11/2009 | Bjergarde et al. |
| 2011/0237641 | A1 | 9/2011 | Bjergarde et al. |
| 2011/0237801 | A1 | 9/2011 | Bjergarde et al. |
| 2012/0270918 | A1 | 10/2012 | Abecassis et al. |

FOREIGN PATENT DOCUMENTS

| CN | 1508130 A | 6/2004 |
| WO | 2006000420 A1 | 1/2006 |
| WO | 2006009741 A1 | 1/2006 |
| WO | 2007059341 A3 | 11/2007 |
| WO | 2013024427 A1 | 2/2013 |
| WO | 2015059668 A1 | 4/2015 |
| WO | 2016151499 A1 | 9/2016 |
| WO | 2016151500 A1 | 9/2016 |
| WO | WO2016/151499 A1 * | 9/2016 |

OTHER PUBLICATIONS

Gaoquan Li et al., "Synthesis and biological evaluation of 1-(2,4,5-trisubstituted phenyl)-3-(5-cyanopyrazin-2-yl) ureas as potent Chk1 kinase inhibitors", Bioorganic & Medicinal Chemistry Letters, vol. 16, No. 8, Jan. 30, 2006, pp. 2293-2298.
Kentaro Nagamatsu et al., "Reactions of 2-Triphenylphosphoimino-L-Azaazulenes with Aryl Isocyanates and Aryl Isothiocyanates", Heterocycles, vol. 67, No. 1, Dec. 31, 2006, pp. 337-351.
Jonathan Clayden et al., "N,N'-Diarylureas: A New Family of Atropisomers Exhibiting Highly Diastereoselective Reactivity", J. Org. Chem., vol. 73, No. 12, Apr. 10, 2008, pp. 4415-4423.
Ki-Hyun Kim, et al., "Conformational Switching on Platinum(II) Coordination Plane Triggered by Oxalate Anion", Bull. Korean Chem. Soc., vol. 32, No. 9, Dec. 31, 2011, pp. 3497-3500.
Tsan-Wen Lu et al., "Molecular Switch Based on Very Weak Association between BPX26C6 and Two Recognition Units", Organic Letters, vol. 15, No. 22, Oct. 30, 2013, pp. 5742-5745.
Zhao Yang, et al., "Identification of inhibitors for vascular endothelial growth factor receptor by using dynamic combinatorial chemistry", Bioorganic & Medicinal Chemistry Letters, vol. 26, No. 7, Jan. 22, 2016, pp. 1671-1674.

(Continued)

*Primary Examiner* — Timothy R Rozof
(74) *Attorney, Agent, or Firm* — Perkins Coie LLP; Viola T. Kung

(57) ABSTRACT

The present invention relates to a heterocyclic compound, a pharmaceutical composition containing the same, a preparation method thereof, and use thereof as a fibroblast growth factor receptor (FGFR) inhibitor. The compound is a heterocyclic compound as shown in Formula I, or a pharmaceutically acceptable salt, prodrug, solvent compound, polymorph, isomer or stable isotopic derivative thereof. The present invention further relates to use of the compound for the treatment or prevention of related diseases which are FGFR-mediated such as cancer, and a method for applying the compound to treat said diseases.

8 Claims, 1 Drawing Sheet

(56) References Cited

OTHER PUBLICATIONS

Ying An, et al., "Design and synthesis of novel benzoxazole analogs as Aurora B kinase inhibitors", Bioorganic & Medicinal Chemistry Letters, vol. 26, No. 13, May 7, 2016, pp. 3067-3072.
International Search Report dated Jul. 28, 2017 issued in PCT/CN2017/088038.
Aziz Ouach, et al., "Novel optimization of valmerins (tetrahydropyrido[1,2-α]isoindolones) as potent dual CDK5/GSK3 inhibitors", European Journal of Medicinal Chemistry, vol. 115, Mar. 2, 2016, pp. 311-325.
Supplementary European Search Report dated Nov. 28, 2019 cited in EP 17826852.

* cited by examiner

HETEROCYCLIC COMPOUNDS USED AS FGFR INHIBITORS

This application is a continuation-in-part of PCT/CN2017/088038, filed Jun. 13, 2017, which claims priority to CN201610550151.3, filed Jul. 13, 2016. The above applications are incorporated herein by reference in their entirety.

TECHNICAL FIELD

The present invention relates to a heterocyclic compound, a preparation method of a pharmaceutical composition containing the same, and use thereof as a fibroblast growth factor receptor (FGFR) inhibitor. The compound according to the present invention can be used to treat or prevent related diseases mediated by FGFR, such as cancer.

BACKGROUND ART

Fibroblast growth factors (FGFs) belong to a polypeptide family coded by the FGF gene family, and having different biological activity and having relevant structures. So far the FGF family has been found to have 22 members. Fibroblast growth factor receptors (FGFRs) are a class of trans-membrane tyrosine kinase receptors, which mediate FGF signal transmission to the cytoplasm. Currently 4 FGFRs of independent gene codes have been confirmed, i.e., FGFR1, FGFR2, FGFR3, and FGFR4. They are all single chain glucoprotein molecules comprised of an extracellular region, a trans-membrane region and an intracellular region. The receptor-ligand interaction causes receptor dimerization and autophosphorylation, and the formation of a complex with a membrane binding protein and a cytoplasmic helper protein, thereby mediating conduction of multiple signals. The FGFR-FGF signal conducting system plays an important role in a great many biological processes such as cell proliferation, differentiation, migration, angiogenesis and tissue repair.

FGFR4 is a main FGF receptor subtype in the liver. 10 out of more than 20 fibroblast growth factors (FGFs) that have been discovered up to now can bind to FGFR4, where only FGF19 binds to FGFR4 specifically. Studies in recent years show that changes, such as overexpression, mutation, translocation and truncation, of FGFR4 are associated with the progress in various human cancer, including rhabdomyosarcoma, renal cell carcinoma, myeloma, breast cancer, gastric cancer, colon cancer, bladder cancer, pancreas cancer and hepatocellular cancer.

Therefore, it can be predicted that the selective inhibition of FGFR4 can be used to treat the above cancer, and particularly tumors where an activated mutant of the receptor tyrosine kinase is present or the receptor tyrosine kinase is upregulated are especially sensitive to this type of inhibitors.

DESCRIPTION OF THE INVENTION

Figure 1:
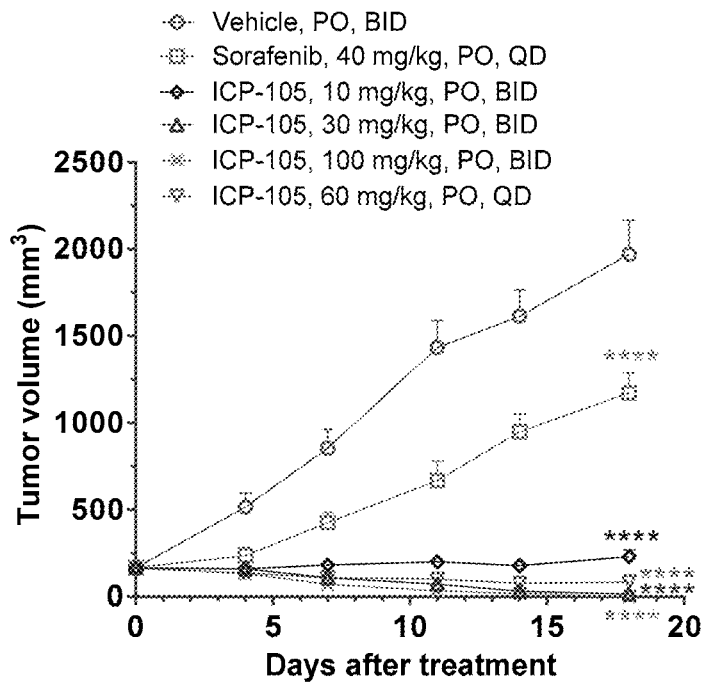
FIG. 1 shows the efficacy of compound 18 in FGF19/FGFR4-overexpressed Hep3B HCC xenograft model. Tumor growth curves after administering Sorafenib and compound 18 to female BALB/c nude mice Hep3B HCC xenograft established tumors. Data points represent group mean, error bars represent standard error of the mean (SEM). *P<0.05, P<0.01, *P<0.001, ****P<0.0001, NS P>0.05 vs vehicle group.

An object of the present invention is to provide a compound as shown in Formula I, an isomer, a prodrug, a stable isotopic derivative or a pharmaceutically acceptable salt thereof

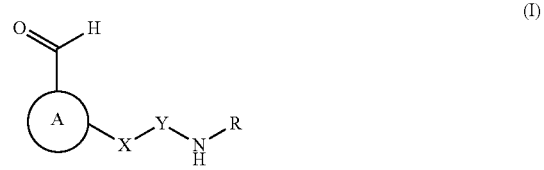

(I)

where rings A and R are each independently selected from the group consisting of substituted or unsubstituted aryl and heteroaryl groups, and when substituted, A or R may be substituted with one or more substituents, and the substituent is independently selected from the group consisting of hydrogen, halogen, cyano, C1-C8 alkyl, C3-C8 cyclyl, 3-8 membered heterocyclyl, aryl, heteroaryl, formyl, —C(O)R$^1$, carboxyl, alkenyl, alkynyl, —OR$^1$, and —NR$^2$R$^3$, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR$^4$, —OC(O)NR$^5$R$^6$, —C(O)OR$^4$, —C(O)NR$^5$R$^6$, —C(O)R$^4$, —NR$^5$R$^6$, —NR$^5$C(O)R$^4$, —NR$^4$C(O)NR$^5$R$^6$, —S(O)mR$^4$, —NR$^5$S(O)mR$^4$, —SR$^4$, —NR$^4$S(O)mNR$^5$R$^6$, and —S(O)mNR$^5$R$^6$;

X is selected from the group consisting of CR$^7$R$^8$, NR$^7$, O, and S;

Y is selected from the group consisting of —C(O)—, —C(=NR$^9$)—, and —S(O)m-;

R$^1$, R$^2$, R$^3$, R$^4$, R$^5$, and R$^6$ are each independently selected from the group consisting of hydrogen, C1-C8 alkyl, C3-C8 cyclyl, 3-8 membered monocyclic heterocyclyl, monocyclic heteroaryl or monocyclic aryl, alkenyl, and alkynyl, where said R$^2$ and R$^3$, or R$^5$ and R$^6$ may form a 3-7 membered heterocyclyl group together with the N atom to which they are attached; and said R$^7$ and R$^8$ may form a 3-8 membered cyclyl or a 3-8 membered monocyclic heterocyclyl together with the C atom to which they are attached;

R$^7$ and R$^8$ are each independently selected from the group consisting of hydrogen, halogen, cyano, C1-C8 alkyl, C3-C8 cyclyl, 3-8 membered heterocyclyl, aryl, heteroaryl, formyl, —C(O)R$^1$, carboxyl, alkenyl, alkynyl, —OR$^1$, and —NR$^2$R$^3$, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR$^4$, —OC(O)NR$^5$R$^6$, —C(O)OR$^4$, —C(O)NR$^5$R$^6$, —C(O)R$^4$, —NR$^5$R$^6$, —NR$^5$C(O)R$^4$, —NR$^4$C(O)NR$^5$R$^6$, —S(O)mR$^4$, —NR$^5$S(O)mR$^4$, —SR$^4$, —NR$^4$S(O)mNR$^5$R$^6$, and —S(O)mNR$^5$R$^6$;

R$^9$ is independently selected from the group consisting of hydrogen, C1-C8 alkyl, C3-C8 cyclyl, 3-8 membered heterocyclyl, aryl, heteroaryl, formyl, C(O)R¹, alkenyl, and alkynyl, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR⁴, —OC(O)NR⁵R⁶, —C(O)OR⁴, —C(O)NR⁵R⁶, —C(O)R⁴, —NR⁵R⁶, —NR⁵C(O)R⁴, —NR⁴C(O)NR⁵R⁶, —S(O)mR⁴, —NR⁵S(O)mR⁴, —SR⁴, —NR⁴S(O)mNR⁵R⁶, —S(O)mNR⁵R⁶; and m is 1 or 2.

In one embodiment of the present invention, a compound as shown in General formula (I), an isomer, a prodrug, or a pharmaceutically acceptable salt thereof is provided, where the compound as shown in Formula I is shown in Formula II:

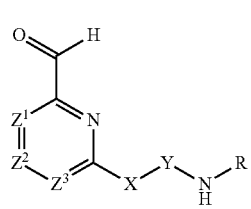

(II)

Z¹, Z², and Z³ are each independently selected from the group consisting of CR^{Z1}, CR^{Z2}, CR^{Z3} or N, and
when Z¹ is N, Z² and Z³ are not N at the same time;
when Z² is N, Z¹ and Z³ are not N at the same time;
when Z³ is N, Z¹ and Z² are not N at the same time;
R^{Z1}, R^{Z2}, and R^{Z3} are each independently selected from the group consisting of hydrogen, halogen, cyano, C1-C8 alkyl, C3-C8 cyclyl, 3-8 membered heterocyclyl, aryl, heteroaryl, formyl, —C(O)R¹, carboxyl, alkenyl, alkynyl, —OR¹, and —NR²R³, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR⁴, —OC(O)NR⁵R⁶, —C(O)OR⁴, —C(O)NR⁵R⁶, —C(O)R⁴, —NR⁵R⁶, —NR⁵C(O)R⁴, —NR⁴C(O)NR⁵R⁶, —S(O)mR⁴, —NR⁵S(O)mR⁴, —SR⁴, —NR⁴S(O)mNR⁵R⁶, and —S(O)mNR⁵R⁶;

X is selected from the group consisting of CR⁷R⁸, NR⁷, O, and S;

Y is selected from the group consisting of —C(O)—, —C(=NR⁹)—, and —S(O)m-;

R¹, R², R³, R⁴, R⁵, and R⁶ are each independently selected from the group consisting of hydrogen, C1-C8 alkyl, C3-C8 cyclyl, 3-8 membered monocyclic heterocyclyl, monocyclic heteroaryl or monocyclic aryl, alkenyl, and alkynyl, where said R² and R³, or R⁵ and R⁶ may form a 3-7 membered heterocyclyl group together with the N atom to which they are attached; and said R⁷ and R⁸ may form a 3-8 membered cyclyl or a 3-8 membered monocyclic heterocyclyl group together with the C atom to which they are attached;

R⁷ and R⁸ are each independently selected from the group consisting of hydrogen, halogen, cyano, C1-C8 alkyl, C3-C8 cyclyl, 3-8 membered heterocyclyl, aryl, heteroaryl, formyl, —C(O)R¹, carboxyl, alkenyl, alkynyl, —OR¹, and —NR²R³, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR⁴, —OC(O)NR⁵R⁶, —C(O)OR⁴, —C(O)NR⁵R⁶, —C(O)R⁴, —NR⁵R⁶, —NR⁵C(O)R⁴, —NR⁴C(O)NR⁵R⁶, —S(O)mR⁴, —NR⁵S(O)mR⁴, —SR⁴, —NR⁴S(O)mNR⁵R⁶, and —S(O)mNR⁵R⁶;

R⁹ is independently selected from the group consisting of hydrogen, C1-C8 alkyl, C3-C8 cyclyl, 3-8 membered heterocyclyl, aryl, heteroaryl, formyl, C(O)R¹, alkenyl, and alkynyl, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR⁴, —OC(O)NR⁵R⁶, —C(O)OR⁴, —C(O)NR⁵R⁶, —C(O)R⁴, —NR⁵R⁶, —NR⁵C(O)R⁴, —NR⁴C(O)NR⁵R⁶, —S(O)mR⁴, —NR⁵S(O)mR⁴, —SR⁴, —NR⁴S(O)mNR⁵R⁶, and —S(O)mNR⁵R⁶; and when Z¹ is CCH₂OH, CCH₂COOH, or C-(4-piperidine), compounds (2-1), (2-2), and (2-3) may be present in the forms of isomers (2-1A), (2-2A), and (2-3A):

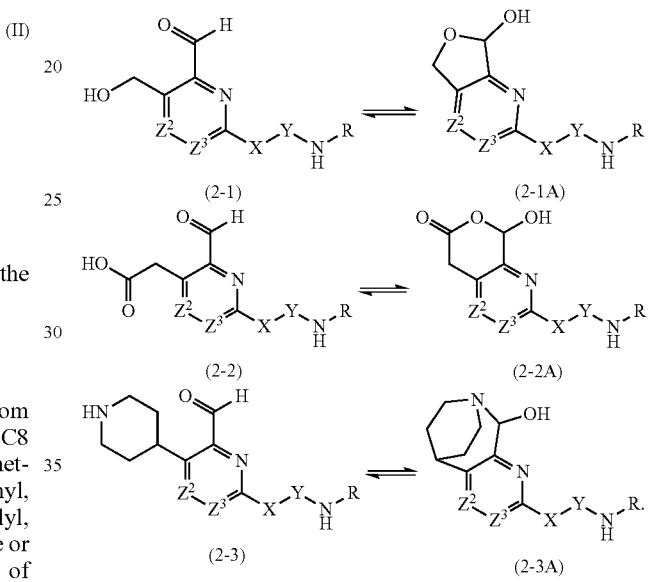

In another embodiment of the present invention, a compound as shown in General formula (I), an isomer, a prodrug, a stable isotopic derivative thereof or a pharmaceutically acceptable salt thereof is provided, where the compound as shown in Formula I is Formula IIIa, IIIb, IIIc, IIId, IIIe, or IIIf:

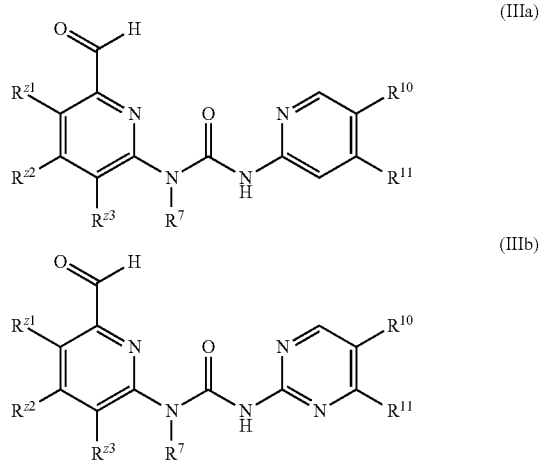

-continued

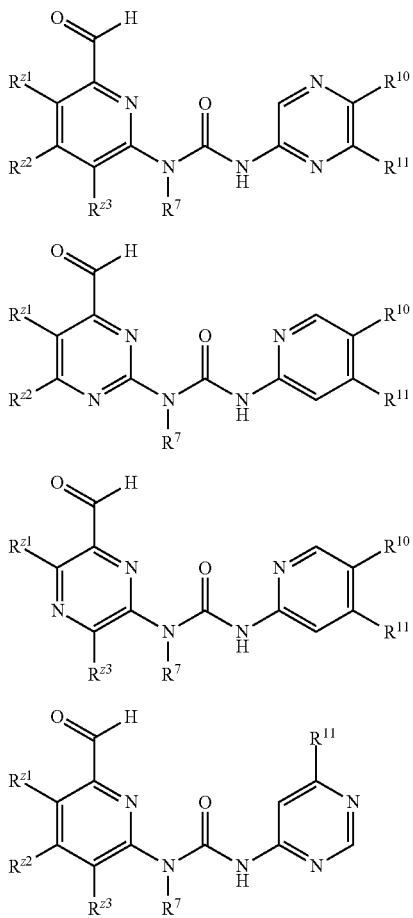

(IIIc)

(IIId)

(IIIe)

(IIIf)

$R^{Z2}$, $R^{Z3}$, $R^{10}$, and $R^{11}$ are each independently selected from the group consisting of hydrogen, halogen, cyano, C1-C8 alkyl, C3-C8 cyclyl, 3-8 membered heterocyclyl, aryl, heteroaryl, formyl, —C(O)R$^1$, carboxyl, alkenyl, alkynyl, —OR$^1$, and —NR$^2$R$^3$, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR$^4$, —OC(O)NR$^5$R$^6$, —C(O)OR$^4$, —C(O)NR$^5$R$^6$, —C(O)R$^4$, —NR$^5$R$^6$, —NR$^8$C(O)R$^4$, —NR$^4$C(O)NR$^5$R$^6$, —S(O)mR$^4$, —NR$^8$S(O)mR$^4$, —SR$^4$, —NR$^4$S(O)mNR$^5$R$^6$, and —S(O)mNR$^5$R$^6$, R$^7$ is independently selected from the group consisting of H, C1-C8 alkyl, C3-C8 cyclyl, 3-8 membered monocyclic heterocyclyl, monocyclic heteroaryl or monocyclic aryl, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR$^4$, —OC(O)NR$^5$R$^6$, —C(O)OR$^4$, —C(O)NR$^5$R$^6$, —C(O)R$^4$, —NR$^5$R$^6$, —NR$^5$C(O)R$^4$, —NR$^4$C(O)NR$^5$R$^6$, —S(O)mR$^4$, —NR$^5$S(O)mR$^4$, —SR$^4$, —NR$^4$S(O)mNR$^5$R$^6$, and —S(O)mNR$^5$R$^6$, R$^1$, R$^2$, R$^3$, R$^4$, R$^5$, and R$^6$ are each independently selected from the group consisting of hydrogen, C1-C8 alkyl, C3-C8 cyclyl, 3-8 membered monocyclic heterocyclyl, monocyclic heteroaryl or monocyclic aryl, alkenyl, and alkynyl, where said R$^2$ and R$^3$, or R$^5$ and R$^6$ may form a 3-7 membered heterocyclyl group together with the N atom to which they are attached; and said R$^7$ and R$^8$ may form a 3-8 membered cyclyl or a 3-8 membered monocyclic heterocyclyl group together with the C atom to which they are attached; and said R$^2$ and R$^3$, or R$^5$ and R$^6$ can form a 3-8 membered heterocyclyl group together with the N atom to which they are attached.

In a further embodiment of the present invention, a compound as shown in General formula (I), an isomer, a prodrug, a stable isotopic derivative thereof or a pharmaceutically acceptable salt thereof is provided, where the compound as shown in Formula I is Formula IV:

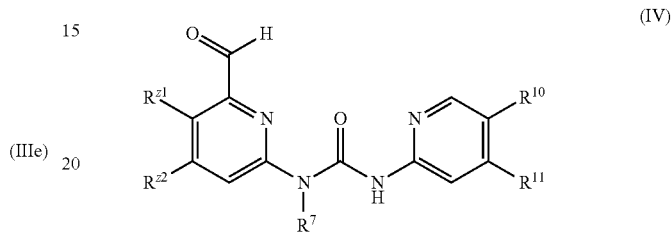

(IV)

$R^{Z1}$ and $R^{Z2}$ are each independently selected from the group consisting of hydrogen, halogen, C1-C4 alkyl, C3-C7 cyclyl, 4-6 membered monocyclic heterocyclyl, 5-6 membered monocyclic heteroaryl or monocyclic aryl, formyl, keto, carboxyl, cyano, OR$^1$, and NR$^2$R$^3$, where the alkyl, cyclyl, heterocyclyl, aryl or heteroaryl group is optionally substituted with one or more substituents selected from the group consisting of halogen, hydroxy, C1-C4 alkyl, C3-C7 cyclyl, 4-6 membered heterocyclyl, aryl or heteroaryl;

R$^7$ is selected from the group consisting of H, C1-C8 alkyl, C3-C8 cyclyl, 3-8 membered monocyclic heterocyclyl, monocyclic heteroaryl or monocyclic aryl, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, —OR$^4$, —OC(O)NR$^5$R$^6$, —C(O)OR$^4$, —C(O)NR$^5$R$^6$, —C(O)R$^4$, —NR$^5$R$^6$, —NR$^5$C(O)R$^4$, —NR$^4$C(O)NR$^5$R$^6$, —S(O)mR$^4$, —NR$^5$S(O)mR$^4$, —SR$^4$, —NR$^4$S(O)mNR$^5$R$^6$, and —S(O)mNR$^5$R$^6$;

R$^{10}$ is independently selected from the group consisting of hydrogen, halogen, halo C1-C4 alkyl and cyano;

R$^{11}$ is independently selected from the group consisting of hydrogen, halogen, C1-C4 alkyl, halo C1-C4 alkoxy, C1-C6 alkoxy, HO—C1-C4 alkoxy, cyano, NR$^2$R$^3$, C1-C4 alkoxy C1-C4 alkoxy, and C1-C4 alkoxy halo C1-C4 alkoxy;

R$^1$, R$^2$ and R$^3$ are each independently selected from the group consisting of hydrogen, C1-C8 alkyl, C3-C8 cyclyl, 3-8 membered monocyclic heterocyclyl, monocyclic heteroaryl or monocyclic aryl, C1-C3 alkylthiol, and haloalkoxy substituted with hydroxy at any position; and R$^4$, R$^5$, and R$^6$ are each independently selected from the group consisting of hydrogen, C1-C8 alkyl, C3-C8 cyclyl, 3-8 membered monocyclic heterocyclyl, monocyclic heteroaryl or monocyclic aryl, alkenyl, and alkynyl, where said R$^2$ and R$^3$, or R$^5$ and R$^6$ may form a 3-7 membered heterocyclyl group together with the N atom to which they are attached; and said R$^7$ and R$^8$ may form a 3-8 membered cyclic group or a 3-8 membered monocyclic heterocyclic group together with the C atom to which they are attached.

In an additional embodiment of the present invention, a compound as shown in General formula (I), an isomer, a prodrug, a stable isotopic derivative thereof or a pharmaceutically acceptable salt thereof is provided, where the compound as shown in Formula I is Formula V:

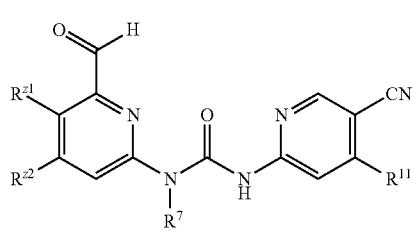

(V)

$R^{Z1}$ and $R^{Z2}$ are each independently selected from the group consisting of hydrogen, halogen, C1-C4 alkyl, C3-C7 cyclyl, 5-6 membered monocyclic heterocyclyl, 5-6 membered monocyclic heteroaryl or monocyclic aryl, formyl, and carboxyl, where the alkyl, cyclyl, heterocyclyl, aryl or heteroaryl group is optionally substituted with one or more substituents selected from the group consisting of halogen, hydroxy, C1-C4 alkyl, 5-6 membered heterocyclyl, aryl or heteroaryl;

$R^7$ is selected from the group consisting of hydrogen, C1-C4 alkyl, and C3-6 cyclyl, where the alkyl or cyclyl group is optionally substituted with one or more substituents selected from the group consisting of C1-C3 alkyl, and 4-6 membered monocyclic heterocyclyl;

$R^{11}$ is selected from the group consisting of $NR^2R^3$, C1-C3 alkoxy, and $—O(CH_2)_{0-1}—R^4$, where, $R^4$ is independently selected from the group consisting of hydrogen, HO—C1-C8 alkyl, C3-C8 cyclyl, 3-8 membered monocyclic heterocyclyl, monocyclic heteroaryl or monocyclic aryl, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, $—OR^5$, $—OC(O)NR^5R^6$, $—C(O)OR^5$, $—C(O)NR^5R^6$, $—C(O)R^5$, $—NR^5R^6$, $—NR^5C(O)R^6$, $—NR^7C(O)NR^5R^6$, $—S(O)mR^5$, $—NR^5S(O)mR^6$, $—SR^5$, $—NR^7S(O)mNR^5R^6$, and $—S(O)mNR^5R^6$; $R^2$ and $R^3$ are independently selected from the group consisting of hydrogen, C1-C8 alkyl, C3-C8 cyclyl, 3-8 membered monocyclic heterocyclyl, monocyclic heteroaryl or monocyclic aryl, C1-C3 alkylthiol and haloalkoxy substituted with hydroxy at any position, where the alkyl, cyclyl, heterocyclyl, aryl or heteroaryl group is optionally substituted with one or more substituents selected from the group consisting of halogen, cyano, C1-C8 alkyl, C3-C8 cyclyl, 3-8 membered heterocyclyl, $—OR^5$, $—OC(O)NR^5R^6$, $—C(O)OR^5$, $—C(O)NR^5R^6$, $—C(O)R^5$, $—NR^5R^6$, $—NR^5C(O)R^6$, $—NR^7C(O)NR^5R^6$, $—S(O)mR^6$, $—NR^5S(O)mR^6$, $—SR^5$, $—NR^7S(O)mNR^5R^6$, and $—S(O)mNR^5R^6$; and $R^4$, $R^5$, and $R^6$ are each independently selected from the group consisting of hydrogen, C1-C8 alkyl, C3-C8 cyclyl, 3-8 membered monocyclic heterocyclyl, monocyclic heteroaryl or monocyclic aryl, alkenyl, and alkynyl, where said $R^2$ and $R^3$, or $R^5$ and $R^6$ may form a 3-7 membered heterocyclyl group together with the N atom to which they are attached; and said $R^7$ and $R^8$ may form a 3-8 membered cyclic group or a 3-8 membered monocyclic heterocyclic group together with the C atom to which they are attached.

In one embodiment, the compound has a general Formula V:

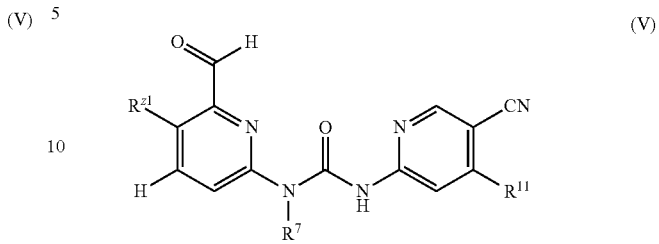

(V)

wherein $R^{21}$ is selected from the group consisting of hydrogen, halogen, and C1-C4 alkyl optionally substituted with halogen or hydroxyl, or $R^{Z1}$ is

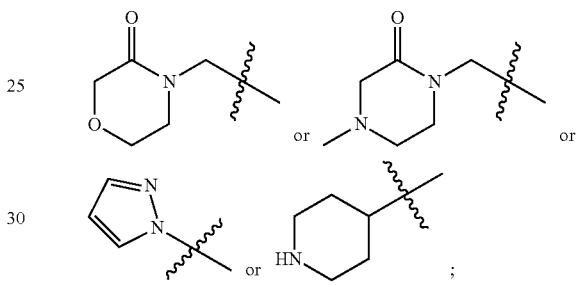

$R^7$ is hydrogen or C1-C4 alkyl;

$R^{11}$ is selected from the group consisting of $NR^2R^3$, halogen, and $—O—(C1-C8\ alkylene)-OR^a$;

$R^2$, and $R^3$ are independently C1-C8 alkyl, wherein the alkyl is optional substituted by $—OR^b$; and $R^a$ and $R^b$ are independently H or C1-C8 alkyl.

In a preferred embodiment of Formula V, $R^{z1}$ is

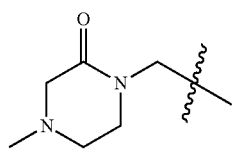 [SMILES: *CN1CCN(C)CC1=O]

and $R^{11}$ is $—O—(C1-C8\ alkylene)-OR^a$.

In another embodiment, the compound has Formula V':

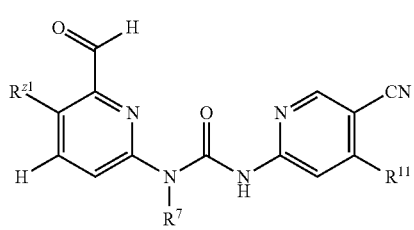

V' wherein $R^{Z1}$ is

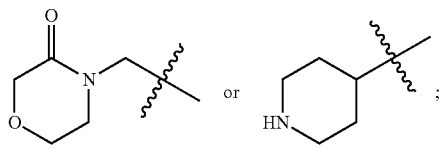 [SMILES: *CN1CCOCC1=O ; *C1CCNCC1]

$R^7$ is hydrogen or C1-C4 alkyl;
$R^{11}$ is selected from the group consisting of $NR^2R^3$, halogen, C1-C3 alkoxy, and $OR^4$;
$R^2$, $R^3$ and $R^4$ are independently H and C1-C8 alkyl, wherein the alkyl is optional substituted by $-OR^5$, and
$R^5$ is H or C1-C8 alkyl.

Typical compounds according to the present invention include, but are not limited to:

1

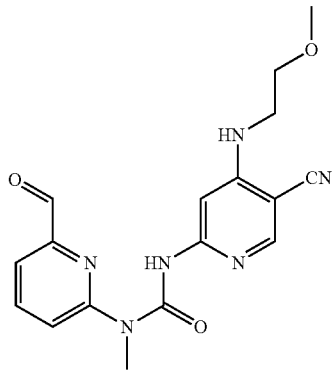

3-(5-cyano-4-((2-methoxyethyl)amino)
pyrid-2-yl)-1-(6-formylpyrid-2-yl)-
1-methylurea

2

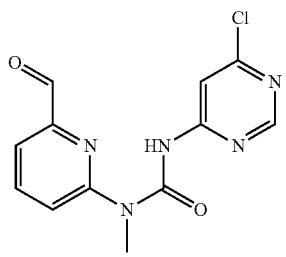

3-(6-chloropyrimidin-4-yl)-1-
(6-formylpyrid-2-yl)-1-methylurea

3

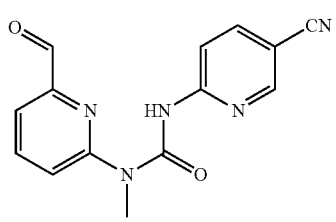

3-(5-cyanopyrid-2-yl)-1-(6-formylpyrid-
2-yl)-1-methylurea

4

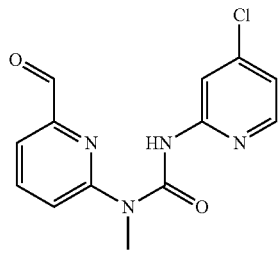

3-(4-chloro-5-cyanopyrid-2-yl)-1-
(6-formylpyrid-2-yl)-1-methylurea

5

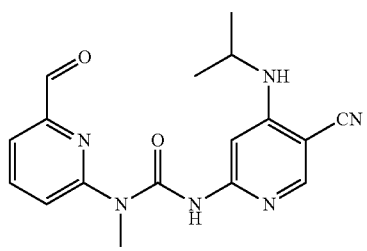

3-(5-cyano-4-(isopropylamino)pyrid-2-yl)-
1-(6-formylpyrid-2-yl)-1-methylurea

6

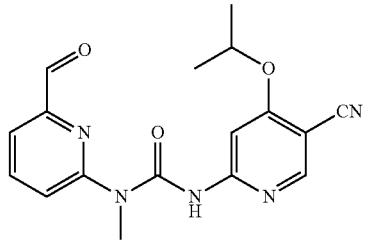

3-(5-cyano-4-isopropoxypyrid-2-yl)-1-
(6-formylpyrid-2-yl)-1-methylurea

7

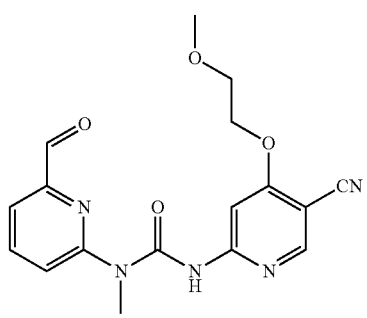

3-(5-cyano-4-(2-methoxyethoxy) pyrid-2-yl)-
1-(6-formylpyrid-2-yl)-1-methylurea

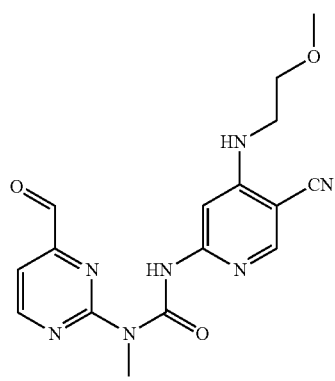

3-(5-cyano-4-((2-methoxyethyl)amino)pyrid-2-yl)-1-(4-formylpyrimidin-2-yl)-1-methylurea

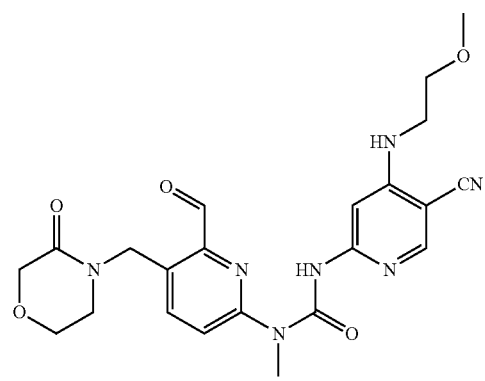

3-(5-cyano-4-((2-methoxyethyl)amino)pyrid-2-yl)-1-(6-formyl-5-((3-carbonylmorpholino)methyl) pyrid-2-yl)-1-methylurea

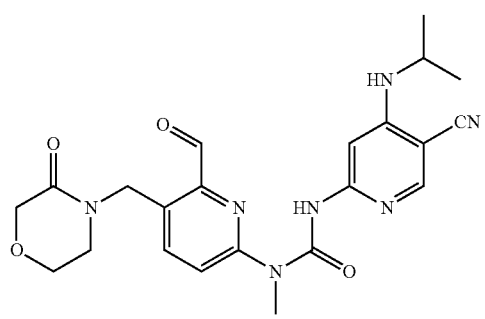

3-(5-cyano-4-(isopropylamino)pyrid-2-yl)-1-(6-formyl-5-((3-carbonylmorpholino)methyl) pyrid-2-yl)-1-methylurea

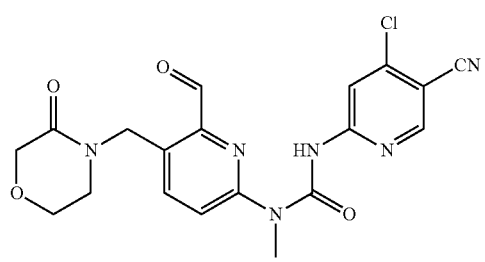

1-(4-chloro-5-cyanopyrid-2-yl)-3-(6-formyl-5-((3-carbonylmorpholine)methyl)pyrid-2-yl)urea

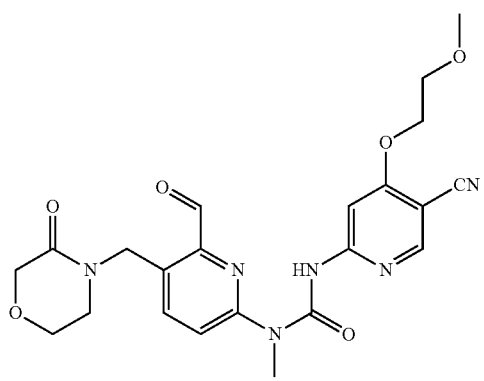

3-(5-cyano-4-(2-methoxyethoxy) pyrid-2-yl)-1-(6-formyl-5-((3-carbonylmorpholino)methyl pyrid-2-yl)-1-methylurea

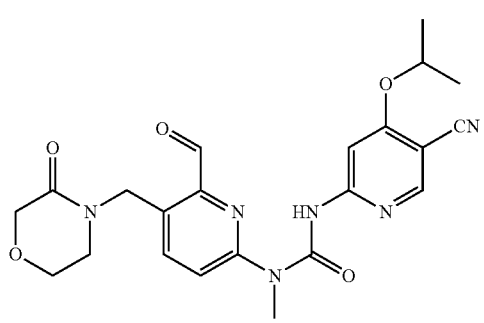

1-(5-cyano-4-isopropoxypyrid-2-yl)-3-(6-formyl-5-((3-carbonylmorpholine) methyl)pyrid-2-yl)urea

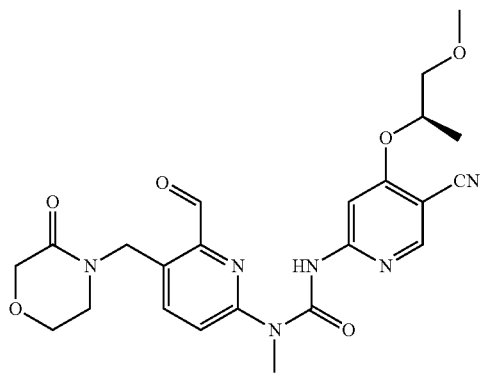

(R)-3-(5-cyano-4-((1-methoxyprop-2-yl)oxo)pyrid-2-yl)-1-(6-formyl-5-((3-carbonylmorpholino)methyl) pyrid-2-yl)-1-methylurea

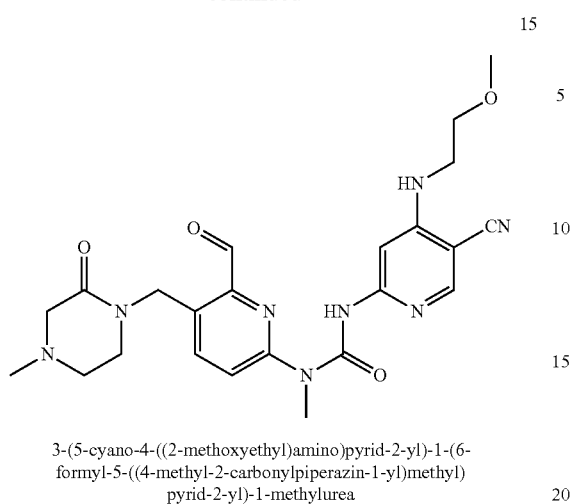

3-(5-cyano-4-((2-methoxyethyl)amino)pyrid-2-yl)-1-(6-formyl-5-((4-methyl-2-carbonylpiperazin-1-yl)methyl)pyrid-2-yl)-1-methylurea

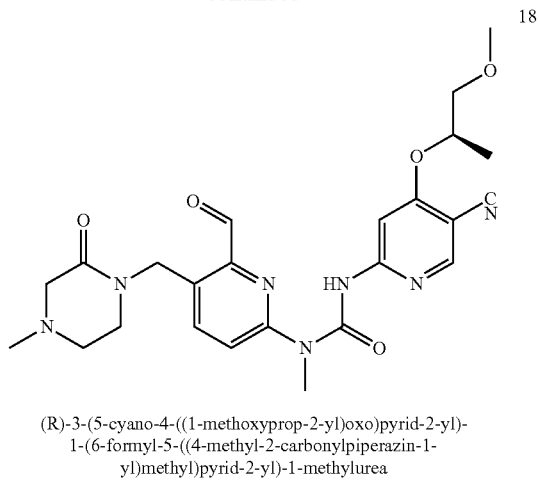

(R)-3-(5-cyano-4-((1-methoxyprop-2-yl)oxo)pyrid-2-yl)-1-(6-formyl-5-((4-methyl-2-carbonylpiperazin-1-yl)methyl)pyrid-2-yl)-1-methylurea

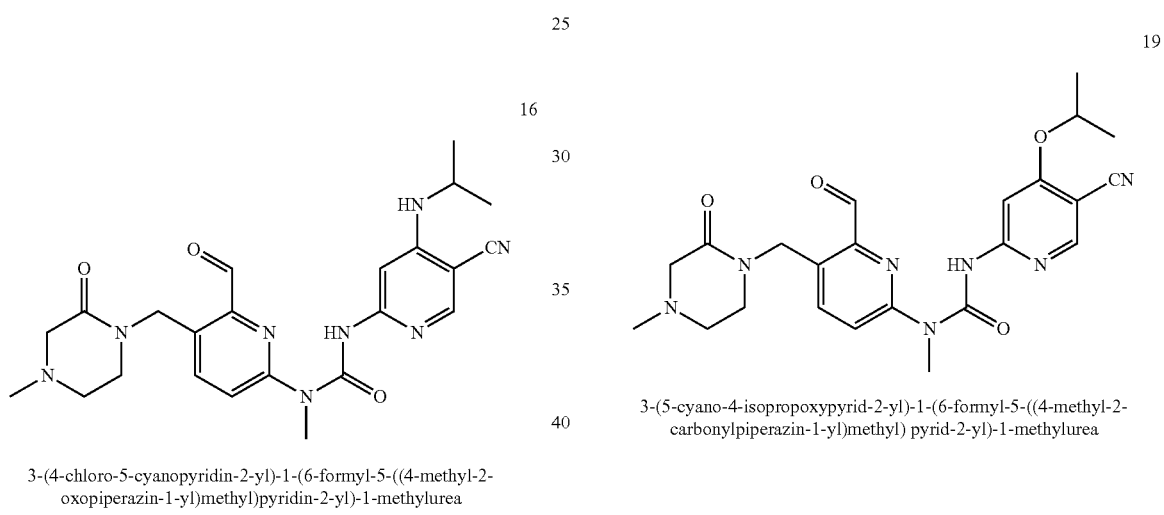

3-(4-chloro-5-cyanopyridin-2-yl)-1-(6-formyl-5-((4-methyl-2-oxopiperazin-1-yl)methyl)pyridin-2-yl)-1-methylurea 3-(5-cyano-4-isopropoxypyrid-2-yl)-1-(6-formyl-5-((4-methyl-2-carbonylpiperazin-1-yl)methyl) pyrid-2-yl)-1-methylurea

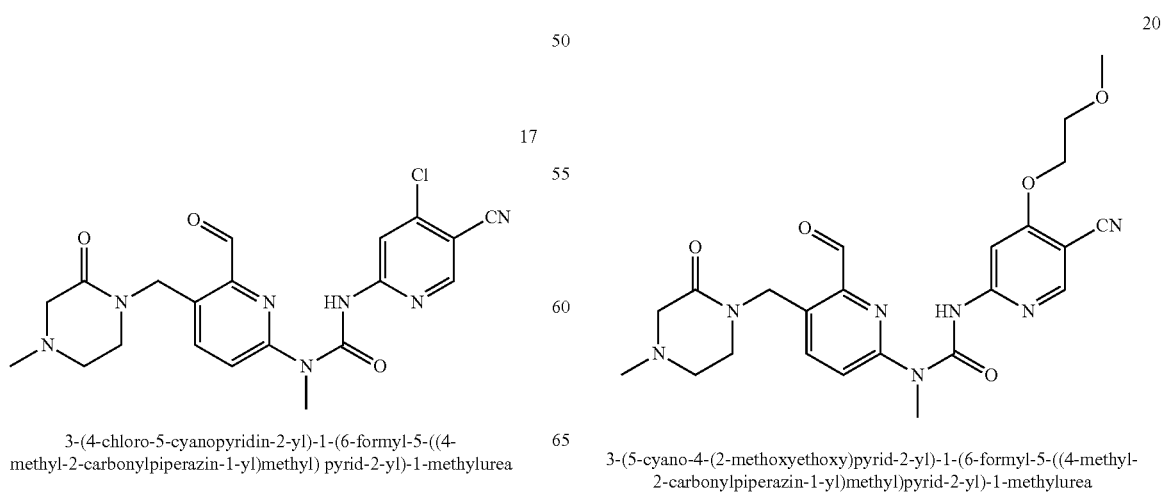

3-(4-chloro-5-cyanopyridin-2-yl)-1-(6-formyl-5-((4-methyl-2-carbonylpiperazin-1-yl)methyl) pyrid-2-yl)-1-methylurea 3-(5-cyano-4-(2-methoxyethoxy)pyrid-2-yl)-1-(6-formyl-5-((4-methyl-2-carbonylpiperazin-1-yl)methyl)pyrid-2-yl)-1-methylurea

21

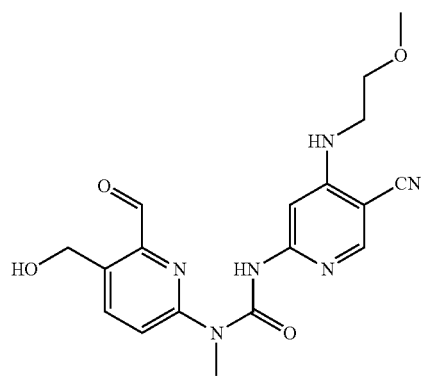

3-(5-cyano-4-((2-methoxyethyl)amino) pyrid-2-yl)-1-(6-formyl-5-(hydroxymethyl)pyrid-2-yl)-1-methylurea

22

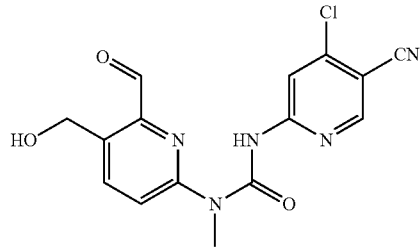

3-(4-chloro-5-cyanopyrid-2-yl)-1-(6-formyl-5-(hydroxymethyl)pyrid-2-yl)-1-methylurea

23

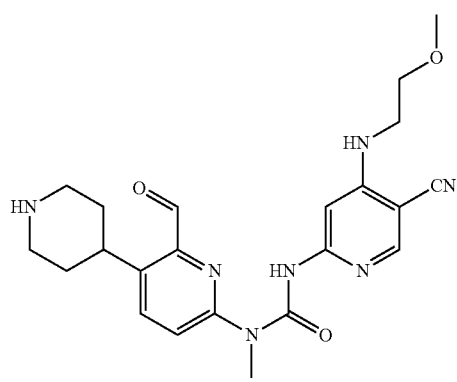

3-(5-cyano-4-((2-methoxyethyl)amino) pyrid-2-yl)-1-(6-formyl-5-(piperidin-4-yl)pyrid-2-yl)-1-methylurea

24

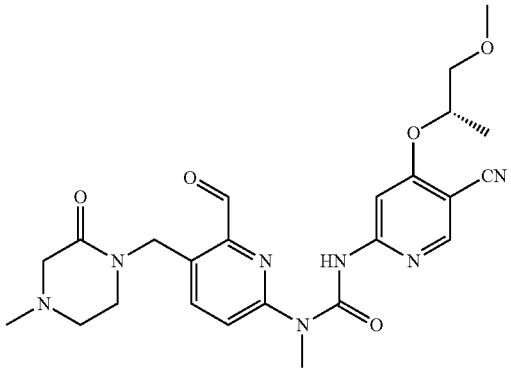

(S)-3-(5-cyano-4-((1-methoxyprop-2-yl)oxy)pyrid-2-yl)-1-(6-formyl-5-((4-methyl-2-carbonylpiperazin-1-yl)methyl) pyrid-2-yl)-1-methylurea

25

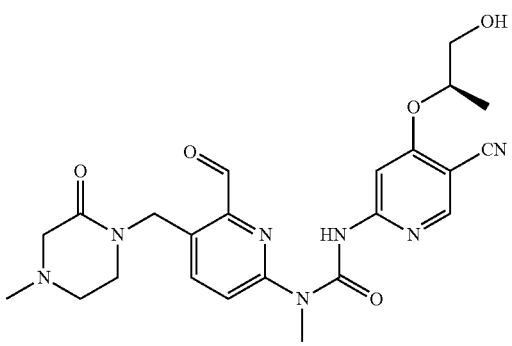

(R)-3-(5-cyano-4-((1-hydroxyprop-2-yl)oxy)pyrid-2-yl)-1-(6-formyl-5-((4-methyl-2-carbonylpiperazin-1-yl)methyl) pyrid-2-yl)-1-methylurea

26

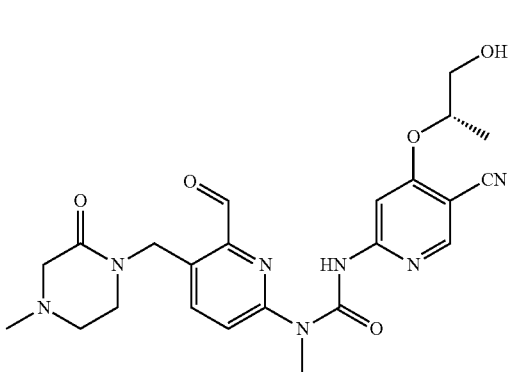

(S)-3-(5-cyano-4-((1-hydroxyprop-2-yl)oxy)pyrid-2-yl)-1-(6-formyl-5-((4-methyl-2-carbonylpiperazin-1-yl)methyl) pyrid-2-yl)-1-methylurea

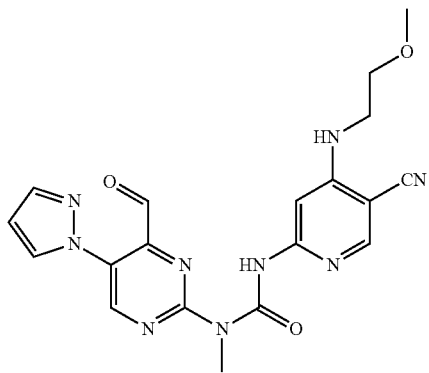

3-(5-cyano-4-((2-methoxyethyl) amino)pyrid-2-yl)-
1-(6-formyl-5-((1H-pyrazol-1-yl)pyrazol-2-
yl)-1-methylurea

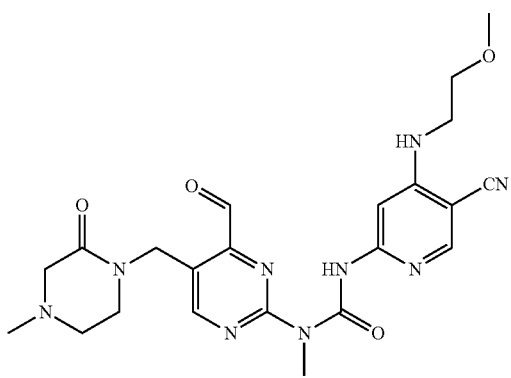

3-(5-cyano-4-((2-methoxyethyl) amino)pyrid-2-yl)-
1-(4-formyl-5-((4-methyl-2-carbonyl-piperazin-1-yl)methyl)
pyrimidin-2-yl)-1-methylurea

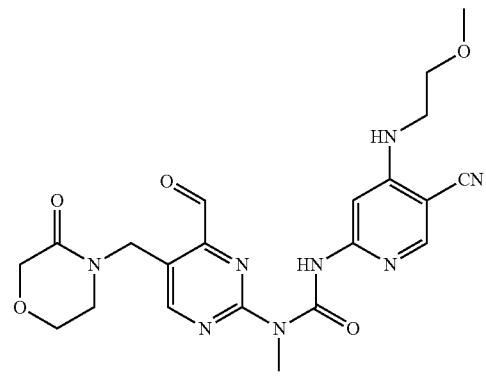

3-(5-cyano-4-((2-methoxyethyl) amino)pyrid-2-yl)-
1-(4-formyl-5-((3-carbonylmorpholino)methyl) pyrimidin-2-yl)-
1-methylurea or tautomers, mesomers, racemates, enantiomers, diastereoisomers thereof, mixtures thereof and pharmaceutically acceptable salts thereof.

The compound according to the present invention is an effective inhibitor of FGFR, and particularly an effective selective inhibitor of FGFR4. Therefore, the compound according to the present invention can be used to treat or prevent FGFR mediated diseases, particularly FGFR4 mediated diseases, including but not limited to cancer and inflammatory diseases. The compound according to the present invention can be used to treat or prevent cancer, such as rhabdomyosarcoma, renal cell carcinoma, myeloma, breast cancer, gastric cancer, colon cancer, bladder cancer, pancreas cancer and hepatocellular cancer. The compound according to the present invention can especially treat or prevent liver cancer, and particularly hepatocellular cancer. Tumors where an activated mutant of the receptor tyrosine kinase is present or the receptor tyrosine kinase is unregulated are especially sensitive to this type of inhibitors.

As a selective inhibitor of FGFR4, the compound according to the present invention has lower side effects.

The present invention further relates to a pharmaceutical composition, comprising the compound as shown in General formula (I) or an isomer, a prodrug, a stable isotopic derivative thereof or a pharmaceutically acceptable salt and a pharmaceutically acceptable carrier, diluent and excipient thereof.

The present invention further includes a method for preparing the pharmaceutical composition, including for example mixing the compound according to the present invention together with a pharmaceutically acceptable carrier, diluent, and excipient. The pharmaceutical composition according to the present invention can be prepared by a conventional method in the art.

Another aspect of the present invention relates to use of a compound as shown in General formula (I) or an isomer, a prodrug, a stable isotopic derivative or a pharmaceutically acceptable salt thereof, and a pharmaceutically acceptable carrier, diluent and excipient thereof in the preparation of a drug for treating or preventing FGFR and particularly FGFR4 mediated diseases, for example tumors or inflammatory diseases.

Another aspect of the present invention relates to use of a compound as shown in General formula (I) or a tautomer, a mesomer, a racemate, an enantiomer, a diastereoisomer thereof, a mixture thereof, and a pharmaceutically acceptable salt thereof, or the pharmaceutical composition, in the preparation of a drug for treating and/or preventing diseases such as tumors and inflammations.

According to the present invention, the drug may be in any dosage form of drugs, including but not limited to tablets, capsules, liquores, lyophilized formulations and injections. The pharmaceutical formulation according to the present invention may be dosed in the form of a dose unit containing a predetermined amount of active ingredients per dose unit. Such a unit may comprise, for example, 0.5 mg to 1 g, preferably 1 mg to 700 mg, and particularly preferably 5 mg to 300 mg of the compound according to the present invention, depending on the disease being treated, the method of dosage and the age, weight and condition of the patient, or the pharmaceutical formulation may be dosed in the form of a dose unit containing a predetermined amount of active ingredients per dose unit. A preferred dose unit formulation is that comprising the daily dose or divided dose or a corresponding fraction of the active ingredients as indicated above. In addition, this type of pharmaceutical formulation can be prepared by a method well known in the pharmaceutical art.

The pharmaceutical formulation according to the present invention can be dosed through any suitable method as required, such as oral (including oral or sublingual), rectal, nasal, topical (including oral, sublingual or transdermal), and vaginal or parenteral (including subcutaneous, intramuscular, intravenous or intradermal) methods. All methods known in the pharmaceutical art can be used to prepare such a formulation by, for example, combining active ingredients with one or more excipients or one or more adjuvants.

Pharmaceutical formulations suitable for oral administration may be dosed in independent units, such as capsules or tablets; powders or granules; solutions or suspensions in aqueous or non-aqueous liquids; or oil-in-water liquid emulsions or water-in-oil liquid emulsions.

The present invention also relates to a method for treating or preventing FGFR, and in particular FGFR4 mediated diseases (e.g., tumors or inflammatory diseases), including administering a therapeutically effective amount of the compound as shown in General formula (I) or an isomer, a prodrug, a stable isotopic derivative or a pharmaceutically acceptable salt thereof, and a pharmaceutically acceptable carrier, diluent and excipient as described in the present invention, to a patient in need thereof.

A further aspect of the present invention relates to a compound as shown in General formula (I) or an isomer, a prodrug, a stable isotopic derivative thereof or a pharmaceutically acceptable salt and a pharmaceutically acceptable carrier, diluent and excipient thereof, for use in treating and or preventing FGFR and particularly FGFR4 mediated diseases, for example, tumors or inflammatory diseases.

Another aspect of the present invention relates to a compound as shown in General formula (I) or a tautomer, a mesomer, a racemate, an enantiomer, a diastereoisomer thereof, a mixture thereof, and a pharmaceutically acceptable salt thereof, for treating and/or preventing diseases such as tumors.

Preparation Scheme

The present invention further provides a method for preparing the compound.

Scheme 1

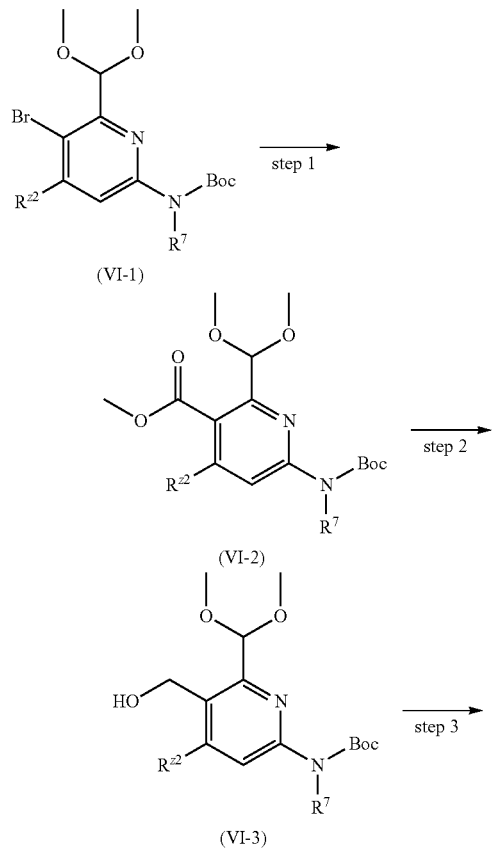

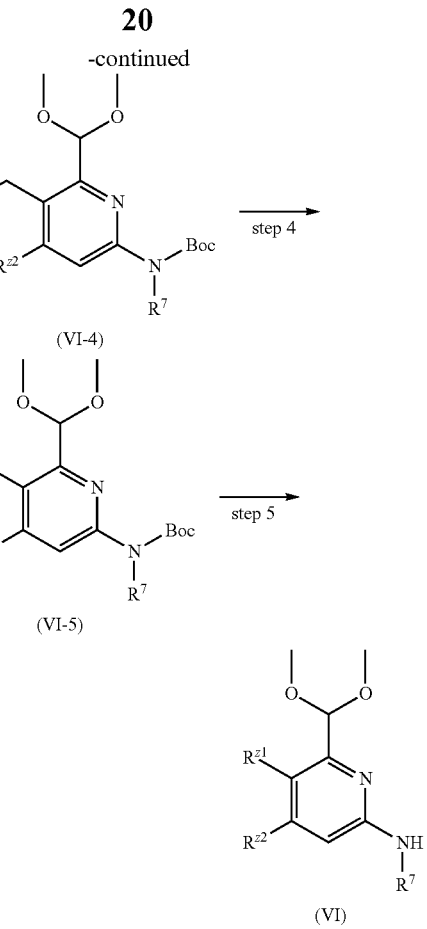

Step 1: $R^{Z2}$ and $R^7$ in the structure of compound (VI-1) are consistent with those in the structure (VI), and the compound (VI-2) is synthesized from the compound (VI-1) through catalysis performed by palladium (palladium acetate) to insert carbon, with 1,1-bis(diphenyl phosphine) ferrocene as a ligand and triethyl amine as an alkali, where $R^{Z2}$ and $R^7$ in the compound (VI-2) are consistent with those in the structure (VI).

Step 2: the ester in the compound (VI-2) is reduced by a reducing agent (sodium borohydride), to synthesize the compound (VI-3), and $R^{Z2}$ and $R^7$ in the compound (VI-3) are consistent with those in the structure (VI).

Step 3: the hydroxy group in the structure (VI-3) is substituted, and the compound (VI-4) is synthesized with phosphorus tribromide as a reaction agent, and $R^{Z2}$ and $R^7$ in the compound (VI-4) are consistent with those in the structure (VI).

Step 4: bromide in the structure (VI-4) is substituted with a nucleophilic reagent (morpholin-3-one, 4-methylpiperazin-2-one, and the like), and the compound (VI-5) is synthesized with an alkali (sodium hydride) as a deprotonating agent, and $R^{Z2}$ and $R^7$ in the compound (VI-5) are consistent with those in the structure (VI).

Step 5: $R^{Z2}$ and $R^7$ in the compound (VI-5) are consistent with those in the structure (VI), where the amino protecting group can be removed by acid (trifluoroacetic acid), alkalified with triethyl amine, and purified to obtain the compound (VI).

Scheme 2

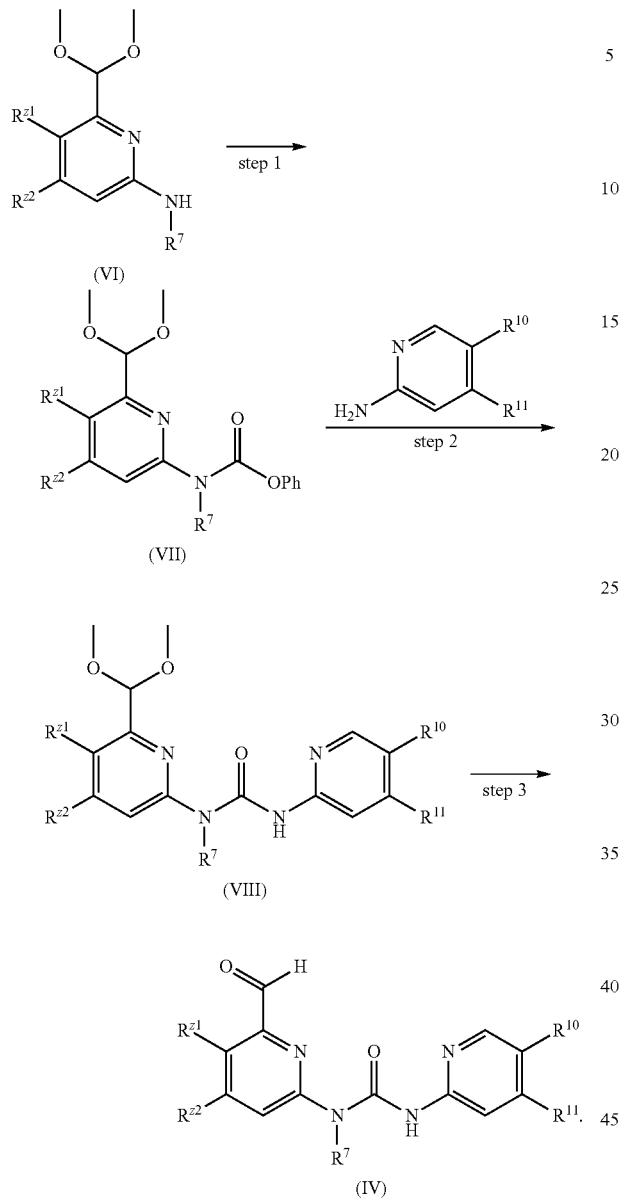

Scheme 3

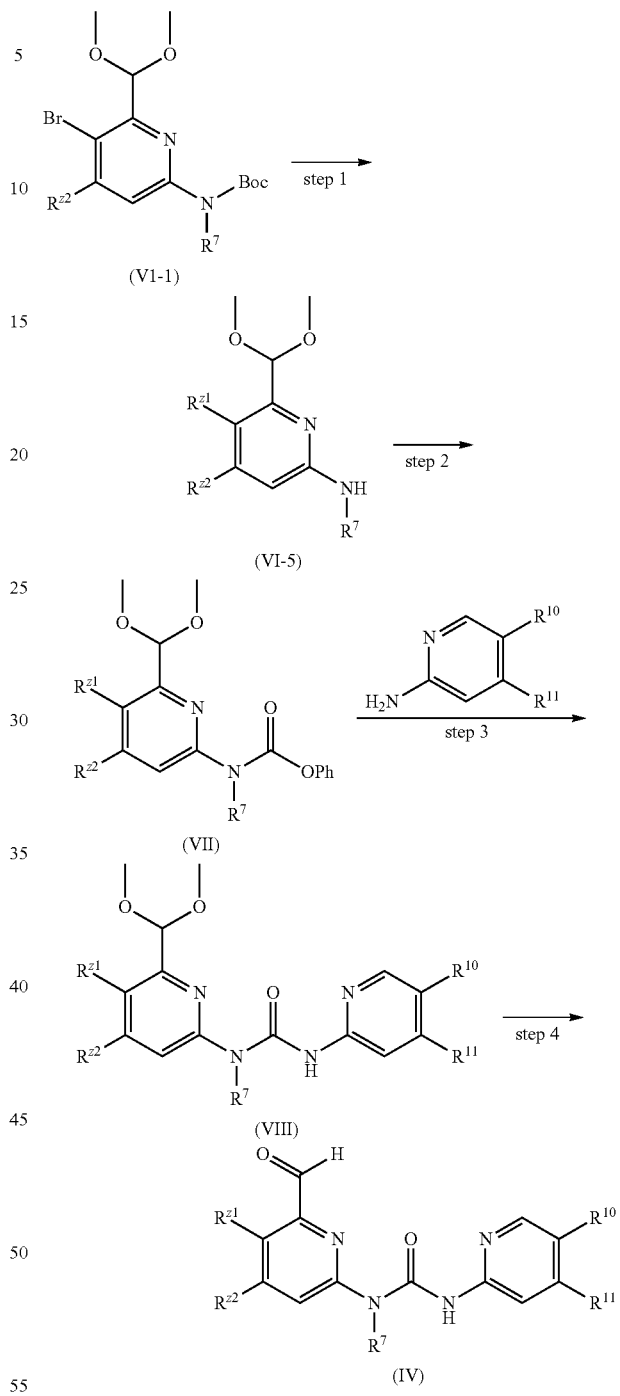

Step 1: $R^{Z1}$, $R^{Z2}$ and $R^7$ in the structure of compound (VI) are consistent with those in the structure (IV), the compound (VI) is activated by an acylating agent (diphenyl carbonate or phenyl chloroformate) with an alkali (lithium hexamethyldisilazide) as a deprotonating agent, to synthesize the compound (VII).

Step 2: $R^{10}$ and $R^{11}$ on 2-aminopyridine are consistent with those in the structure (IV), the phenolic group in the compound (VII) is substituted, and the compound (VIII) is synthesized with an alkali (lithium hexamethyldisilazide) as a deprotonating agent, and $R^{Z1}$, $R^{Z2}$ and $R^7$ in the compound (VIII) are consistent with those in the structure (IV).

Step 3: $R^{Z1}$, $R^{Z2}$ and $R^7$ in the compound (VIII) are consistent with those in the structure (IV), where the acetal protecting group can be removed by acid, alkalified with sodium bicarbonate, and purified to obtain the compound (IV).

Step 1: $R^{Z2}$ and $R^7$ in the structure of compound (VI-1) are consistent with those in the structure (IV), and the compound (VI-5) is synthesized from the compound (VI-1) through palladium catalysis and some boronic compounds to perform carbon-carbon coupling, where the catalyst is [1,1'-bis(diphenylphosphino) ferrocene] palladium chloride, the alkali is potassium carbonate, and $R^{Z1}$, $R^{Z2}$ and $R^{10}$ in the compound (VI-5) are consistent with those in the structure (IV). Step 2, Step 3, and Step 4 have been illustrated in Scheme 2.

Definitions

Unless stated to the contrary, the following terms used in the description and the claims have the following meanings.

The expression "Cx-y" as used herein represents the range of the number of carbon atoms, where both x and y are integers. For example, C3-8 cyclyl represents a cyclyl group having 3 to 8 carbon atoms, and —C0-2 alkyl represents an alkyl group having 0 to 2 carbon atoms, where —C0 alkyl refers to a single chemical bond.

The term "alkyl" as used herein refers to a saturated aliphatic hydrocarbon group, including linear and branched groups having 1 to 20 carbon atoms, for example, linear and branched groups having 1 to 18 carbon atoms, 1 to 12 carbon atoms, 1 to 8 carbon atoms, 1 to 6 carbon atoms or 1 to 4 carbon atoms. Non-limiting examples include methyl, ethyl, n-propyl, i-propyl, n-butyl, i-butyl, t-butyl, s-butyl, n-pentyl, 1,1-dimethyl propyl, 1,2-dimethyl propyl, 2,2-dimethyl propyl, 1-ethyl propyl, 2-methyl butyl, 3-methyl butyl, n-hexyl, 1-ethyl-2-methyl propyl, 1,1,2-trimethyl propyl, 1,1-dimethyl butyl, 1,2-dimethyl butyl, 2,2-dimethyl butyl, 1,3-dimethyl butyl, 2-ethyl butyl, and various branched isomers thereof, etc. Alkyl may be substituted or unsubstituted.

The term "alkylene" as used herein refers to a bivalent saturated aliphatic radical, linear or branched, derived from an alkane by removal of two hydrogen atoms from carbon atoms, or from an alkyl by removal of one hydrogen atom. For example, ethylene is —CH$_2$CH$_2$—, propylene is —CH$_2$CH$_2$CH$_2$—, and butylene is —CH$_2$CH$_2$CH$_2$CH$_2$—.

The term "cyclyl" herein refers to saturated or partially unsaturated monocyclic or polycyclic hydrocarbon groups, comprising 3 to 12 cyclic carbon atoms, such as 3 to 12, 3 to 10, 3 to 8 or 3 to 6 cyclic carbon atoms, or 3, 4, 5, 6, 7, 8-membered rings. Non-limiting examples of monocyclic cyclyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Cyclyl may be substituted or unsubstituted.

The term "heterocyclyl" herein refers to a saturated or partially unsaturated monocyclic or polycyclic group, comprising 3 to 20 ring carbon atoms, such as 3 to 16, 3 to 12, 3 to 10, 3 to 8 or 3 to 6 ring atoms, where one or more ring atoms are heteroatoms selected from the group consisting of nitrogen, oxygen or S(O)m (where m is an integer of 0 to 2), but excluding ring parts of —O—O—, —O—S— or —S—S—, and the remaining ring atoms are carbon. Preferably 3 to 12 ring atoms, of which 1 to 4 are heteroatoms, are comprised. More preferably the heterocyclyl ring comprises 3 to 10 ring atoms. 5 membered rings or 6 membered rings, where 1 to 4 are heteroatoms, more preferably 1 to 3 are heteroatoms, and the most preferably 1 to 2 are heteroatoms, are the most preferred. Non-limiting examples of monocyclic heterocyclyl include pyrrolidinyl, piperidyl, piperazinyl, morpholinyl, thiomorpholinyl, homopiperazinyl and the like. Polycyclic heterocyclic groups include spirocyclic, fused and bridged cyclic heterocyclyl groups.

The term "spiroheterocyclic group" herein refers to a 5 to 20 membered polycyclic heterocyclic group with one atom (referred to as a spiro atom) shared between monocyclic rings, where one or more of the ring atoms are heteroatoms selected from the group consisting of nitrogen, oxygen or S(O)m (where m is an integer of 0 to 2), and the rest of the ring atoms are carbon. They may contain one or more double bonds, but none of the rings has a completely conjugated pi electron system. They are preferably 6 to 14 membered, and more preferably 7 to 10 membered. According to the number of spiro atoms shared between rings, spirocyclyl groups are divided into mono-spiroheterocyclyl, bi-spiroheterocyclyl or poly-spiroheterocyclyl, and the spirocyclyl groups are preferably mono-spirocyclyl and bi-spirocyclyl, and preferably 4 membered/4 membered, 4 membered/5 membered, 4 membered/6 membered, 5 membered/5 membered, or 5 membered/6 membered mono-spirocyclyl. Non-limiting examples of spirocyclyl include

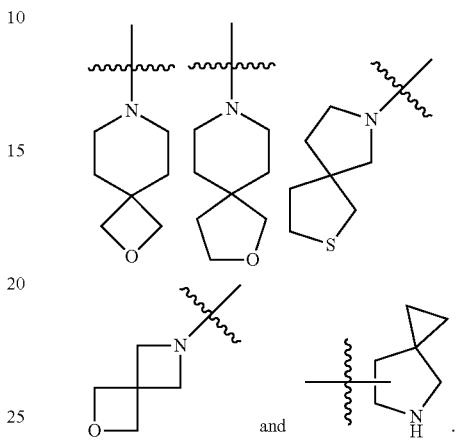

The term "fused heterocyclyl" herein refers to a 5 to 20 membered polycyclic heterocyclyl group where each ring in the system shares a pair of adjacent atoms with other rings in the system, one or more rings may contain one or more double bonds, but none of the rings has a completely conjugated pi electron system, where one or more ring atoms are heteroatoms selected from the group consisting of nitrogen, oxygen or S(O)m (where m is an integer of 0 to 2), and the remaining ring atoms are carbon. They are preferably 6 to 14 membered, and more preferably 7 to 10 membered. According to the number of rings, they can be divided into bicyclic, tricyclic, tetracyclic or polycyclic fused heterocyclyl, and the fused heterocyclyl groups are preferably bicyclic or tricyclic, and more preferably 5 membered/5 membered, or 5 membered/6 membered bicyclic fused heterocyclyl. Non-limiting examples of fused heterocyclyl include

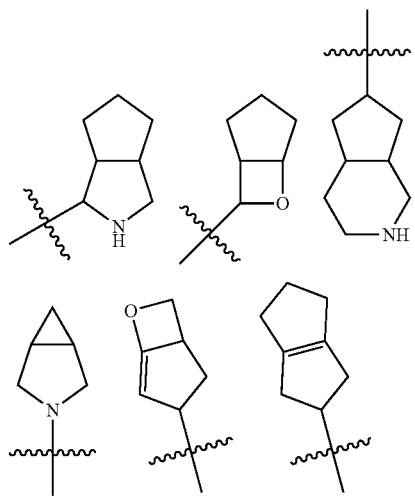

-continued

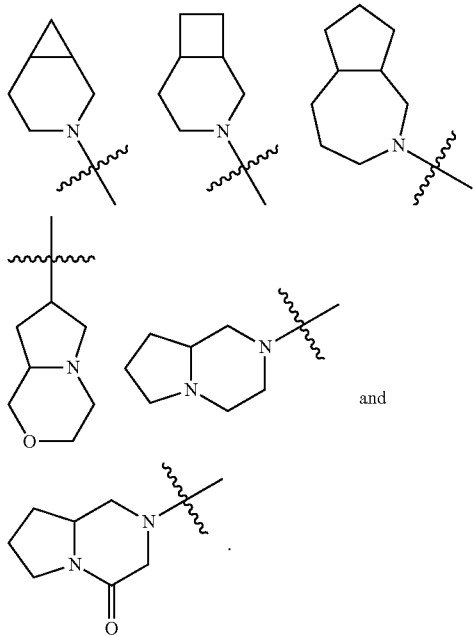

The heterocyclyl ring may be fused to an aryl, a heteroaryl or a cyclyl ring, in which the ring connected with the parent structure is a heterocyclyl group, and the non-limiting examples include:

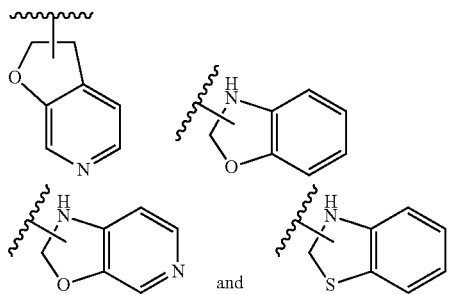

and the like. The heterocyclyl group may be substituted or unsubstituted.

The term "aryl" herein refers to a 6 to 14 membered all-carbon monocyclic or condensed polycyclic (i.e., rings sharing adjacent pairs of carbon atoms) group, and a polycyclic (i.e., rings bearing adjacent pairs of carbon atoms) group having a conjugated pi-electron system, preferably 6 to 10 membered, for example, phenyl and naphthyl, and most preferably phenyl. The aryl ring may be fused to a heteroaryl, a heterocyclyl or a cyclyl ring, in which the ring connected with the parent structure is an aryl ring, and the non-limiting examples include:

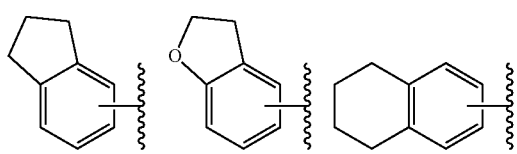

-continued

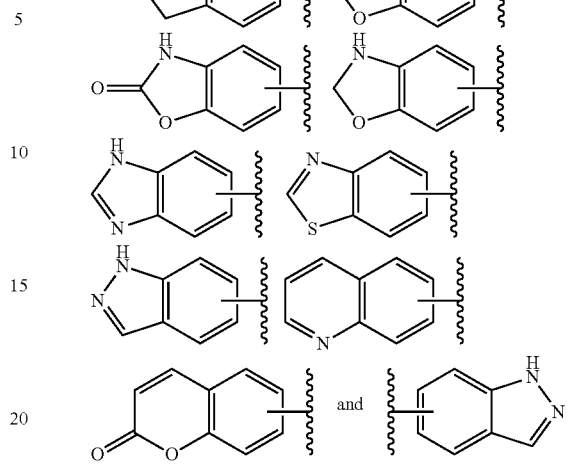

Aryl may be substituted or unsubstituted.

The term "heteroaryl" herein refers to a heteroaromatic system comprising 1 to 4 heteroatoms and 5 to 14 ring atoms, where the heteroatoms include oxygen, sulfur and nitrogen. Heteroaryl is preferably 5 to 10 membered, and more preferably 5 membered or 6 membered, e.g., furyl, thienyl, pyridyl, pyrrolyl, N-alkylpyrrolyl, pyrimidinyl, pyrazinyl, imidazolyl, tetrazyl, oxazolyl, and i-oxazolyl. The heteroaryl ring can be fused to an aryl, a heterocyclyl or a cyclyl ring, where the ring connected with the parent structure is a heteroaryl ring, and the non-limiting examples include:

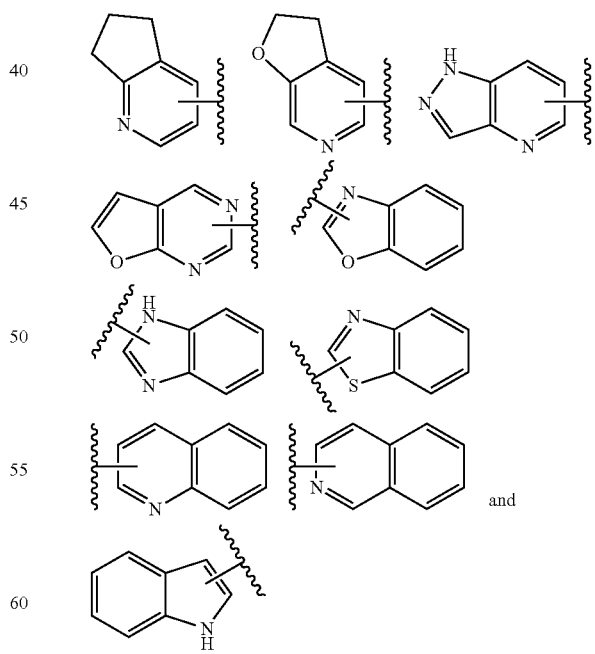

Heteroaryl may be substituted or unsubstituted.

The term "halogen" herein refers to fluorine, chlorine, bromine or iodine.

The term "cyano" herein refers to —CN.

The term "alkenyl" herein refers to a linear, branched or cyclic non-aromatic hydrocarbon group containing at least one carbon-carbon double bond, where 1 to 3 carbon-carbon double bonds may be present and preferably 1 carbon-carbon double bond may be present, including vinyl, propenyl, butenyl, 2-methyl butenyl and cyclohexenyl. The alkenyl group may be substituted. The term "C2-4 alkenyl" refers to alkenyl having 2 to 4 carbon atoms.

The term "alkynyl" herein refers to a linear, branched or cyclic hydrocarbon group containing at least one carbon-carbon triple bond, where 1 to 3 carbon-carbon triple bonds may be present and preferably 1 carbon-carbon triple bond may be present, including acetenyl, propynyl, butynyl and 3-methyl butynyl. The term "C2-4 alkynyl" refers to alkynyl having 2 to 4 carbon atoms.

The term "alkoxy" herein refers to a cyclic or non-cyclic alkyl group with the number of carbon atoms connected by an oxo bridge, including alkyloxy, cycloalkyloxy and heterocycloalkyloxy. Thus, "alkoxy" includes the above definitions of alkyl, heterocycloalkyl and cycloalkyl. "Optional" and "optionally" means that an event or environment described subsequently may but does not necessarily occur, including cases where the event or environment occurs or does not occur. For example, "heterocyclyl optionally substituted with alkyl" means that alkyl may but does not necessarily exist, including cases where heterocyclyl is substituted with alkyl and not substituted with alkyl.

The term "substituted" herein refers that one or more hydrogen atoms, preferably at most 5 and more preferably 1 to 3 hydrogen atoms, in a group are substituted independently with a corresponding number of substituents. It goes without saying that, substituents are only located in their possible chemical positions, and a person skilled in the art can determine (experimentally or theoretically) possible or impossible substitutions without a lot of efforts. For example, amino or hydroxy groups having free hydrogen may be unstable when combined with carbon atoms having unsaturated (e.g. olefinic) bonds.

The term "pharmaceutical composition" herein represents a mixture of one or more of the compounds described herein or physiologically/pharmaceutically acceptable salts or prodrugs with other chemical components, as well as other components such as physiologically/pharmaceutically acceptable carriers and excipients. An object of the pharmaceutical compositions is to promote the dosage of drugs to organisms, facilitate the absorption of active ingredients and thus exert biological activity.

The "room temperature" in the present invention refers to 15 to 30° C.

The term "stable isotopic derivative" herein includes: derivatives substituted with isotopes obtained by substituting any hydrogen atom in Formula I with 1 to 5 deuterium atoms, derivatives substituted with isotopes obtained by substituting any carbon atom in Formula I with 1 to 3 carbon-14 atoms, or derivatives substituted with isotopes obtained by substituting any oxygen atom in Formula I with 1 to 3 oxygen-18 atoms.

The "pharmaceutically acceptable salts" as described in the present invention are discussed in Berge, et al., "Pharmaceutically acceptable salts," *J. Pharm. Sci.*, 66, 1-19 (1977), and it is obvious to pharmaceutical chemists that said salts are essentially non-toxic and can provide desired pharmacokinetic properties, palatability, absorption, distribution, metabolism or excretion, and the like.

The pharmaceutically acceptable salts according to the present invention can be synthesized through a common chemical method.

In general, the preparation of salts can be achieved by reacting free alkalis or acids with equivalent chemical equivalents or excess amounts of acids (inorganic or organic acids) or alkalis in suitable solvents or solvent compositions.

The "prodrug" as described in the present invention refers to a compound that is converted into an original active compound after being metabolized in vivo. Representatively speaking, prodrugs are inactive substances, or have activity lower than the active parent compounds but can provide convenient operation and dosage or improve metabolic characteristics.

The "isomer" of the present invention refers that the compound of Formula (I) according to the present invention may have an asymmetric center and a racemate, a racemic mixture and a single diastereoisomer, where these isomers, including stereoisomers and geometric isomers, are all included in the present invention. The geometric isomers include cis- and trans-isomers.

The term "tumor" herein includes benign tumor and malignant tumor, for example, cancer.

The term "cancer" herein includes various malignant tumor, especially those in which FGFR and in particular FGFR4 is involved, including but not limited to rhabdomyosarcoma, renal cell carcinoma, myeloma, breast cancer, gastric cancer, colon cancer, bladder cancer, pancreatic cancer and hepatocellular cancer.

The term "inflammatory disease" herein refers to any inflammatory disease in which FGFR and in particular FGFR4 is involved.

EXAMPLES

The present invention will be further illustrated by means of examples below, but is not therefore limited to the scope of the examples described. In the following examples, experimental methods without specific conditions noted are selected according to conventional methods and conditions or according to product instructions.

The structures of all the compounds according to the present invention can be identified by nuclear magnetic resonance (1H NMR) and/or mass spectrometric detection (MS).

$^1$H NMR chemical shift ($\delta$) is recorded in PPM (unit: $10^{-6}$ PPM). NMR is carried out by a Bruker AVANCE-400 spectrometer. Appropriate solvents include deuterated chloroform ($CDCl_3$), deuterated methanol ($CD_3OD$) and deuterated dimethylsulfoxide (DMSO-$d^6$), with tetramethylsilane as an internal standard (TMS).

The low resolution mass spectrogram (MS) is determined by an Agilent 1260HPLC/6120 mass spectrometer, using Agilent ZORBAX XDB-C18, 4.6×50 mm, 3.5 μm, at a gradient elution condition I: 0:95% solvent A1 and 5% solvent B1, 1-2:5% solvent A1 and 95% solvent B1; 2.01-2.50:95% solvent A1 and 5% solvent B1. The percentage is the volume percentage of a certain solvent based on the total solvent volume. Solvent A1:0.01% formic acid aqueous solution; solvent B1:0.01% formic acid solution in acetonitrile; and the percentage is the volume percentage of a solute based on the solution.

The thin-layer silica gel plate is a Yantai Yellow Sea HSGF254 or Qingdao GF254 silica gel plate. The Yantai Yellow Sea 100-200 or 200-300 mesh silica gel is generally used as the support in the column chromatography.

The known starting raw materials of the present invention can be synthesized by or in accordance with methods known in the art, or can be purchased from companies such as Acros Organics, Aldrich Chemical Company, Accela ChemBio Inc., Shanghai Bide Pharmatech, Shanghai Aladdin Chemistry, Shanghai Meryer Chemistry, Accelerating Chemistry, etc.

In the examples, unless stated specially, the solvents used in the reaction are all anhydrous solvents, where anhydrous tetrahydrofuran is commercially available tetrahydrofuran, sodium blocks are used as a dehydrant, benzophenone is used as an indicator, the solution is refluxed under the protection of nitrogen gas until the it assumes a bluish violet color, it is distilled and collected, and stored at room temperature under the protection of nitrogen gas, and the other anhydrous solvents are purchased from Aladdin Chemistry and Accelerating Chemistry, and transfer and use of all anhydrous solvents shall be carried out under the protection of nitrogen gas unless specially noted.

In the examples, the reactions are all carried out under an argon atmosphere or nitrogen atmosphere unless specially noted.

The argon atmosphere or nitrogen atmosphere refers that the reaction flask is connected to an argon or nitrogen balloon with a volume of about 1 L.

The hydrogen atmosphere refers that the reaction flask is connected to a hydrogen balloon with a volume of about 1 L.

The carbon monoxide atmosphere refers that the reaction flask is connected to a carbon monoxide balloon with a volume of about 1 L.

In hydrogenation, the reaction is usually vacuumed and filled with hydrogen gas, and this is repeated 3 times.

The reaction temperature is the room temperature, and the temperature range is from 15° C. to 30° C., unless specially noted.

The thin-layer chromatography method (TLC) is employed to monitor the reaction process in the examples. The developer system used in the reaction includes: A, which is a dichloromethane and methanol system, and B: which is a petroleum ether and ethyl acetate system, and the ratio by volume of the solvents is adjusted according to the polarity of the compounds.

The eluent system for column chromatography and the developer system for thin-layer chromatography employed in the purification of compounds include: A, which is a dichloromethane and methanol system, and B: which is a petroleum ether and ethyl acetate system, and the ratio by volume of the solvents is adjusted according to the polarity of the compounds, and a small amount of triethyl amine and acid or alkaline reagents and the like can also be added for the adjustment.

Example 1

3-(5-cyano-4-((2-methoxyethyl) amino) pyrid-2-yl)-1-(6-formylpyrid-2-yl)-1-methyl urea

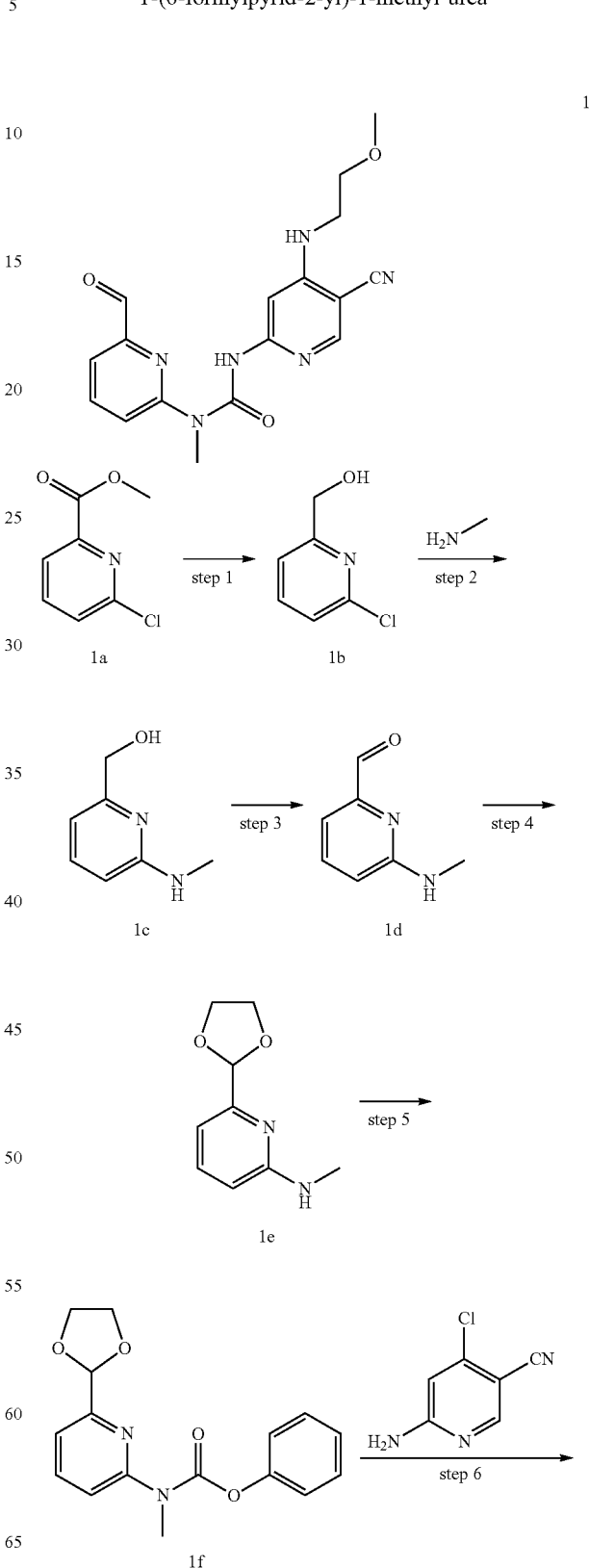

-continued

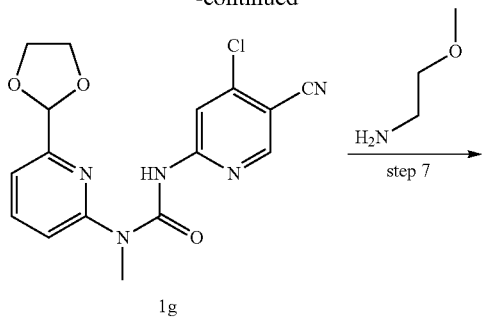

Step 1

6-chloro-2-hydroxymethyl pyridine

Compounds methyl 6-chloro-2-pyridine formate 1a (1.00 g, 5.85 mmol), sodium borohydride (0.38 g, 9.95 mmol) and ethanol (15 mL) were mixed and stirred for 6 h at room temperature. This mixture was quenched with 30 mL of water, extracted with ethyl acetate (50 mL×2), and the organic phase was washed with saturated brine (50 mL×2). The organic phase was dried over anhydrous sodium sulfate, filtered to remove the drying agent, and subjected to exsolution under reduced pressure, to obtain a target product 6-chloro-2-hydroxymethyl pyridine 1b (0.70 g, yellow oil), at a yield of 84%. The product was directly used in the next reaction without purification.

$^1$H NMR (400 MHz, CDCl$_3$) δ 7.68 (dd, J=8.0, 7.6 Hz, 1H), 7.27 (d, J=8.0 Hz, 1H), 7.26 (d, J=7.6 Hz, 1H), 4.76 (d, J=5.2 Hz, 2H), 3.07 (t, J=5.6 Hz, 1H).

Step 2

(6-(methylamino) pyrid-2-yl)methanol

Compounds 6-chloro-2-hydroxymethyl pyridine 1 b (1.50 g, 10.5 mmol) was mixed with methylamine (15 mL, 30% solution in ethanol), and stirred for 48 h at 100° C. The mixture was cooled to room temperature and subjected to exsolution under reduced pressure. The residuals were purified through silica gel column chromatography (petroleum ether/ethyl acetate 10:1 to 1:2), to obtain a target product (6-(methylamino) pyrid-2-yl) methanol 1c (0.70 g, yellow oil), at a yield of 48%.

MS m/z (ESI): 139 [M+1].

Step 3

6-(methylamino) methylpyridine aldehyde

Compounds (6-(methylamino) pyrid-2-yl) methanol 1c (0.60 g, 4.35 mmol), manganese dioxide (3.78 g, 43.5 mmol) and dichloromethane (15 mL) were mixed, and stirred for 16 h at 40° C. The mixture was cooled to room temperature, and filtered. The filtrate was subjected to exsolution under reduced pressure, to obtain a target product 6-(methylamino) methylpyridine aldehyde 1d (0.50 g, yellow solid), at a yield of 72%.

MS m/z (ESI): 137 [M+1].

Step 4

6-(1,3-dioxolan-2-yl)-N-methylpyridin-2-amine

Compounds 6-(methylamino) methylpyridine aldehyde 1d (0.80 g, 5.95 mmol), ethylene glycol (1.80 g, 29.7 mmol), p-toluene sulfonic acid (0.10 g, 0.60 mmol), 4 A molecular sieve (0.2 g), and toluene (15 mL) were mixed and stirred for 5 h at 120° C. The mixture was cooled to room temperature, and this mixture was diluted with 30 mL of water, extracted with ethyl acetate (50 mL×2), and the organic phase was washed with saturated brine (50 mL×2). The organic phase was dried over anhydrous sodium sulfate, and filtered to remove the drying agent. The residuals were purified through silica gel column chromatography (petroleum ether/ethyl acetate 6:1 to 2:1), to obtain the target product 6-(1,3-dioxolan-2-yl)-N-methylpyridin-2-amine (0.60 g, yellow solid), at a yield of 57%.

MS m/z (ESI): 181 [M+1]

$^1$H NMR (400 MHz, CDCl$_3$) δ 7.51 (t, J=8.0 Hz, 1H), 6.83 (d, J=7.2 Hz, 1H), 6.39 (d, J=8.0 Hz, 1H), 5.72 (s, 1H), 4.66 (brs, 1H), 4.20-4.14 (m, 2H), 4.09-4.03 (m, 2H), 2.93 (d, J=4.8 Hz, 3H).

Step 5

Phenyl (6-(1,3-dioxolan-2-yl) pyrid-2-yl)(methyl) aminocarboxylate

Compounds 6-(1,3-dioxolan-2-yl)-N-methylpyridin-2-amine 1e (54 mg, 0.30 mmol), diphenyl carbonate (1.28 g, 0.60 mmol), lithium hexamethyldisilazide (0.41 mL, 0.41 mmol, 1 M solution in tetrahydrofuran) and tetrahydrofuran (3 mL) were mixed and stirred for 2 h at 0° C. This mixture was quenched with 10 mL of a saturated ammonium chloride solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 4:1), to obtain the target product (6-(1,3-dioxolan-2-yl) pyrid-2-yl)(methyl) aminocarboxylate (60 mg, white solid), at a yield of 67%.

MS m/z (ESI): 301 [M+1]

$^1$H NMR (400 MHz, CDCl$_3$) δ 7.96-7.94 (m, 1H), 7.74-7.70 (m, 1H), 7.45-7.32 (m, 2H), 7.40-7.38 (m, 1H), 7.28-7.25 (m, 1H), 7.20-7.17 (m, 2H), 5.87 (s, 1H), 4.24-4.21 (m, 2H), 4.13-4.09 (m, 2H), 3.67 (s, 3H).

Step 6

1-(6-(1,3-dioxolan-2-yl)pyrid-2-yl)-3-(4-chloro-5-cyanopyrid-2-yl)-1-methylurea

Compounds phenyl (6-(1,3-dioxolan-2-yl) pyrid-2-yl) (methyl) aminocarboxylate 1f (60 mg, 0.20 mmol), 6-amino-4-chloronicotinonitrile (76 mg, 0.50 mmol), lithium hexamethyldisilazide (0.4 mL, 0.4 mmol, 1 M solution in tetrahydrofuran) and tetrahydrofuran (2 mL) were mixed and stirred for 2 h at room temperature. This mixture was quenched with 10 mL of a saturated ammonium chloride solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 30:1), to obtain the target product 1-(6-(1,3-dioxolan-2-yl) pyrid-2-yl)-3-(4-chloro-5-cyanopyrid-2-yl)-1-methylurea (22 mg, white solid), at a yield of 31%.

MS m/z (ESI): 360 & 362 [M+1]

$^1$H NMR (400 MHz, DMSO-d$_6$) δ 13.44 (s, 1H), 8.87 (s, 1H), 8.33 (s, 1H), 8.04-8.00 (m, 1H), 7.42 (d, J=8.4 Hz, 1H), 7.36 (d, J=7.6 Hz, 1H), 5.82 (s, 1H), 4.24-4.21 (m, 2H), 4.04-4.01 (m, 2H), 3.44 (s, 3H).

Step 7

1-(6-(1,3-dioxolan-2-yl) pyrid-2-yl)-3-(5-cyano-4 ((2-methoxyethyl)amino) pyrid-2-yl)-1-methylurea Compounds 1-(6-(1,3-dioxolan-2-yl) pyrid-2-yl)-3-(4-chloro-5-cyanopyrid-2-yl)-1-methylurea 1g (22 mg, 0.06 mmol), 2-methoxy ethylamine (14 mg, 0.18 mmol), diisopropyl ethylamine (24 mg, 0.18 mmol) and N,N-dimethyl acetamide (0.4 mL) were mixed and stirred for 16 h at 70° C. This mixture was diluted with 10 mL of water, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 2:1), to obtain the target product 1-(6-(1,3-dioxolan-2-yl) pyrid-2-yl)-3-(5-cyano-4-((2-methoxyethyl)amino) pyrid-2-yl)-1-methylurea (10 mg, white solid), at a yield of 41%.

MS m/z (ESI): 399 [M+1].

Step 8

3-(5-cyano-4-((2-methoxyethyl) amino) pyrid-2-yl)-1-(6-formylpyrid-2-yl)-1-methylurea Compounds 1-(6-(1,3-dioxolan-2-yl) pyrid-2-yl)-3-(5-cyano-4-((2-methoxyethyl)amino) pyrid-2-yl)-1-methylurea 1 h (10 mg, 0.025 mmol), hydrochloric acid (0.5 mL, 37%), water (1 mL) and tetrahydrofuran (2 mL) were mixed and stirred for 6 h at room temperature. This mixture was quenched with a saturated sodium carbonate solution, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 20:1), to obtain the target product 3-(5-cyano-4-((2-methoxyethyl)amino) pyrid-2-yl)-1-(6-formylpyrid-2-yl)-1-methylurea (8 mg, white solid), at a yield of 90%.

MS m/z (ESI): 355 [M+1]

$^1$H NMR (400 MHz, CDCl$_3$) δ 13.03 (s, 1H), 10.18 (s, 1H), 8.21 (s, 1H), 8.02-7.98 (m, 1H), 7.75 (d, J=7.6 Hz, 1H), 7.59 (s, 1H), 7.36 (d, J=8.4 Hz, 1H), 5.82 (s, 1H), 3.66 (t, J=4.8 Hz, 2H), 3.56 (s, 3H), 3.52-3.50 (m, 2H), 3.44 (s, 3H).

Example 2

3-(6-chloropyrimidin-4-yl)-1-(6-formylpyrid-2-yl)-1-methylurea

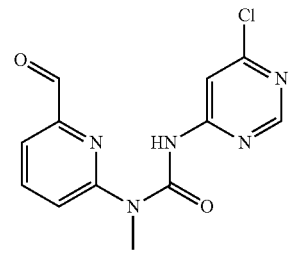

Example 2 was synthesized with reference to the operation steps of Example 1, except that 6-chloropyrimidin-4-amine was substituted for 6-amino-4-chloronicotinonitrile in Step 6.

MS m/z (ESI): 292 & 294 [M+1]

$^1$H NMR (400 MHz, CDCl$_3$) δ 13.51 (s, 1H), 10.18 (s, 1H), 8.67 (s, 1H), 8.25 (s, 1H), 8.02 (dd, J=8.4, 7.6 Hz, 1H), 7.79 (d, J=7.6 Hz, 1H), 7.40 (d, J=8.4 Hz, 1H), 3.59 (s, 3H).

Example 3

3-(5-cyanopyrid-2-yl)-1-(6-formylpyrid-2-yl)-1-methylurea

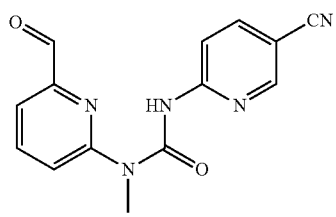

Example 3 was synthesized with reference to the operation steps of Example 1, except that 6-aminonicotinonitrile was substituted for 6-amino-4-chloronicotinonitrile in Step 6.

MS m/z (ESI): 282 [M+1]

¹H NMR (400 MHz, CDCl₃) δ 13.49 (s, 1H), 10.19 (s, 1H), 8.60 (s, 1H), 8.34 (d, J=7.6 Hz, 1H), 8.03 (dd, J=8.8, 7.6 Hz, 1H), 7.95-7.93 (m, 1H), 7.77 (d, J=7.6 Hz, 1H), 7.39 (d, J=8.8 Hz, 1H), 3.59 (s, 3H).

Example 4

3-(4-chloro-5-cyanopyrid-2-yl)-1-(6-formylpyrid-2-yl)-1-methylurea

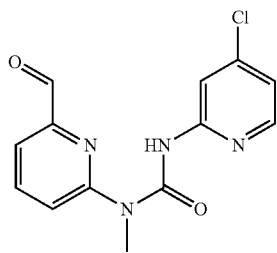

4

Example 4 was synthesized with reference to the operation steps of Example 1, except that 4-chloropyridin-2-amine was substituted for 6-amino-4-chloronicotinonitrile in Step 6.

MS m/z (ESI): 291 & 293 [M+1]

¹H NMR (400 MHz, CDCl₃) δ 13.09 (s, 1H), 10.19 (s, 1H), 8.29 (d, J=2.0 Hz, 1H), 8.22 (d, J=5.2 Hz, 1H), 8.00 (dd, J=8.4, 7.2 Hz, 1H), 7.74 (d, J=7.2 Hz, 1H), 7.37 (d, J=8.4 Hz, 1H), 7.03 (dd, J=5.2, 2.0 Hz, 1H), 3.58 (s, 3H).

Example 5

3-(5-cyano-4-(isopropylamino) pyrid-2-yl)-1-(6-formylpyrid-2-yl)-1-methylurea

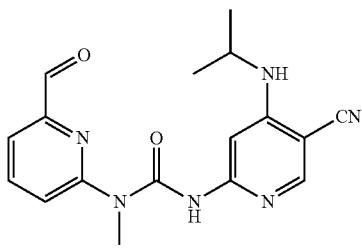

5

Example 5 was synthesized with reference to the operation steps of Example 1, except that isopropyl amine was substituted for 2-methoxy ethylamine in Step 7.

MS m/z (ESI): 339 [M+1]

¹H NMR (400 MHz, CDCl₃) δ 13.00 (s, 1H), 10.18 (s, 1H), 8.20 (s, 1H), 8.02-7.97 (m, 1H), 7.76-7.74 (m, 1H), 7.60 (s, 1H), 7.57-7.54 (m, 1H), 7.36 (d, J=8.4 Hz, 1H), 3.92-3.89 (m, 1H), 3.57 (s, 3H), 1.34 (d, J=6.4 Hz, 6H).

Example 6

3-(5-cyano-4-isopropoxypyrid-2-yl)-1-(6-formylpyrid-2-yl)-1-methylurea

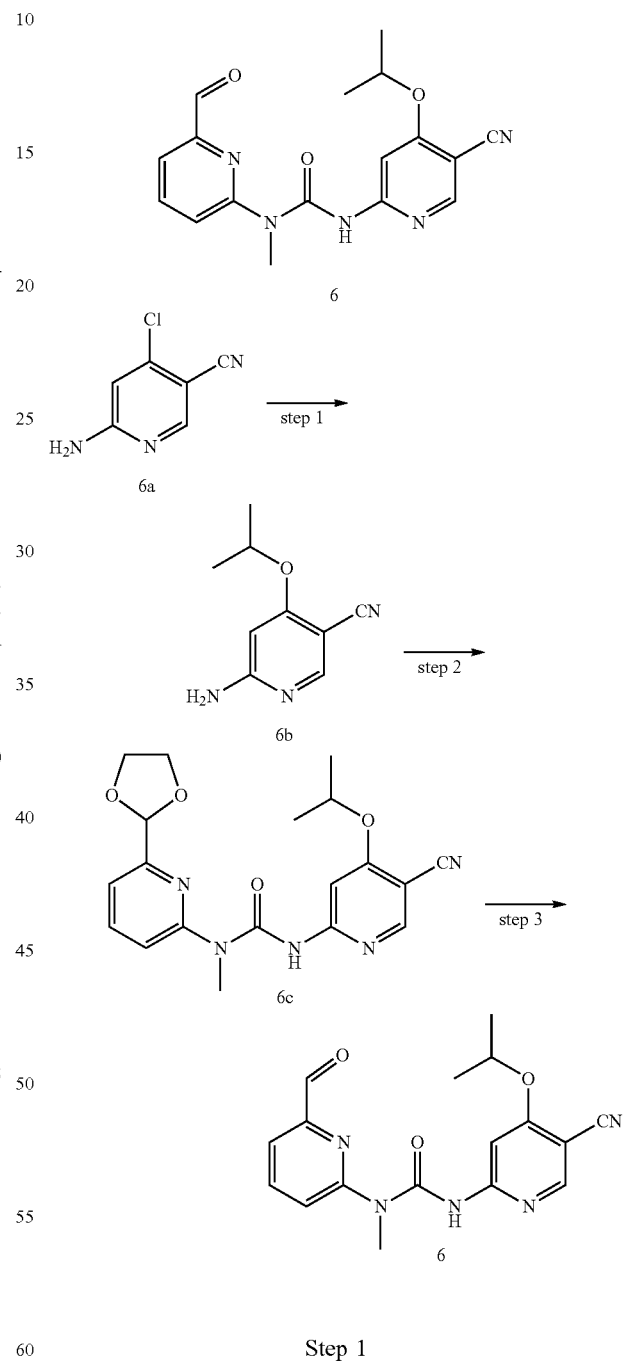

Step 1

6-amino-4-isopropoxy nicotinonitrile

Compounds 6-amino-4-chloronicotinonitrile 6a (46 mg, 0.30 mmol), isopropanol (90 mg, 1.50 mmol), sodium hydride (72 mg, 1.80 mmol, 60% mineral oil mixture) and N-methyl pyrrolidone (1.5 mL) were mixed and stirred for 24 h at 70° C. The mixture was cooled to room temperature, and this mixture was quenched with 20 mL of water, extracted with ethyl acetate (20 mL×2), and the organic phase was washed with saturated brine (20 mL×2). The organic phase was dried over anhydrous sodium sulfate, filtered to remove the drying agent, and subjected to exsolution under reduced pressure. The residuals were purified through a preparative silica gel plate (petroleum ether/ethyl acetate 1:1), to obtain the target product 6-amino-4-isopropoxy nicotinonitrile 6b (16 mg, yellow solid), at a yield of 30%.

MS m/z (ESI): 178 [M+1].

Step 2

1-(6-(1,3-dioxolan-2-yl)pyrid-2-yl)-3-(5-cyano-4-isopropoxypyrid-2-yl)-1-methylurea Example 6c was synthesized with reference to the operation steps in Step 6 of Example 1, except that 6-amino-4-isopropoxy nicotinonitrile was substituted for 6-amino-4-chloronicotinonitrile, to obtain the target product 1-(6-(1,3-dioxolan-2-yl) pyrid-2-yl)-3-(5-cyano-4-isopropoxypyrid-2-yl)-1-methylurea 6c (8 mg, white solid), at a yield of 46%.

MS m/z (ESI): 384 [M+1].

Step 3

3-(5-cyano-4-isopropoxypyrid-2-yl)-1-(6-formylpyrid-2-yl)-1-methylurea

Example 6 was synthesized with reference to the operation steps in Step 8 of Example 1, except that 1-(6-(1,3-dioxolan-2-yl) pyrid-2-yl)-3-(5-cyano-4-isopropoxypyrid-2-yl)-1-methylurea was substituted for 1-(6-(1,3-dioxolan-2-yl) pyrid-2-yl)-3-(5-cyano-4-((2-methoxyethyl)amino)pyrid-2-yl)-1-methylurea, to obtain the target product 3-(5-cyano-4-isopropoxypyrid-2-yl)-1-(6-formylpyrid-2-yl)-1-methylurea 7 (5 mg, white solid), at a yield of 71%.

MS m/z (ESI): 340 [M+1]
$^1$H NMR (400 MHz, CDCl$_3$) δ 13.33 (s, 1H), 10.19 (s, 1H), 8.38 (s, 1H), 8.02 (dd, J=8.0, 7.6 Hz, 1H), 7.96 (s, 1H), 7.77 (d, J=7.6 Hz, 1H), 7.38 (d, J=8.0 Hz, 1H), 4.88-4.86 (m, 1H), 3.58 (s, 3H), 1.48 (d, J=6.0 Hz, 6H).

Example 7

3-(5-cyano-4-(2-methoxyethoxy)pyrid-2-yl)-1-(6-formylpyrid-2-yl)-1-methylurea

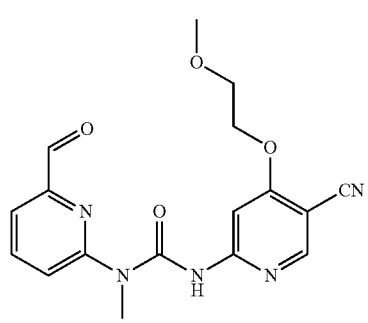

7

Example 7 was synthesized with reference to the operation steps of Example 6, except that 2-methoxy ethylene glycol amine was substituted for isopropanol in Step 1.

MS m/z (ESI): 356 [M+1]
$^1$H NMR (400 MHz, CDCl$_3$) δ 13.38 (s, 1H), 10.18 (s, 1H), 8.40 (s, 1H), 8.02 (dd, J=8.4, 7.2 Hz, 1H), 7.99 (s, 1H), 7.77 (d, J=7.2 Hz, 1H), 7.38 (d, J=8.4 Hz, 1H), 4.38 (t, J=4.8 Hz, 2H), 3.86 (t, J=4.8 Hz, 2H), 3.58 (s, 3H), 3.51 (s, 3H).

Example 8

3-(5-cyano-4-((2-methoxyethyl)amino)pyrid-2-yl)-1-(4-formylpyrimidin-2-yl)-1-methylurea

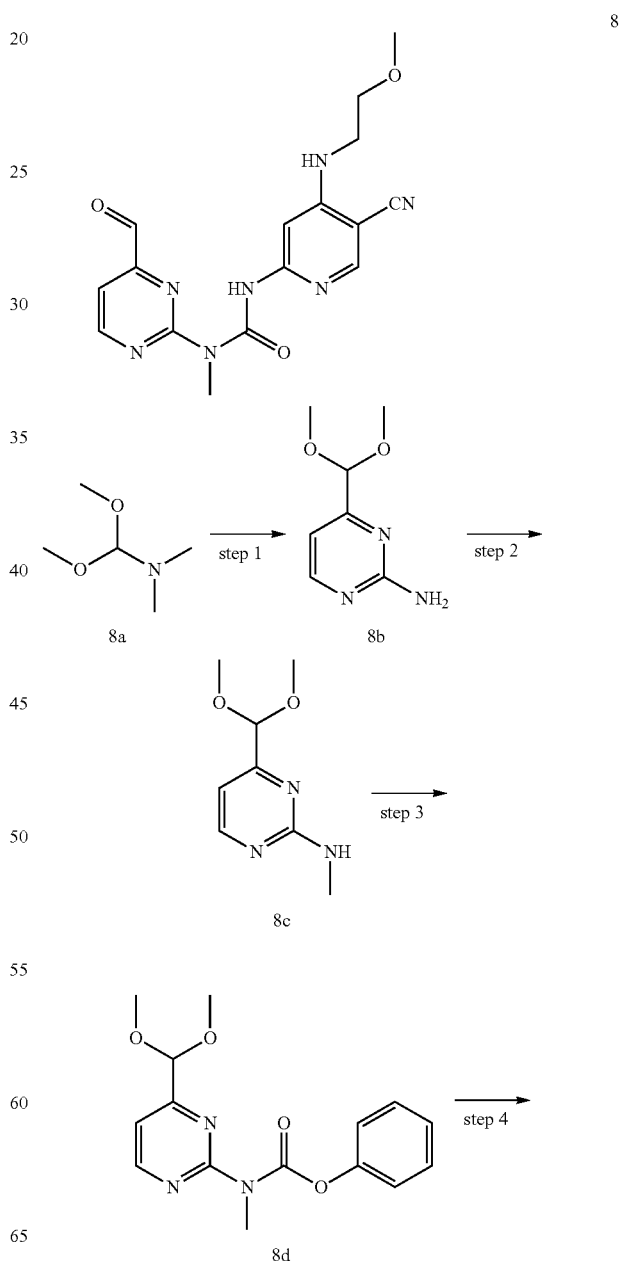

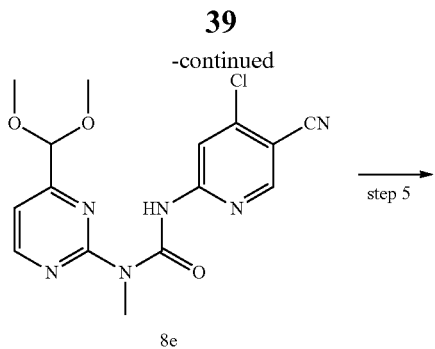

8e

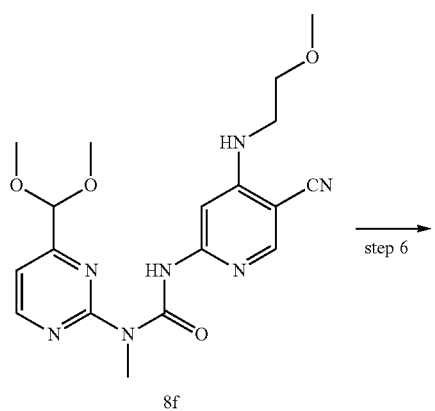

8f

[structure]

8

Step 1

4-(dimethoxymethyl)pyrimidin-2-amine 1,1-dimethoxy-N,N-dimethyl methylamine 8a (4.90 g, 41.36 mmol) was mixed with 1,1-dimethoxypropan-2-one (4.90 g, 41.36 mmol). The mixture was stirred for 16 h at 100° C., and subjected to exsolution under reduced pressure. The residuals were mixed with guanidine hydrochloride (4.30 g, 45.00 mmol), sodium hydroxide (1.80 g, 45.00 mmol) and water (15 mL), and stirred for 48 h at room temperature. Filtration was carried out to obtain the target product 4-(dimethoxymethyl)pyrimidin-2-amine 8b (2.00 g, white solid), at a yield of 27%.

MS m/z (ESI): 170 [M+1]

$^1$H NMR (400 MHz, CDCl$_3$) δ 8.36 (d, J=4.8 Hz, 1H), 6.87 (d, J=5.2 Hz, 1H), 5.16 (s, 1H), 5.15 (brs, 2H), 3.42 (s, 6H).

Step 2

4-(dimethoxymethyl)-N-methylpyrimidin-2-amine

Compounds 4-(dimethoxymethyl)pyrimidin-2-amine 8b (1.00 g, 5.65 mmol), iodomethane (2.80 g, 19.77 mmol) and acetone (30 mL) were mixed. This mixture were stirred for 16 h at 70° C., cooled to room temperature, and filtered. The solid was mixed with 10% sodium hydroxide (8 mL), stirred for 0.5 h at 80° C., and cooled to room temperature. This mixture was quenched with 250 mL of ice water, extracted with dichloromethane (50 mL×2), and the organic phase was washed with saturated brine (50 mL×2). The organic phase was dried over anhydrous sodium sulfate, filtered to remove the drying agent, and subjected to exsolution under reduced pressure, to obtain the target product 8c 4-(dimethoxymethyl)-N-methylpyrimidin-2-amine 8c (0.70 g, yellow oil), at a yield of 67%.

MS m/z (ESI): 184 [M+1]

$^1$H NMR (400 MHz, CDCl$_3$) δ 8.37 (d, J=4.8 Hz, 1H), 6.77 (d, J=5.2 Hz, 1H), 5.18 (brs, 1H), 5.13 (s, 1H), 3.42 (s, 6H), 3.03 (d, J=5.2 Hz, 3H).

Step 3

Phenyl (4-(dimethoxymethyl)pyrimidin-2-yl)(methyl) aminocarboxylate

Compounds 4-(dimethoxymethyl)-N-methylpyrimidin-2-amine 8c (0.20 g, 1.09 mmol), diphenyl carbonate (0.47 g, 2.19 mmol), lithium hexamethyldisilazide (1.5 mL, 1.51 mmol, 1 M solution in tetrahydrofuran) and tetrahydrofuran (5 mL) were mixed and stirred for 2 h at 0° C. This mixture was quenched with 10 mL of a saturated ammonium chloride solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 50:1), to obtain the target product phenyl (4-(dimethoxymethyl)pyrimidin-2-yl)(methyl) aminocarboxylate 8 d (40 mg, white solid), at a yield of 12%.

MS m/z (ESI): 304 [M+1].

Step 4

3-(4-chloro-5-cyanopyrid-2-yl)-1-(4-(dimethoxymethyl)pyrimidin-2-yl)-1-methylurea Compounds phenyl (4-(dimethoxymethyl)pyrimidin-2-yl)(methyl) aminocarboxylate 8 d (40 mg, 0.13 mmol), 6-amino-4-chloronicotinonitrile (21 mg, 0.13 mmol), lithium hexamethyldisilazide (0.26 mL, 0.26 mmol, 1 M solution in tetrahydrofuran) and tetrahydrofuran (2 mL) were mixed and stirred for 2 h at room temperature. This mixture was quenched with 10 mL of a saturated ammonium chloride solution, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 50:1), to obtain the target product 3-(4-chloro-5-cyanopyrid-2-yl)-1-(4-(dimethoxymethyl) pyrimidin-2-yl)-1-methylurea 8e (25 mg, white solid), at a yield of 52%.

MS m/z (ESI): 363 & 365 [M+1]

$^1$H NMR (400 MHz, CDCl$_3$) δ 13.59 (s, 1H), 8.74 (d, J=5.2 Hz, 1H), 8.56 (s, 1H), 8.55 (s, 1H), 7.30 (d, J=5.2 Hz, 1H), 5.34 (s, 1H), 3.68 (s, 3H), 3.51 (s, 6H).

Step 5

3-(5-cyano-4-((2-methoxyethyl) amino) pyrid-2-yl)-1-(4-(dimethoxymethyl) pyrimidin-2-yl)-1-methylurea Compounds 3-(4-chloro-5-cyanopyrid-2-yl)-1-(4-(dimethoxymethyl) pyrimidin-2-yl)-1-methylurea 8e (18 mg, 0.05 mmol), 2-methoxy ethylamine (15 mg, 0.20 mmol), diisopropyl ethylamine (13 mg, 0.10 mmol) and N,N-dimethyl acetamide (0.4 mL) were mixed and stirred for 16 h at 70° C. This mixture was diluted with 10 mL of water, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 50:1), to obtain the target product 3-(5-cyano-4-((2-methoxyethyl)amino) pyrid-2-yl)-1-(4-(dimethoxymethyl)pyrimidin-2-yl)-1-methylurea 8f (15 mg, yellow solid), at a yield of 75%.

MS m/z (ESI): 402 [M+1]

$^1$H NMR (400 MHz, CDCl$_3$) δ 13.11 (s, 1H), 8.72 (d, J=5.2 Hz, 1H), 8.23 (s, 1H), 7.65 (s, 1H), 7.25 (d, J=5.2 Hz, 1H), 5.31 (s, 1H), 5.30 (brs, 1H), 3.67-3.65 (m, 2H), 3.66 (s, 3H), 3.54-3.52 (m, 2H), 3.51 (s, 6H), 3.44 (s, 3H).

Step 6

3-(5-cyano-4-((2-methoxyethyl) amino) pyrid-2-yl)-1-(4-formylpyrimidin-2-yl)-1-methylurea Compounds 3-(5-cyano-4-((2-methoxyethyl)amino) pyrid-2-yl)-1-(4-(dimethoxymethyl) pyrimidin-2-yl)-1-methylurea 8f (15 mg, 0.04 mmol), hydrochloric acid (0.8 mL, 37%), water (1 mL) and tetrahydrofuran (2 mL) were mixed and stirred for 3 h at room temperature. This mixture was quenched with a saturated sodium carbonate solution, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 50:1), to obtain the target product 3-(5-cyano-4-((2-methoxyethyl) amino) pyrid-2-yl)-1-(4-formylpyrimidin-2-yl)-1-methylurea 8 (6 mg, white solid), at a yield of 27%.

MS m/z (ESI): 356 [M+1]

$^1$H NMR (400 MHz, CDCl$_3$) δ 13.88 (s, 1H), 10.06 (s, 1H), 8.95 (d, J=4.8 Hz, 1H), 8.23 (s, 1H), 7.65 (s, 1H), 7.52 (d, J=4.8 Hz, 1H), 5.35 (brs, 1H), 3.73 (s, 3H), 3.69-3.65 (m, 2H), 3.55-3.52 (m, 2H), 3.45 (s, 3H).

Example 9

3-(5-cyano-4-((2-methoxyethyl) amino) pyrid-2-yl)-1-(6-formyl-5-((3-carbonylmorpholino) methyl) pyrid-2-yl)-1-methylurea

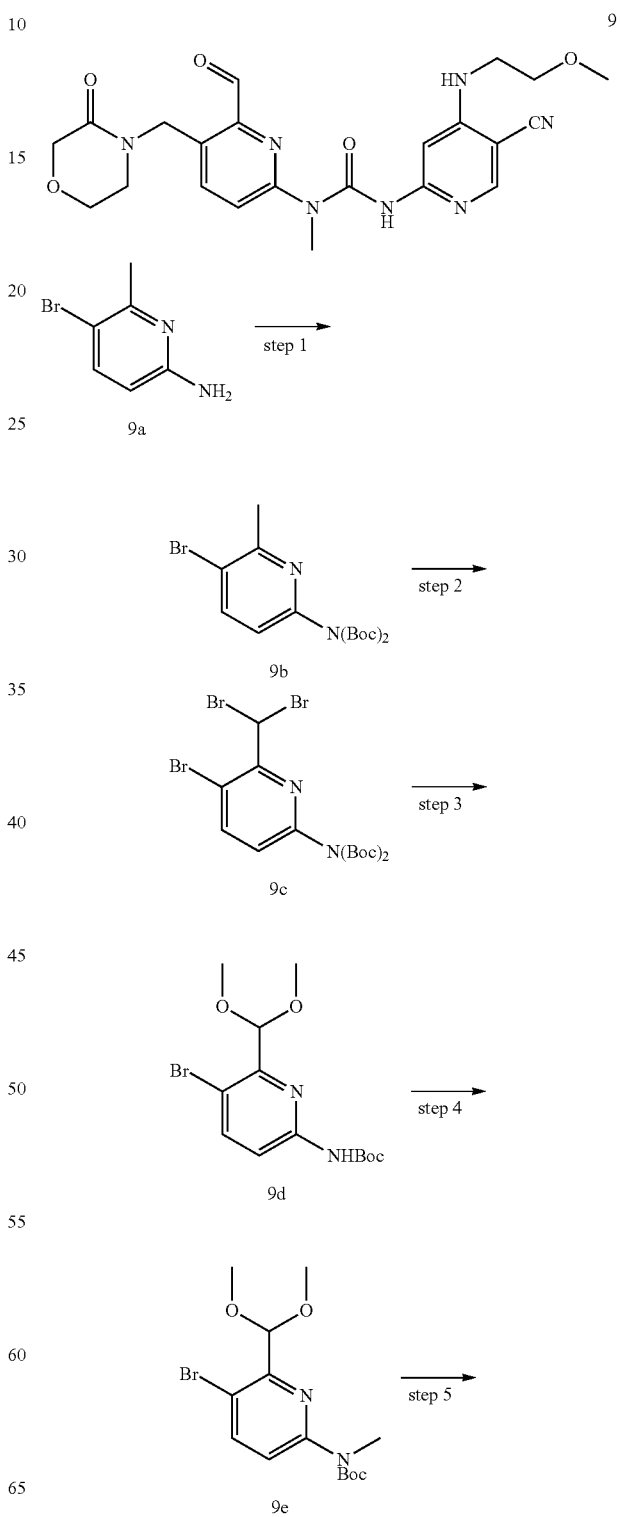

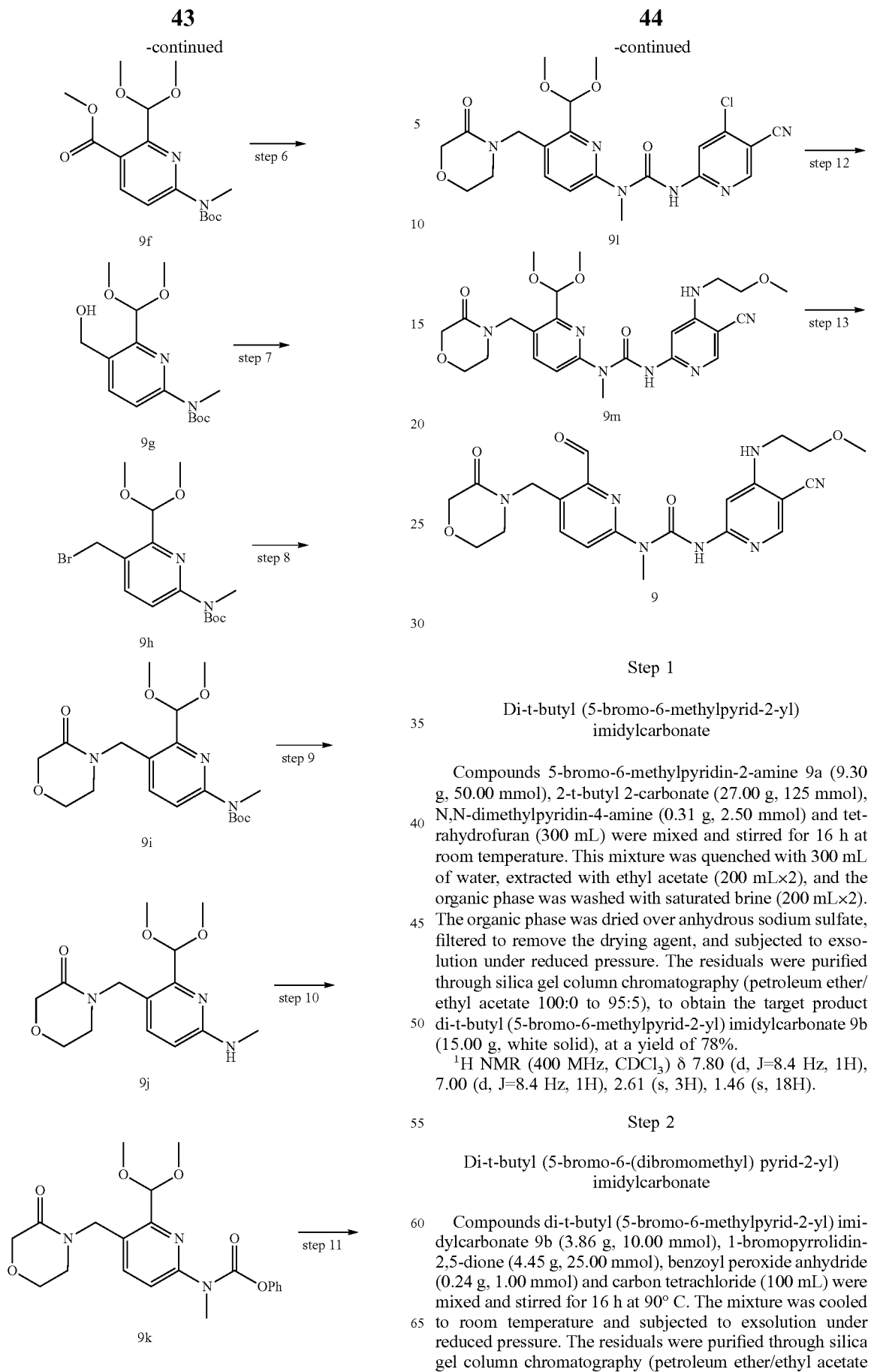

Step 1

Di-t-butyl (5-bromo-6-methylpyrid-2-yl) imidylcarbonate

Compounds 5-bromo-6-methylpyridin-2-amine 9a (9.30 g, 50.00 mmol), 2-t-butyl 2-carbonate (27.00 g, 125 mmol), N,N-dimethylpyridin-4-amine (0.31 g, 2.50 mmol) and tetrahydrofuran (300 mL) were mixed and stirred for 16 h at room temperature. This mixture was quenched with 300 mL of water, extracted with ethyl acetate (200 mL×2), and the organic phase was washed with saturated brine (200 mL×2). The organic phase was dried over anhydrous sodium sulfate, filtered to remove the drying agent, and subjected to exsolution under reduced pressure. The residuals were purified through silica gel column chromatography (petroleum ether/ethyl acetate 100:0 to 95:5), to obtain the target product di-t-butyl (5-bromo-6-methylpyrid-2-yl) imidylcarbonate 9b (15.00 g, white solid), at a yield of 78%.

$^1$H NMR (400 MHz, CDCl$_3$) δ 7.80 (d, J=8.4 Hz, 1H), 7.00 (d, J=8.4 Hz, 1H), 2.61 (s, 3H), 1.46 (s, 18H).

Step 2

Di-t-butyl (5-bromo-6-(dibromomethyl) pyrid-2-yl) imidylcarbonate

Compounds di-t-butyl (5-bromo-6-methylpyrid-2-yl) imidylcarbonate 9b (3.86 g, 10.00 mmol), 1-bromopyrrolidin-2,5-dione (4.45 g, 25.00 mmol), benzoyl peroxide anhydride (0.24 g, 1.00 mmol) and carbon tetrachloride (100 mL) were mixed and stirred for 16 h at 90° C. The mixture was cooled to room temperature and subjected to exsolution under reduced pressure. The residuals were purified through silica gel column chromatography (petroleum ether/ethyl acetate 94:6), to obtain a target product di-t-butyl (5-bromo-6-(dibromomethyl) pyrid-2-yl) imidylcarbonate 9c (4.00 g, yellow solid), at a yield of 74%.

$^1$H NMR (400 MHz, CDCl$_3$) δ 7.82 (d, J=8.0 Hz, 1H), 7.26 (d, J=8.0 Hz, 1H), 7.08 (s, 1H), 1.50 (s, 18H).

Step 3 t-butyl (5-bromo-6-(dimethoxy) pyrid-2-yl) aminocarboxylate

Compounds di-t-butyl (5-bromo-6-(dibromomethyl) pyrid-2-yl) imidylcarbonate 9c (5.00 g, 96.00 mmol), potassium hydroxide (2.23 g, 0.38 mol) and methanol (30 mL) were mixed and stirred for 16 h at 70° C. The mixture was cooled to room temperature, and subjected to exsolution under reduced pressure. The residuals were dissolved with 50 mL of water, extracted with ethyl acetate (50 mL×3), and the organic phase was washed with saturated brine (50 mL×2). The organic phase was dried over anhydrous sodium sulfate, filtered to remove the drying agent, and subjected to exsolution under reduced pressure. The residuals were purified through silica gel column chromatography (petroleum ether/ethyl acetate 100:0 to 12:1), to obtain the target product t-butyl (5-bromo-6-(dimethoxy) pyrid-2-yl) aminocarboxylate 9 d (0.50 g, yellow solid), at a yield of 16%.

MS m/z (ESI): 347 & 349 [M+1].

Step 4 t-butyl (5-bromo-6-(dimethoxy)pyrid-2-yl)(methyl) aminocarboxylate

Compounds t-butyl (5-bromo-6-(dimethoxy) pyrid-2-yl) aminocarboxylate 9 d (1.20 g, 3.47 mmol), sodium hydride (0.18 g, 4.51 mmol, 60% mineral oil mixture), iodomethane (0.59 g, 4.16 mmol) and N,N-dimethyl formamide (8 mL) were mixed, and stirred for 16 h at room temperature. This mixture was quenched with 30 mL of water, extracted with ethyl acetate (50 mL×3), and the organic phase was washed with saturated brine (50 mL×3). The organic phase was dried over anhydrous sodium sulfate, filtered to remove the drying agent, and subjected to exsolution under reduced pressure. The residuals were purified through silica gel column chromatography (petroleum ether/ethyl acetate 100:0 to 96:4), to obtain the target product t-butyl (5-bromo-6-(dimethoxy) pyrid-2-yl)(methyl) aminocarboxylate 9e (0.40 g, yellow oil), at a yield of 32%.

MS m/z (ESI): 361 & 363 [M+1].

Step 5

Methyl-6-((t-butoxy carbonyl)(methyl)amino)-2-(dimethoxymethyl) nicotinate

Compounds t-butyl (5-bromo-6-(dimethoxy) pyrid-2-yl) (methyl) aminocarboxylate 9e (0.45 g, 1.25 mmol), palladium acetate (28 mg, 0.13 mmol), 1,1-bis(diphenylphosphine) ferrocene (0.14 g, 0.25 mmol), triethyl amine (0.25 g, 2.50 mmol), methanol (3 mL) and N,N-dimethyl formamide (20 mL) were mixed and stirred for 16 h at 100° C. in a carbon monoxide atmosphere (1 atm). This mixture was quenched with 100 mL of water, extracted with ethyl acetate (50 mL×3), and the organic phase was washed with saturated brine (50 mL×3). The organic phase was dried over anhydrous sodium sulfate, filtered to remove the drying agent, and subjected to exsolution under reduced pressure. The residuals were purified through silica gel column chromatography (petroleum ether/ethyl acetate 96:4), to obtain the target product methyl-6-((t-butoxycarbonyl)(methyl) amino)-2-(dimethoxymethyl) nicotinate 9f (0.25 g, yellow oil), at a yield of 59%.

MS m/z (ESI): 341 [M+1]

$^1$H NMR (400 MHz, CDCl$_3$) δ 8.07 (d, J=8.8 Hz, 1H), 7.84 (d, J=8.8 Hz, 1H), 6.08 (s, 1H), 3.91 (s, 3H), 3.52 (s, 6H), 3.41 (s, 3H), 1.53 (s, 9H).

Step 6 t-butyl (6-(dimethoxymethyl)-5-(hydroxymethyl) pyrid-2-yl)(methyl) aminocarboxylate Compounds methyl-6-((t-butoxycarbonyl)(methyl) amino)-2-(dimethoxymethyl) nicotinate 9f (0.30 g, 0.88 mmol), sodium borohydride (0.67 g, 17.65 mmol), anhydrous calcium chloride (0.19 g, 1.77 mmol) and methanol (10 mL) were mixed and stirred for 8 h at 65° C. This mixture was quenched with 10 mL of water, extracted with ethyl acetate (50 mL×2), and the organic phase was washed with saturated brine (50 mL×2). The organic phase was dried over anhydrous sodium sulfate, filtered to remove the drying agent, and subjected to exsolution under reduced to pressure, to obtain the target product t-butyl (6-(dimethoxymethyl)-5-(hydroxymethyl) pyrid-2-yl)(methyl) aminocarboxylate 9g (0.20 g, white solid), at a yield of 73%.

MS m/z (ESI): 313 [M+1].

Step 7 t-butyl (5-(bromomethyl)-6-(dimethoxymethylpyrid-2-yl)(methyl) aminocarboxylate

Compounds t-butyl (6-(dimethoxymethyl)-5-(hydroxymethyl) pyrid-2-yl)(methyl) aminocarboxylate 9g (0.20 g, 0.64 mmol), phosphorus tribromide (0.21 g, 0.77 mmol) and dichloromethane (5 mL) were mixed and stirred for 1 h at 0° C. This mixture was quenched with 10 mL of an aqueous sodium bicarbonate solution, extracted with ethyl acetate (50 mL×2), and the organic phase was washed with saturated brine (50 mL×2). The organic phase was dried over anhydrous sodium sulfate, and filtered to remove the drying agent. The residuals were purified through silica gel column chromatography (petroleum ether/ethyl acetate 100:0 to 93:7), to obtain the target product t-butyl (5-(bromomethyl)-6-(dimethoxymethylpyrid-2-yl)(methyl) aminocarboxylate 9 h (0.15 g, colorless solid), at a yield of 63%.

MS m/z (ESI): 375 & 377 [M+1].

Step 8 t-butyl-(6-(2-methoxyethyl)-5((3-carbonylmorpholine) methyl) pyrid-2-yl)(methyl) aminocarboxylate Compounds t-butyl (5-(bromomethyl)-6-(dimethoxymethylpyrid-2-yl)(methyl) aminocarboxylate 9 h (70 mg, 0.19 mmol), morpholin-3-one (38 mg, 0.38 mmol), sodium hydride (19 mg, 0.47 mmol, 60% mineral oil mixture) and N,N-dimethyl formamide (3 mL) were mixed, and stirred for 1 h at room temperature. This mixture was quenched with water, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1.5:1), to obtain the target product t-butyl-(6-(2-methoxyethyl)-5-((3-carbonylmorpholine) methyl) pyrid-2-yl)(methyl) aminocarboxylate 9i (70 mg, white solid), at a yield of 95%.

MS m/z (ESI): 396 [M+1]

$^1$H NMR (400 MHz, CDCl$_3$) δ 7.63-7.61 (m, 2H), 5.22 (s, 1H), 4.91 (s, 2H), 4.26 (s, 2H), 3.82-3.81 (m, 2H), 3.45 (s, 6H), 3.40 (s, 3H), 3.27-3.26 (m, 2H), 1.52 (s, 9H).

Step 9

4-((2-(dimethoxymethyl)-6-(methylamino) pyrid-3-yl)methyl) morpholin-3-one

Compounds t-butyl-(6-(2-methoxyethyl)-5-((3-carbonylmorpholine)methyl) pyrid-2-yl)(methyl) aminocarboxylate 9i (70 mg, 0.18 mmol), trifluoroacetic acid (1 mL) and dichloromethane (4 mL) were mixed, and stirred for 6 h at room temperature. The mixture was alkalified with triethyl amine, and subjected to exsolution under reduced pressure. The residuals were purified through a preparative silica gel plate (petroleum ether/ethyl acetate 1:1), to obtain the target product 4-((2-(dimethoxymethyl)-6-(methylamino) pyrid-3-yl) methyl) morpholin-3-one 9j (46 mg, colorless solid), at a yield of 86%.

MS m/z (ESI): 296 [M+1].

Step 10

Phenyl-(6-(dimethoxymethyl)-5-((3-carbonylmorpholine) methyl) pyrid-2-yl)(methyl) aminocarboxylate Compounds 4-((2-(dimethoxymethyl)-6-(methylamino) pyrid-3-yl) methyl) morpholin-3-one 9j (60 mg, 0.20 mmol), diphenyl carbonate (87 mg, 0.40 mmol), lithium hexamethyldisilazide (1.0 mL, 1.01 mmol, 1 M solution in tetrahydrofuran) and tetrahydrofuran (5 mL) were mixed and stirred for 0.5 h at 0° C. This mixture was quenched with 10 mL of a saturated ammonium chloride solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 2:1), to obtain the target product phenyl (6-(dimethoxymethyl)-5-((3-carbonylmorpholine)methyl) pyrid-2-yl)(methyl) aminocarboxylate 9k (45 mg, colorless oil), at a yield of 54%.

MS m/z (ESI): 416 [M+1].

Step 11

3-(4-chloro-5-cyanopyrid-2-yl)-1-(6-(dimethoxymethyl)-5-((3-carbonylmorpholine) methyl) pyrid-2-yl)-1-methylurea Compounds phenyl (6-(dimethoxymethyl)-5-((3-carbonylmorpholine)methyl) pyrid-2-yl)(methyl) aminocarboxylate 9k (45 mg, 0.11 mmol), 6-amino-4-chloronicotinonitrile (33 mg, 0.22 mmol), lithium hexamethyldisilazide (0.3 mL, 0.33 mmol, 1 M solution in tetrahydrofuran) and tetrahydrofuran (3 mL) were mixed, and stirred for 1 h at room temperature. This mixture was quenched with 10 mL of a saturated ammonium chloride solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1:1), to obtain the target product 3-(4-chloro-5-cyanopyrid-2-yl)-1-(6-(dimethoxymethyl)-5-((3-carbonylmorpholine) methyl) pyrid-2-yl)-1-methylurea 9l (40 mg, white solid), at a yield of 78%.

MS m/z (ESI): 475 & 477 [M+1].

Step 12

3-(5-cyano-4-((2-methoxyethyl)amino)pyrid-2-yl)-1-(6-(dimethoxymethyl)-5-((3-carbonylmorpholine) methyl) pyrid-2-yl)-1-methylurea Compounds 3-(4-chloro-5-cyanopyrid-2-yl)-1-(6-(dimethoxymethyl)-5-((3-carbonylmorpholine)methyl) pyrid-2-yl)-1-methylurea 9l (20 mg, 0.04 mmol), 2-methoxy ethylamine (13 mg, 0.17 mmol), diisopropyl ethylamine (11 mg, 0.08 mmol) and N,N-dimethyl acetamide (0.4 mL) were mixed and stirred for 16 h at 50° C. This mixture was quenched with 10 mL of water, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1:1), to obtain the target product 3-(5-cyano-4-((2-methoxyethyl)amino) pyrid-2-yl)-1-(6-(dimethoxymethyl)-5-((3-carbonylmorpholine) methyl) pyrid-2-yl)-1-methylurea 9m (15 mg, white solid), at a yield of 69%.

MS m/z (ESI): 514 [M+1].

Step 13

3-(5-cyano-4-((2-methoxyethyl)amino) pyrid-2-yl)-1-(6-formyl-5-((3-carbonylmorpholine) methyl) pyrid-2-yl)-1-methylurea Compounds 3-(5-cyano-4-((2-methoxyethyl)amino) pyrid-2-yl)-1-(6-(dimethoxymethyl)-5-((3-carbonylmorpholine) methyl) pyrid-2-yl)-1-methylurea 9 m (15 mg, 0.03 mmol), hydrochloric acid (0.8 mL, 37%), water (1 mL) and tetrahydrofuran (2 mL) were mixed, and stirred for 1 h at room temperature. This mixture was quenched with a saturated sodium carbonate solution, extracted with dichloromethane (20 mL×2), and the organic phase was washed with saturated brine (20 mL×2). The organic phase was dried over anhydrous sodium sulfate, and filtered to remove the drying agent. The residuals were washed with ethyl acetate, to obtain the target product 3-(5-cyano-4-((2-methoxyethyl) amino) pyrid-2-yl)-1-(6-formyl-5-((3-carbonylmorpholine) methyl) pyrid-2-yl)-1-methylurea 9 (7 mg, white solid), at a yield of 52%.

MS m/z (ESI): 468 [M+1]

$^1$H NMR (400 MHz, CDCl$_3$) δ 12.99 (s, 1H), 10.26 (s, 1H), 8.17 (s, 1H), 7.98 (d, J=8.4 Hz, 1H), 7.56 (s, 1H), 7.27 (d, J=8.4 Hz, 1H), 5.31 (brs, 1H), 5.13 (s, 2H), 4.26 (s, 2H), 3.89 (t, J=4.4 Hz, 2H), 3.61 (t, J=4.0 Hz, 2H), 3.53 (s, 3H), 3.51 (t, J=4.4 Hz, 2H), 3.42 (s, 3H), 3.41 (d, J=4.0 Hz, 2H).

Example 10
3-(5-cyano-4-(isopropylamino) pyrid-2-yl)-1-(6-formyl-5-((3-carbonylmorpholino) methyl) pyrid-2-yl)-1-methylurea
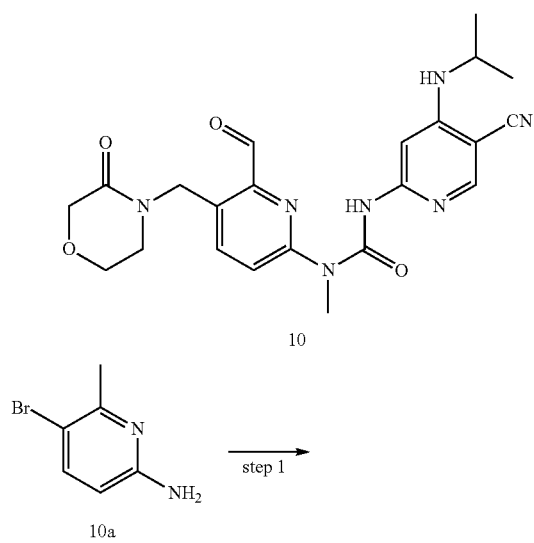
10
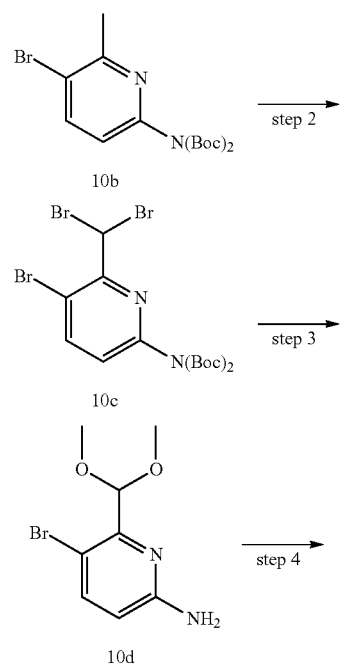
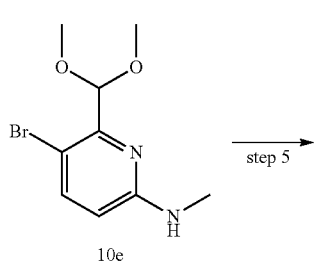
-continued
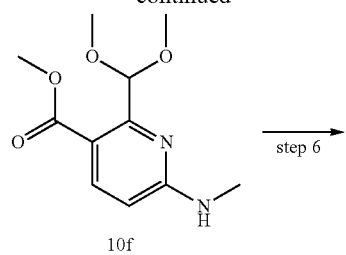
10f
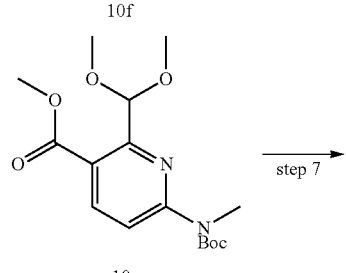
10g
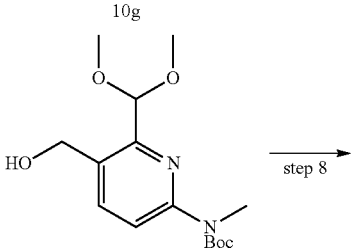
10h
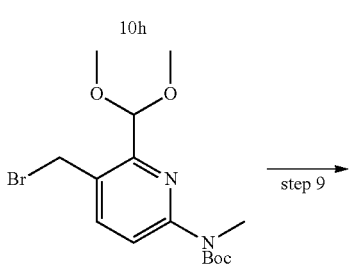
10i
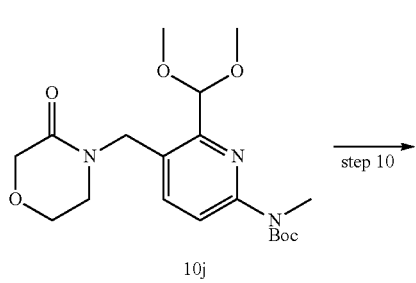
10j
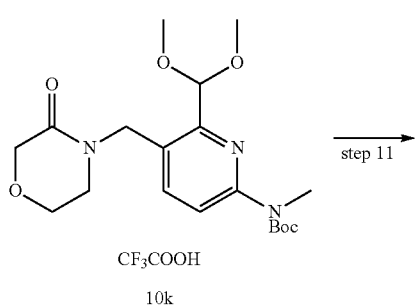
10k

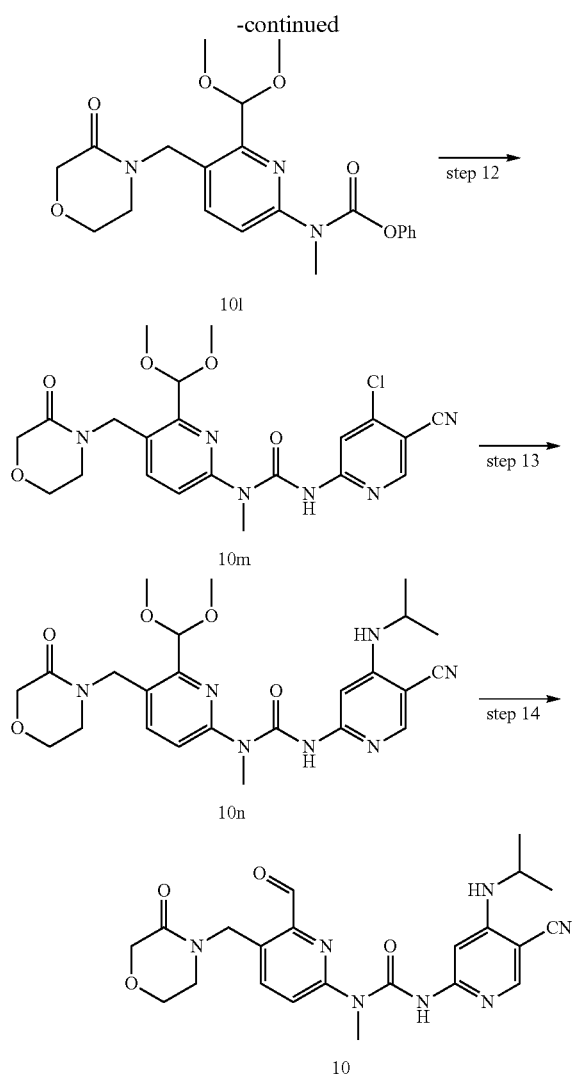

Step 1 di-t-butyl (5-bromo-6-methylpyrid-2-yl) imidylcarbonate

Compounds 5-bromo-6-methylpyridin-2-amine 10a (50 g, 0.27 mol), 2-t-butyl 2-carbonate (145.16 g, 0.67 mol), N,N-dimethylpyridin-4-amine (3.20 g, 27.00 mmol) and tetrahydrofuran (300 mL) were mixed and stirred for 16 h at room temperature. This mixture was quenched with 300 mL of water, extracted with ethyl acetate (200 mL×2), and the organic phase was washed with saturated brine (200 mL×2). The organic phase was dried over anhydrous sodium sulfate, filtered to remove the drying agent, and subjected to exsolution under reduced pressure. The residuals were washed with petroleum ether, to obtain the target product di-t-butyl (5-bromo-6-methylpyrid-2-yl) imidylcarbonate 10b (80.00 g, white solid), at a yield of 77%.

$^1$H NMR (400 MHz, CDCl$_3$) δ 7.80 (d, J=8.4, 1H), 7.00 (d, J=8.4 Hz, 1H), 2.61 (s, 3H), 1.46 (s, 18H).

Step 2 di-t-butyl (5-bromo-6-(dibromomethyl) pyrid-2-yl) imidylcarbonate

Compounds di-t-butyl (5-bromo-6-methylpyrid-2-yl) imidylcarbonate 10b (80 g, 0.21 mol), 1-bromopyrrolidin-2,5-dione (110.00 g, 0.63 mol), benzoyl peroxide anhydride (0.24 g, 0.06 mol) and carbon tetrachloride (600 mL) were mixed and stirred for 16 h at 90° C. The mixture was cooled to room temperature and subjected to exsolution under reduced pressure. The residuals were purified through silica gel column chromatography (petroleum ether/ethyl acetate 94:6), to obtain the target product di-t-butyl (5-bromo-6-(dibromomethyl) pyrid-2-yl) imidylcarbonate 10c (90.00 g, yellow solid), at a yield of 80%.

$^1$H NMR (400 MHz, CDCl$_3$) δ 7.82 (d, J=8.0 Hz, 1H), 7.26 (d, J=8.0 Hz, 1H), 7.08 (s, 1H), 1.50 (s, 18H).

Step 3

5-bromo-6-(dimethoxymethyl) pyridin-2-amine

Compounds di-t-butyl (5-bromo-6-(dibromomethyl) pyrid-2-yl) imidylcarbonate 10c (90.00 g, 0.17 mol), potassium hydroxide (38.52 g, 0.66 mol) and methanol (300 mL) were mixed and stirred for 72 h at 70° C. The mixture was cooled to room temperature, and subjected to exsolution under reduced pressure. The residuals were dissolved with 500 mL of water, extracted with ethyl acetate (500 mL×3), and the organic phase was washed with saturated brine (500 mL×2). The organic phase was dried over anhydrous sodium sulfate, filtered to remove the drying agent, and subjected to exsolution under reduced pressure. The residuals were purified through silica gel column chromatography (petroleum ether/ethyl acetate 100:0 to 12:1), to obtain the target product 5-bromo-6-(dimethoxymethyl) pyridin-2-amine 10 d (22 g, yellow solid), at a yield of 54%.

MS m/z (ESI): 247 & 249 [M+1]

$^1$H NMR (400 MHz, CDCl$_3$) δ 7.54 (d, J=8.4 Hz, 1H), 6.38 (d, J=8.4 Hz, 1H), 5.61 (s, 1H), 4.63 (brs, 2H), 3.48 (s, 6H).

Step 4

5-bromo-6-(dimethoxymethyl)-N-methylpyridin-2-amine

Compounds 5-bromo-6-(dimethoxymethyl) pyridin-2-amine 10 d (22.00 g, 89.43 mmol), sodium methoxide (24.15 g, 447 mmol), paraformaldehyde (10.74 g, 358 mmol) and methanol (300 mL) were mixed and stirred for 16 h at 80° C. The mixture was cooled, and sodium borohydride (13.59 g, 358 mmol) was added therein and stirred for 1 h at 80° C. This mixture was quenched with 300 mL of water, extracted with ethyl acetate (500 mL×3), and the organic phase was washed with saturated brine (500 mL×3). The organic phase was dried over anhydrous sodium sulfate, filtered to remove the drying agent, and subjected to exsolution under reduced pressure. The residuals were purified through silica gel column chromatography (petroleum ether/ethyl acetate 100:0 to 96:4), to obtain the target product 5-bromo-6-

(dimethoxymethyl)-N-methylpyridin-2-amine 10e (8.20 g, yellow solid), at a yield of 34%.

MS m/z (ESI): 261 & 263 [M+1]

$^1$H NMR (400 MHz, CDCl$_3$) δ 7.58 (d, J=8.8 Hz, 1H), 6.27 (d, J=8.8 Hz, 1H), 5.59 (s, 1H), 4.87 (brs, 1H), 3.48 (s, 6H), 2.87 (d, J=5.2 Hz, 3H).

Step 5 methyl-2-(dimethoxymethyl)-6-(methylamino) nicotinate

Compounds 5-bromo-6-(dimethoxymethyl)-N-methylpyridin-2-amine 10e (8.00 g, 30.77 mmol), palladium acetate (0.69 g, 3.08 mmol), 1,1-bis(diphenylphosphine)ferrocene (3.41 g, 6.16 mmol), triethyl amine (6.22 g, 61.54 mmol), methanol (30 mL) and N,N-dimethyl formamide (400 mL) were mixed and stirred for 16 h at 100° C. in a carbon monoxide atmosphere. This mixture was quenched with 700 mL of water, extracted with ethyl acetate (500 mL×3), and the organic phase was washed with saturated brine (500 mL×3). The organic phase was dried over anhydrous sodium sulfate, filtered to remove the drying agent, and subjected to exsolution under reduced pressure. The residuals were purified through silica gel column chromatography (petroleum ether/ethyl acetate 94:6), to obtain the target product methyl-2-(dimethoxymethyl)-6-(methylamino) nicotinate 10f (2.30 g, yellow solid), at a yield of 30%.

MS m/z (ESI): 241 [M+1]

$^1$H NMR (400 MHz, CDCl$_3$) δ 8.05 (d, J=8.8 Hz, 1H), 6.32 (d, J=8.8 Hz, 1H), 6.24 (s, 1H), 5.30 (brs, 1H), 3.86 (s, 3H), 3.51 (s, 6H), 2.95 (d, J=5.2 Hz, 3H).

Step 6

Methyl-6-((t-butoxycarbonyl)(methyl)amino)-2-(dimethoxymethyl) nicotinate

Compounds methyl-2-(dimethoxymethyl)-6-(methylamino) nicotinate 10f (2.00 g, 8.33 mmol), 2-t-butyl 2-carbonate (3.60 g, 16.67 mol), N,N-dimethylpyridin-4-amine (0.10 g, 0.83 mmol) and tetrahydrofuran (50 mL) were mixed, and stirred for 2 h at room temperature. This mixture was quenched with 100 mL of water, extracted with ethyl acetate (100 mL×3), and the organic phase was washed with saturated brine (100 mL×3). The organic phase was dried over anhydrous sodium sulfate, filtered to remove the drying agent, and subjected to exsolution under reduced pressure. The residuals were purified through silica gel column chromatography (petroleum ether/ethyl acetate 94:6), to obtain the target product methyl-6-((t-butoxycarbonyl)(methyl)amino)-2-(dimethoxymethyl) nicotinate 10g (2.20 g, yellow oil), at a yield of 78%.

MS m/z (ESI): 341 [M+1]

$^1$H NMR (400 MHz, CDCl$_3$) δ 8.07 (d, J=8.8 Hz, 1H), 7.84 (d, J=8.8 Hz, 1H), 6.08 (s, 1H), 3.91 (s, 3H), 3.52 (s, 6H), 3.49 (s, 3H), 1.53 (s, 9H).

Step 7 t-butyl (6-(dimethoxymethyl)-5-(hydroxymethyl) pyrid-2-yl)(methyl) aminocarboxylate Compounds methyl-6-((t-butoxycarbonyl)(methyl)amino)-2-(dimethoxymethyl) nicotinate 10g (2.20 g, 6.47 mmol), sodium borohydride (2.46 g, 60.47 mmol), anhydrous calcium chloride (1.42 g, 12.90 mmol) and methanol (20 mL) were mixed, and stirred for 2 h at 65° C. This mixture was quenched with 100 mL of water, extracted with ethyl acetate (100 mL×2), and the organic phase was washed with saturated brine (100 mL×2). The organic phase was dried over anhydrous sodium sulfate, filtered to remove the drying agent, and subjected to exsolution under reduced pressure, to obtain the target product t-butyl-(6-(dimethoxymethyl)-5-(hydroxymethyl) pyrid-2-yl)(methyl) aminocarboxylate 10 h (1.70 g, white solid), at a yield of 84%.

MS m/z (ESI): 313 [M+1].

Step 8 t-butyl (5-(bromomethyl)-6-(dimethoxymethylpyrid-2-yl)(methyl) aminocarboxylate Compounds t-butyl (6-(dimethoxymethyl)-5-(hydroxymethyl) pyrid-2-yl)(methyl) aminocarboxylate 10g (1.70 g, 5.45 mmol), phosphorus tribromide (1.75 g, 6.54 mmol) and dichloromethane (50 mL) were mixed and stirred for 0.5 h at 0° C. This mixture was quenched with 10 mL of an aqueous sodium bicarbonate solution, extracted with ethyl acetate (100 mL×2), and the organic phase was washed with saturated brine (100 mL×2). The organic phase was dried over anhydrous sodium sulfate, and filtered to remove the drying agent. The residuals were purified through silica gel column chromatography (petroleum ether/ethyl acetate 100:0 to 94:6), to obtain the target product t-butyl-(5-(bromomethyl)-6-(dimethoxymethylpyrid-2-yl)(methyl) aminocarboxylate 10i (0.80 g, colorless solid), at a yield of 40%.

MS m/z (ESI): 375 & 377 [M+1].

Step 9 t-butyl-(6-(2-methoxyethyl)-5-((3-carbonylmorpholine)methyl)pyrid-2-yl)(methyl) aminocarboxylate Compounds t-butyl-(5-(bromomethyl)-6-(dimethoxymethylpyrid-2-yl)(methyl) aminocarboxylate 10i (0.28 g, 0.76 mmol), morpholin-3-one (0.15 g, 1.52 mmol), sodium hydride (76 mg, 1.88 mmol, 60% mineral oil mixture) and N,N-dimethyl formamide (10 mL) were mixed, and stirred for 1 h at room temperature. This mixture was quenched with water, extracted with ethyl acetate (50 mL×3), and the organic phase was washed with saturated brine (50 mL×2). The organic phase was dried over anhydrous sodium sulfate, and filtered to remove the drying agent. The residuals were purified through silica gel column chromatography (petroleum ether/ethyl acetate=100:0 to 7:3), to obtain the target product t-butyl-(6-(2-methoxyethyl)-5-((3-carbonylmorpholine)methyl) pyrid-2-yl)(methyl) aminocarboxylate 10j (0.27 g, white solid), at a yield of 91%.

MS m/z (ESI): 396 [M+1].

Step 10

4-((2-(dimethoxymethyl)-6-(methylamino) pyrid-3-yl)methyl) morpholin-3-one

Compounds t-butyl-(6-(2-methoxyethyl)-5-((3-carbonylmorpholine)methyl) pyrid-2-yl)(methyl) aminocarboxylate 10j (0.27 g, 0.18 mmol), trifluoroacetic acid (1 mL) and dichloromethane (4 mL) were mixed, and stirred for 6 h at room temperature. The mixture was subjected to exsolution under reduced pressure, to obtain the target product 4-((2-

(dimethoxymethyl)-6-(methylamino) pyrid-3-yl)methyl) morpholin-3-one trifluoroacetate 10k (0.27 g, yellow solid).
MS m/z (ESI): 296 [M+1].

Step 11 phenyl-(6-(dimethoxymethyl)-5-((3-carbonylmorpholine) methyl) pyrid-2-yl)(methyl) aminocarboxylate Compounds 4-((2-(dimethoxymethyl)-6-(methylamino) pyrid-3-yl)methyl) morpholin-3-one trifluoroacetate 10k (0.25 g, 0.60 mmol), diphenyl carbonate (0.26 g, 1.20 mmol), lithium hexamethyldisilazide (1.8 mL, 1.80 mmol, 1 M solution in tetrahydrofuran) and tetrahydrofuran (8 mL) were mixed and stirred for 0.5 h at 0° C. This mixture was quenched with 10 mL of a saturated ammonium chloride solution, extracted with ethyl acetate (50 mL×2), and the organic phase was washed with saturated brine (50 mL×2). The organic phase was dried over anhydrous sodium sulfate, and filtered to remove the drying agent. The residuals were purified through a preparative silica gel plate (petroleum ether/ethyl acetate 2:1), to obtain the target product phenyl-(6-(dimethoxymethyl)-5-((3-carbonylmorpholine)methyl) pyrid-2-yl)(methyl) aminocarboxylate 10l (0.13 g, colorless oil), at a yield of 51%.
MS m/z (ESI): 416 [M+1].

Step 12

3-(4-chloro-5-cyanopyrid-2-yl)-1-(6-(dimethoxymethyl)-5-((3-carbonylmorpholine) methyl) pyrid-2-yl)-1-methylurea Compounds phenyl (6-(dimethoxymethyl)-5-((3-carbonylmorpholine)methyl) pyrid-2-yl)(methyl) aminocarboxylate 10l (45 mg, 0.11 mmol), 6-amino-4-chloronicotinonitrile (33 mg, 0.22 mmol), lithium hexamethyldisilazide (0.3 mL, 0.33 mmol, 1 M solution in tetrahydrofuran) and tetrahydrofuran (3 mL) were mixed, and stirred for 1 h at room temperature. This mixture was quenched with 10 mL of a saturated ammonium chloride solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1:1), to obtain the target product 3-(4-chloro-5-cyanopyrid-2-yl)-1-(6-(dimethoxymethyl)-5-((3-carbonylmorpholine)methyl) pyrid-2-yl)-1-methylurea 10m (38 mg, white solid), at a yield of 74%.
MS m/z (ESI): 475 & 477 [M+1].

Step 13

3-(5-cyano-4-(isopropylamino) pyrid-2-yl)-1-(6-(dimethoxymethyl)-5-((3-carbonylmorpholino) methyl) pyrid-2-yl)-1-methylurea Compounds 3-(4-chloro-5-cyanopyrid-2-yl)-1-(6-(dimethoxymethyl)-5-((3-carbonylmorpholine) methyl) pyrid-2-yl)-1-methylurea 10m (10 mg, 0.02 mmol), isopropyl amine (5 mg, 0.08 mmol), diisopropyl ethylamine (6 mg, 0.04 mmol) and N,N-dimethylacetamide (0.4 mL) were mixed and stirred for 16 h at 50° C. This mixture was quenched with 10 mL of water, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1:1), to obtain the target product 3-(5-cyano-4-(isopropylamino) pyrid-2-yl)-1-(6-(dimethoxymethyl)-5-((3-carbonylmorpholino) methyl) pyrid-2-yl)-1-methylurea 10n (5 mg, white solid), at a yield of 48%.
MS m/z (ESI): 498 [M+1].

Step 14

3-(5-cyano-4-(isopropylamino) pyrid-2-yl)-1-(6-formyl-5-((3-carbonylmorpholino) methyl) pyrid-2-yl)-1-methylurea Compounds 3-(5-cyano-4-(isopropylamino) pyrid-2-yl)-1-(6-(dimethoxymethyl)-5-((3-carbonylmorpholino)methyl) pyrid-2-yl)-1-methylurea 10n (5 mg, 0.01 mmol), hydrochloric acid (0.8 mL, 37%), water (1 mL) and tetrahydrofuran (2 mL) were mixed, and stirred for 1 h at room temperature. This mixture was quenched with a saturated sodium carbonate solution, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1:1), to obtain the target product 3-(5-cyano-4-(isopropylamino) pyrid-2-yl)-1-(6-formyl-5-((3-carbonylmorpholino)methyl) pyrid-2-yl)-1-methylurea 10 (3 mg, white solid), at a yield of 66%.
MS m/z (ESI): 452 [M+1]
$^1$H NMR (400 MHz, CDCl$_3$) δ 12.95 (s, 1H), 10.26 (s, 1H), 8.15 (s, 1H), 7.98 (d, J=8.8 Hz, 1H), 7.56 (s, 1H), 7.30 (d, J=8.8 Hz, 1H), 5.13 (s, 2H), 4.78-4.76 (m, 1H), 4.26 (s, 2H), 3.89 (t, J=4.4 Hz, 2H), 3.88 (brs, 1H), 3.53 (s, 3H), 3.43 (t, J=4.4 Hz, 2H), 1.31 (d, J=4.8 Hz, 6H).

Example 11

1-(4-chloro-5-cyanopyrid-2-yl)-3-(6-formyl-5-((3-carbonylmorpholine)methyl) pyrid-2-yl)urea

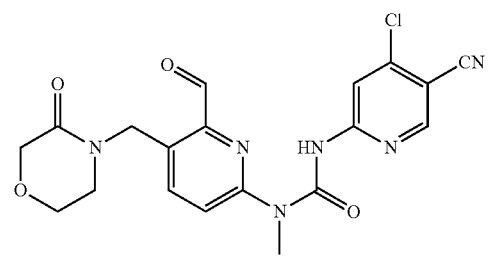

11

Example 11 was synthesized with reference to the operation steps of Example 9, except that 1-(4-chloro-5-cyanopyrid-2-yl)-3-(6-formyl-5-((3-carbonylmorpholine) methyl) pyrid-2-yl)urea was substituted for 3-(5-cyano-4-((2-methoxyethyl)amino) pyrid-2-yl)-1-(6-(dimethoxymethyl)-5-((3-carbonylmorpholino) methyl) pyrid-2-yl)-1-methylurea in Step 13.
MS m/z (ESI): 429 & 431 [M+1]
$^1$H NMR (400 MHz, CDCl$_3$) δ 13.60 (s, 1H), 10.26 (s, 1H), 8.51 (s, 1H), 8.46 (s, 1H), 8.01 (d, J=8.8 Hz, 1H), 7.28

(d, J=8.8 Hz, 1H), 5.13 (s, 2H), 4.26 (s, 2H), 3.91 (t, J=3.2 Hz, 2H), 3.55 (s, 3H), 3.44 (t, J=3.2 Hz, 2H).

Example 12

1-(5-cyano-4-(2-methoxyethoxy) pyrid-2-yl)-3-(6-formyl-5-((3-carbonylmorpholino) methyl) pyrid-2-yl)urea

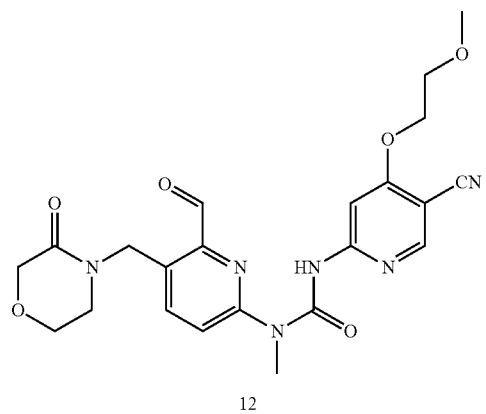

12

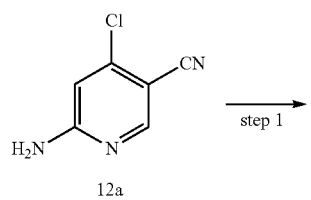

12a step 1 →

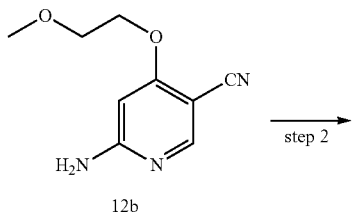

12b step 2 →

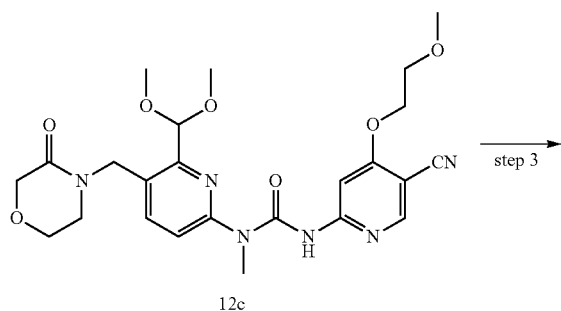

12c step 3 →

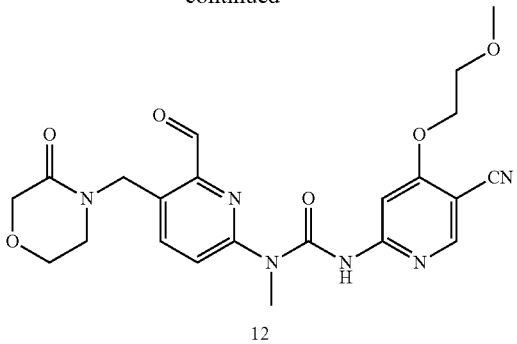

12

Step 1

6-amino-4-(2-methoxyethoxy) nicotinonitrile

Compounds 6-amino-4-chloronicotinonitrile 12a (60 mg, 0.39 mmol), 2-methoxy ethanol (60 mg, 0.78 mmol), sodium hydride (34 mg, 0.86 mmol, 60% mineral oil mixture) and N-methylpyrrolidone (1.5 mL) were mixed and stirred for 16 h at 70° C. The mixture was cooled to room temperature, and this mixture was quenched with 20 mL of water, extracted with ethyl acetate (20 mL×2), and the organic phase was washed with saturated brine (20 mL×2). The organic phase was dried over anhydrous sodium sulfate, filtered to remove the drying agent, and subjected to exsolution under reduced pressure. The residuals were purified through a preparative silica gel plate (petroleum ether/ethyl acetate=1:1), to obtain the target product 6-amino-4-(2-methoxyethoxy) nicotinonitrile 12b (30 mg, white solid), at a yield of 40%.

MS m/z (ESI): 194 [M+1].

Step 2

3-(5-cyano-4-(2-methoxyethoxy) pyrid-2-yl)-1-(6-(dimethoxymethyl)-5-((3-carbonylmorpholine) methyl) pyrid-2-yl)-1-methylurea Example 12c was synthesized with reference to the operation steps in Step 11 of Example 9, except that 6-amino-4-(2-methoxyethoxy) nicotinonitrile was substituted for 6-amino-4-chloronicotinonitrile, to obtain the target product 3-(5-cyano-4-(2-methoxyethoxy) pyrid-2-yl)-1-(6-(dimethoxymethyl)-5-((3-carbonylmorpholino) methyl) pyrid-2-yl)-1-methylurea 12c (8 mg, white solid), at a yield of 70%.

MS m/z (ESI): 515 [M+1].

Step 3

3-(5-cyano-4-(2-methoxyethoxy) pyrid-2-yl)-1-(6-formyl-5-((3-carbonylmorpholine) methyl) pyrid-2-yl)-1-methylurea Example 12 was synthesized with reference to the operation steps in Step 13 of Example 9, except that 3-(5-cyano-4-(2-methoxyethoxy) pyrid-2-yl)-1-(6-(dimethoxymethyl)-5-((3-carbonylmorpholine)methyl) pyrid-2-yl)-1-methylurea was substituted for 3-(5-cyano-4-((2-methoxyethyl)amino) pyrid-2-yl)-1-(6-(dimethoxymethyl)-5-((3-carbonylmorpholine)methyl) pyrid-2-yl)-1-methylurea, to obtain the target product 3-(5-cyano-4- isopropoxypyrid-2-yl)-1-(6-formylpyrid-2-yl)-1-methylurea 12 (6 mg, white solid), at a yield of 82%.

MS m/z (ESI): 469 [M+1]

¹H NMR (400 MHz, CDCl₃) δ 13.34 (s, 1H), 10.27 (s, 1H), 8.36 (s, 1H), 8.00 (d, J=8.8 Hz, 1H), 7.96 (s, 1H), 7.18 (d, J=7.6 Hz, 1H), 5.13 (s, 2H), 4.35 (s, 2H), 4.26 (d, J=3.2 Hz, 2H), 3.90 (t, J=3.2 Hz, 2H), 3.83 (t, J=4.0 Hz, 2H), 3.54 (s, 3H), 3.38 (s, 3H), 3.43 (t, J=4.0 Hz, 2H).

Example 13

1-(5-cyano-4-isopropoxypyrid-2-yl)-3-(6-formyl-5-((3-carbonylmorpholine) methyl) pyrid-2-yl)urea

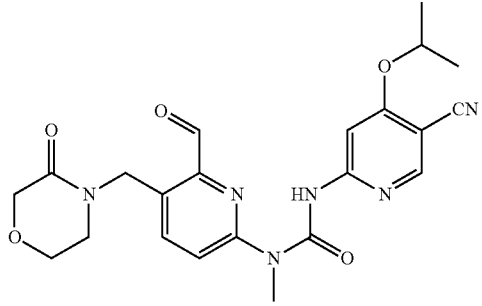

13

Example 13 was synthesized with reference to the operation steps of Example 12, except that isopropanol was substituted for 2-methoxy ethanol in Step 1.

MS m/z (ESI): 453 [M+1]

¹H NMR (400 MHz, CDCl₃) δ 13.26 (s, 1H), 10.27 (s, 1H), 8.34 (s, 1H), 8.00 (d, J=8.8 Hz, 1H), 7.93 (s, 1H), 7.32 (d, J=8.8 Hz, 1H), 5.13 (s, 2H), 4.87-4.85 (m, 1H), 4.26 (s, 2H), 3.54 (s, 3H), 3.47 (t, J=4.4 Hz, 2H), 3.43 (t, J=4.4 Hz, 2H), 1.45 (d, J=3.2 Hz, 6H).

Example 14

(R)-3-(5-cyano-4-((1-methoxyprop-2-yl)oxo) pyrid-2-yl)-1-(6-formyl-5-((3-carbonylmorpholino) methyl) pyrid-2-yl)-1-methylurea

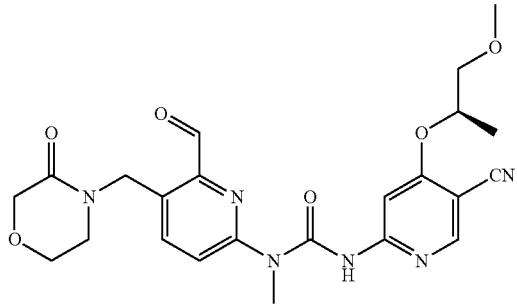

14

Example 14 was synthesized with reference to the operation steps of Example 12, except that (R)-1-methoxypropan-2-ol was substituted for 2-methoxy ethanol in Step 1.

MS m/z (ESI): 483 [M+1]

¹H NMR (400 MHz, CDCl₃) δ 13.27 (s, 1H), 10.26 (s, 1H), 8.34 (s, 1H), 7.99 (s, 1H), 7.98 (d, J=8.8 Hz, 1H), 7.32 (d, J=8.8 Hz, 1H), 5.13 (s, 2H), 4.87-4.86 (m, 1H), 4.26 (s, 2H), 3.90 (t, J=4.4 Hz, 2H), 3.64-3.60 (m, 1H), 3.56-3.55 (m, 1H), 3.54 (s, 3H), 3.49 (t, J=4.4 Hz, 2H), 3.43 (s, 3H), 1.43 (d, J=3.2 Hz, 3H).

Example 15

3-(5-cyano-4-((2-methoxyethyl)amino) pyrid-2-yl)-1-(6-formyl-5-((4-methyl-2-carbonylpiperazin-1-yl) methyl) pyrid-2-yl)-1-methylurea hydrochloride

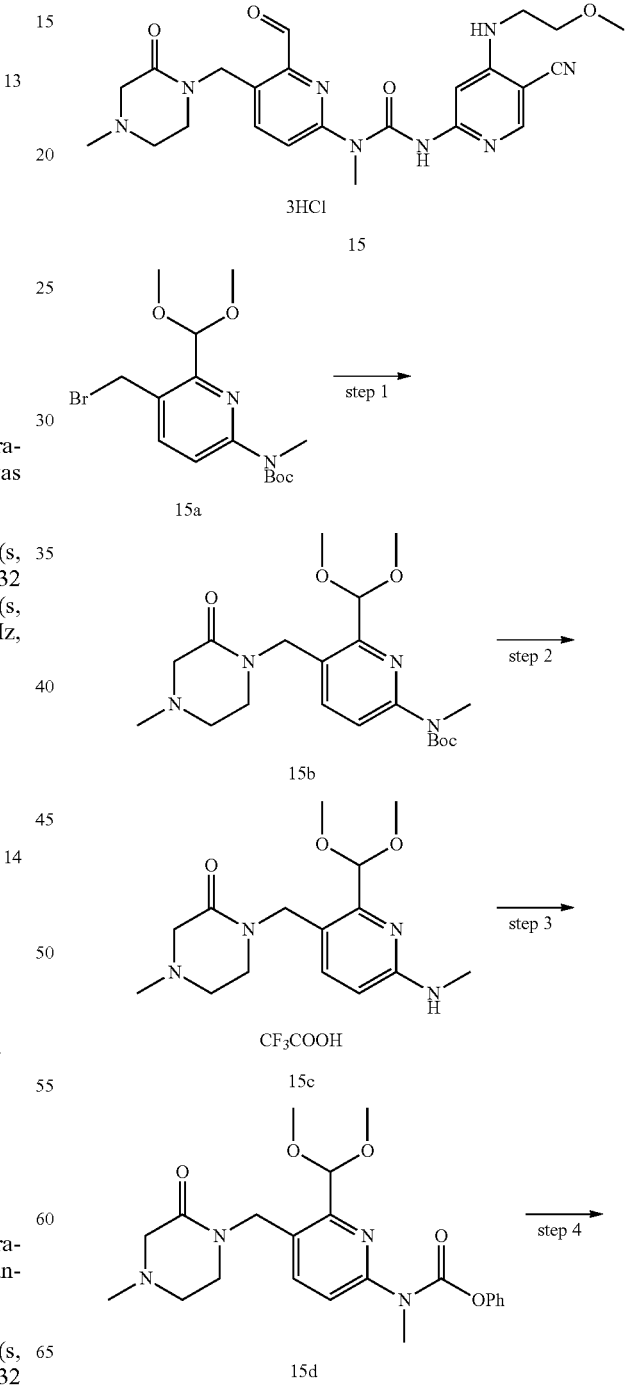

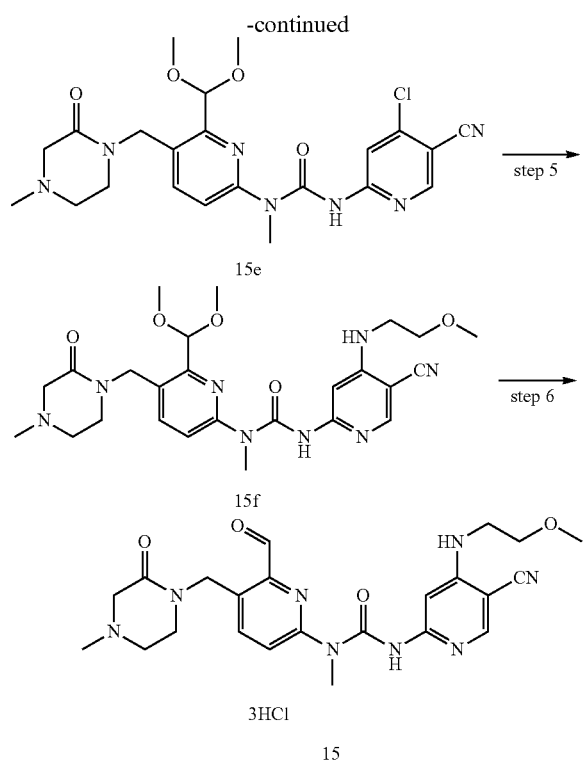

Step 1 t-butyl-(6-(dimethoxymethyl)-5-((4-methyl-2-carbo-nylpiperazin-1-yl)methyl) pyrid-2-yl)(methyl) amin-ocarboxylate Compounds t-butyl-(5-(bromomethyl)-6-(dimethoxy-ethylpyrid-2-yl)(methyl) aminocarboxylate 15a (70 mg, 0.19 mmol), 4-methylpiperazin-2-one (43 mg, 0.38 mmol), sodium hydride (19 mg, 0.47 mmol, 60% mineral oil mixture) and N,N-dimethyl formamide (3 mL) were mixed, and stirred for 1 h at room temperature. This mixture was quenched with water, extracted with dichloromethane (20 mL×3), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1.5:1), to obtain the target product t-butyl-(6-(dimethoxymethyl)-5-((4-methyl-2-carbonylpiperazin-1-yl)methyl) pyrid-2-yl)(methyl) aminocarboxylate 15b (60 mg, colorless solid), at a yield of 83%.

MS m/z (ESI): 409 [M+1].

Step 2

1-((2-(dimethoxymethyl)-6-(methylamino) pyrid-3-yl) methyl)-4-methylpiperazin-2-one Compounds t-butyl-(6-(dimethoxymethyl)-5-((4-methyl-2-carbonylpiperazin-1-yl)methyl) pyrid-2-yl)(methyl) aminocarboxylate 15b (60 mg, 0.15 mmol), trifluoroacetic acid (1 mL) and dichloromethane (4 mL) were mixed, and stirred for 6 h at room temperature. The mixture was subjected to exsolution under reduced pressure, to obtain the target product 1-((2-(dimethoxymethyl)-6-(methylamino) pyrid-3-yl) methyl)-4-methylpiperazin-2-one trifluoroacetate salt 15c (60 mg, light-yellow solid), as a crude product.

MS m/z (ESI): 309 [M+1].

Step 3

Phenyl-(6-(dimethoxymethyl)-5-((4-methyl-2-carbo-nylpiperazin-1-yl)methyl) pyrid-2-yl)(methyl) amin-ocarboxylate Compounds 1-((2-(dimethoxymethyl)-6-(methylamino) pyrid-3-yl) methyl)-4-methylpiperazin-2-one trifluoroac-etate salt 15c (60 mg, 0.14 mmol), diphenyl carbonate (60 mg, 0.28 mmol), lithium hexamethyldisilazide (0.56 mL, 0.56 mmol, 1 M solution in tetrahydrofuran) and tetrahy-drofuran (5 mL) were mixed and stirred for 0.5 h at 0° C. This mixture was quenched with 10 mL of a saturated ammonium chloride solution, extracted with dichlorometh-ane (20 mL×3), and the organic phase was washed with saturated brine (20 mL×2). The organic phase was dried over anhydrous sodium sulfate, and filtered to remove the drying agent. The residuals were purified through a preparative silica gel plate (dichloromethane/methanol 30:1), to obtain the target product phenyl-(6-(dimethoxymethyl)-5-((4-methyl-2-carbonylpiperazin-1-yl) methyl) pyrid-2-yl) (methyl) aminocarboxylate 15d (30 mg, colorless solid), at a yield of 36%.

MS m/z (ESI): 429 [M+1].

Step 4

3-(4-chloro-5-cyanopyrid-2-yl)-1-(6-(dimethoxym-ethyl)-5-((4-methyl-2-carbonylpiperazin-1-yl) methyl) pyrid-2-yl)-1-methylurea Compounds phenyl-(6-(dimethoxymethyl)-5-((4-methyl-2-carbonylpiperazin-1-yl) methyl) pyrid-2-yl)(methyl) aminocarboxylate 15d (30 mg, 0.07 mmol), 6-amino-4-chloronicotinonitrile (21 mg, 0.14 mmol), lithium hexam-ethyldisilazide (0.21 mL, 0.21 mmol, 1 M solution in tetrahydrofuran) and tetrahydrofuran (3 mL) were mixed, and stirred for 1 h at room temperature. This mixture was quenched with 10 mL of a saturated ammonium chloride solution, extracted with dichloromethane (20 mL×3), and the organic phase was washed with saturated brine (20 mL×2). The organic phase was dried over anhydrous sodium sulfate, and filtered to remove the drying agent. The residu-als were purified through a preparative silica gel plate (dichloromethane/methanol 30:1), to obtain the target prod-uct 3-(4-chloro-5-cyanopyrid-2-yl)-1-(6-(dimethoxym-ethyl)-5-((4-methyl-2-carbonylpiperazin-1-yl)methyl) pyrid-2-yl)-1-methylurea 15e (17 mg, white solid), at a yield of 50%.

MS m/z (ESI): 488 & 490 [M+1]

$^1$H NMR (400 MHz, CDCl$_3$) δ 13.82 (s, 1H), 8.52 (s, 1H), 8.46 (s, 1H), 7.77 (d, J=8.4 Hz, 1H), 7.04 (d, J=8.4 Hz, 1H), 5.47 (s, 1H), 4.86 (s, 2H), 3.47 (s, 6H), 3.46 (s, 3H), 3.27 (s, 2H), 3.20 (t, J=4.4 Hz, 2H), 2.62 (t, J=4.4 Hz, 2H), 2.35 (s, 3H).

Step 5

3-(5-cyano-4-((2-methoxyethyl)amino) pyrid-2-yl)-1-(6-(dimethoxymethyl)-5-((4-methyl-2-carbo-nylpiperazin-1-yl)methyl) pyrid-2-yl)-1-methylurea Compounds 3-(4-chloro-5-cyanopyrid-2-yl)-1-(6-(dime-thoxymethyl)-5-((4-methyl-2-carbonylpiperazin-1-yl)

methyl) pyrid-2-yl)-1-methylurea 15e (4 mg, 0.008 mmol), 2-methoxy ethylamine (2 mg, 0.024 mmol), diisopropyl ethylamine (2 mg, 0.016 mmol) and N,N-dimethylacetamide (0.4 mL) were mixed and stirred for 16 h at 50° C. This mixture was quenched with 10 mL of water, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 25:1), to obtain the target product 3-(5-cyano-4-((2-methoxyethyl)amino)pyrid-2-yl)-1-(6-(dimethoxymethyl)-5-((4-methyl-2-carbonylpiperazin-1-yl)methyl)pyrid-2-yl)-1-methylurea 15f (2 mg, white solid), at a yield of 46%.

MS m/z (ESI): 527 [M+1].

Step 6

3-(5-cyano-4-((2-methoxyethyl)amino) pyrid-2-yl)-1-(6-formyl-5-((4-methyl-2-carbonylpiperazin-1-yl) methyl) pyrid-2-yl)-1-methylurea hydrochloride Compounds 3-(5-cyano-4-((2-methoxyethyl)amino) pyrid-2-yl)-1-(6-(dimethoxymethyl)-5-((4-methyl-2-carbonylpiperazin-1-yl)methyl) pyrid-2-yl)-1-methylurea 15f (2 mg, 0.004 mmol), hydrochloric acid (0.8 mL, 37%), water (1 mL) and tetrahydrofuran (2 mL) were mixed, and stirred for 1 h at room temperature. The mixture was subjected to exsolution under reduced pressure, to obtain the target product 3-(5-cyano-4-((2-methoxyethyl)amino) pyrid-2-yl)-1-(6-formyl-5-((4-methyl-2-carbonylpiperazin-1-yl)methyl) pyrid-2-yl)-1-methylurea hydrochloride 15 (1.5 mg, white solid), at a yield of 67%.

MS m/z (ESI): 481 [M+1]
$^1$H NMR (400 MHz, CD$_3$OD) δ 8.40 (s, 1H), 7.98 (d, J=8.4 Hz, 1H), 7.40 (d, J=8.4 Hz, 1H), 6.94 (s, 1H), 6.92 (s, 1H), 4.91 (s, 2H), 3.75 (t, J=6.8 Hz, 2H), 3.69-3.60 (m, 2H), 3.45-3.42 (m, 4H), 3.37 (s, 3H), 3.36 (s, 3H), 3.26-3.21 (m, 2H), 3.03 (s, 3H).

Example 16

3-(5-cyano-4-(isopropylamino) pyrid-2-yl)-1-(6-formyl-5-((4-methyl-2-carbonylpiperazin-1-yl) methyl) pyrid-2-yl)-1-methylurea

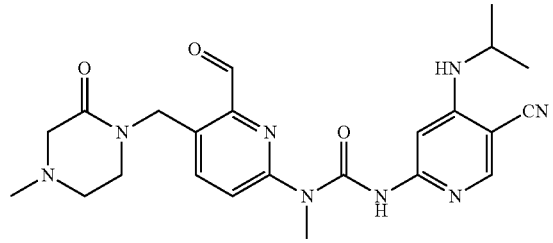

16

Example 16 was synthesized with reference to the operation steps of Example 15, except that isopropyl amine was substituted for 2-methoxy ethylamine in Step 5.

MS m/z (ESI): 465 [M+1]
$^1$H NMR (400 MHz, CDCl$_3$) δ 12.95 (s, 1H), 10.25 (s, 1H), 8.16 (s, 1H), 7.95 (d, J=8.0 Hz, 1H), 7.56 (s, 1H), 7.28 (d, J=8.0 Hz, 1H), 5.10 (s, 2H), 4.76 (brs, 1H), 3.89-3.87 (m, 1H), 3.52 (s, 3H), 3.36 (s, 2H), 3.20 (t, J=4.0 Hz, 2H), 2.66 (t, J=4.0 Hz, 2H), 2.35 (s, 3H), 1.32 (d, J=5.2 Hz, 6H).

Example 17

3-(4-chloro-5-cyanopyrid-2-yl)-1-(6-formyl-5-((4-methyl-2-carbonylpiperazin-1-yl) methyl) pyrid-2-yl)-1-methyl urea

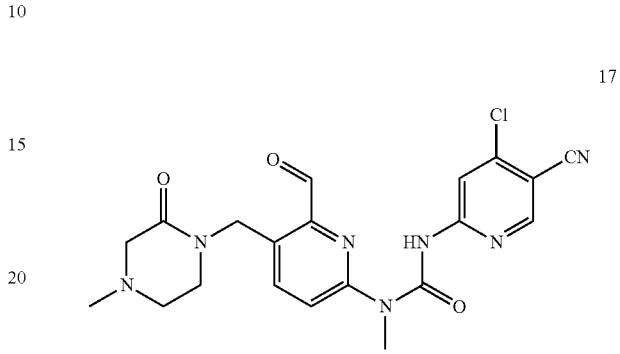

17

Example 17 was synthesized with reference to the operation steps of Example 15, except that 3-(4-chloro-5-cyano-pyrid-2-yl)-1-(6-(dimethoxymethyl)-5-((4-methyl-2-carbonylpiperazin-1-yl)methyl) pyrid-2-yl)-1-methylurea was substituted for 3-(5-cyano-4-((2-methoxyethyl)amino) pyrid-2-yl)-1-(6-(dimethoxymethyl)-5-((4-methyl-2-carbonylpiperazin-1-yl)methyl) pyrid-2-yl)-1-methylurea in Step 6.

MS m/z (ESI): 442 & 444 [M+1]
$^1$H NMR (400 MHz, CDCl$_3$) δ 13.59 (s, 1H), 10.26 (s, 1H), 8.51 (s, 1H), 8.46 (s, 1H), 7.95 (d, J=8.4 Hz, 1H), 7.31 (d, J=8.4 Hz, 1H), 5.10 (s, 2H), 3.54 (s, 3H), 3.38 (s, 2H), 3.20 (t, J=4.4 Hz, 2H), 2.68 (t, J=4.4 Hz, 2H), 2.36 (s, 3H).

Example 18

(R)-3-(5-cyano-4-((1-methoxyprop-2-yl)oxo) pyrid-2-yl)-1-(6-formyl-5-((4-methyl-2-carbonylpiperazin-1-yl)methyl) pyrid-2-yl)-1-methylurea

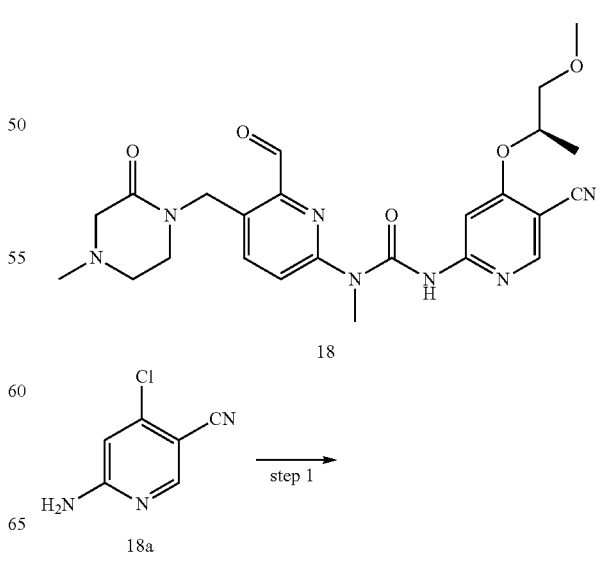

18

18a step 1

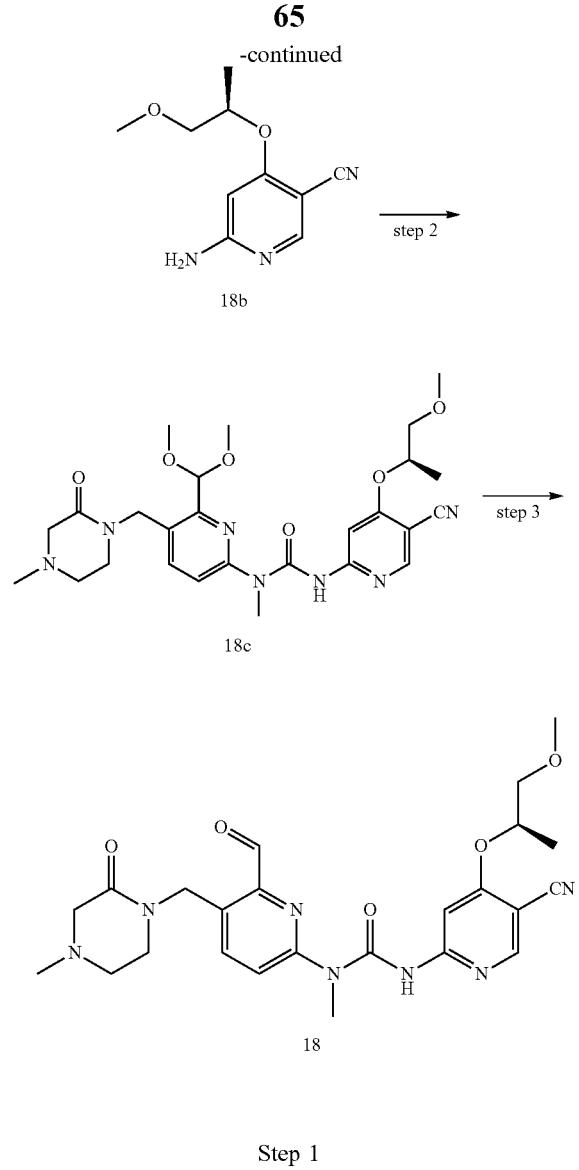

Step 1

(R)-6-amino-4-((1-methoxyprop-2-yl) oxo) nicotinonitrile

Compounds 6-amino-4-chloronicotinonitrile 18a (60 mg, 0.39 mmol), (R)-1-methoxypropan-2-ol (70 mg, 0.78 mmol), sodium hydride (34 mg, 0.86 mmol, 60% mineral oil mixture) and N-methylpyrrolidone (1.5 mL) were mixed and stirred for 16 h at 70° C. The mixture was cooled to room temperature, and this mixture was quenched with 20 mL of water, extracted with ethyl acetate (20 mL×2), and the organic phase was washed with saturated brine (20 mL×2). The organic phase was dried over anhydrous sodium sulfate, filtered to remove the drying agent, and subjected to exsolution under reduced pressure. The residuals were purified through a preparative silica gel plate (petroleum ether/ethyl acetate 1:1), to obtain the target product (R)-6-amino-4-((1-methoxyprop-2-yl)oxo) nicotinonitrile 18b (17 mg, white solid), at a yield of 21%.

MS m/z (ESI): 208 [M+1]

$^1$H NMR (400 MHz, CDCl$_3$) δ 8.17 (s, 1H), 6.00 (s, 1H), 4.94 (brs, 2H), 4.63-4.60 (m, 1H), 3.63-3.62 (m, 1H), 3.54-3.51 (m, 1H), 3.41 (s, 3H), 1.38-1.36 (m, 3H).

Step 2

(R)-3-(5-cyano-4-((1-methoxyprop-2-yl)oxo) pyrid-2-yl)-1-(6-(dimethoxymethyl)-5-((4-methyl-2-carbonylpiperazin-1-yl)methyl) pyrid-2-yl)-1-methylurea Compounds phenyl-(6-(dimethoxymethyl)-5-((4-methyl-2-carbonylpiperazin-1-yl)methyl) pyrid-2-yl)(methyl) aminocarboxylate (10 mg, 0.02 mmol), (R)-6-amino-4-((1-methoxyprop-2-yl) oxo) nicotinonitrile 18b (8 mg, 0.04 mmol), lithium hexamethyldisilazide (0.06 mL, 0.06 mmol, 1 M solution in tetrahydrofuran) and tetrahydrofuran (2 mL) were mixed, and stirred for 1 h at room temperature. This mixture was quenched with 10 mL of a saturated ammonium chloride solution, extracted with dichloromethane (20 mL×3), and the organic phase was washed with saturated brine (20 mL×2). The organic phase was dried over anhydrous sodium sulfate, and filtered to remove the drying agent. The residuals were purified through a preparative silica gel plate (dichloromethane/methanol 30:1), to obtain the target product (R)-3-(5-cyano-4-((1-methoxyprop-2-yl)oxo) pyrid-2-yl)-1-(6-(dimethoxymethyl)-5-((4-methyl-2-carbonylpiperazin-1-yl)methyl) pyrid-2-yl)-1-methylurea 18c (6 mg, white solid), at a yield of 47%.

MS m/z (ESI): 542 [M+1].

Step 3

(R)-3-(5-cyano-4-((1-methoxyprop-2-yl)oxo) pyrid-2-yl)-1-(6-formyl-5-((4-methyl-2-carbonylpiperazin-1-yl)methyl) pyrid-2-yl)-1-methylurea Compounds (R)-3-(5-cyano-4-((1-methoxyprop-2-yl) oxo) pyrid-2-yl)-1-(6-(dimethoxymethyl)-5-((4-methyl-2-carbonylpiperazin-1-yl)methyl) pyrid-2-yl)-1-methylurea 18c (6 mg, 0.01 mmol), hydrochloric acid (0.8 mL, 37%), water (1 mL) and tetrahydrofuran (2 mL) were mixed, and stirred for 1 h at room temperature. This mixture was quenched with a saturated sodium carbonate solution, extracted with dichloromethane (20 mL×2), and the organic phase was washed with saturated brine (20 mL×2). The organic phase was dried over anhydrous sodium sulfate, and filtered to remove the drying agent. The residuals were purified through a preparative silica gel plate (dichloromethane/methanol 25:1), to obtain the target product (R)-3-(5-cyano-4-((1-methoxyprop-2-yl)oxo) pyrid-2-yl)-1-(6-formyl-5-((4-methyl-2-carbonylpiperazin-1-yl)methyl) pyrid-2-yl)-1-methylurea 18 (4 mg, white solid), at a yield of 73%.

MS m/z (ESI): 496 [M+1]

$^1$H NMR (400 MHz, CDCl$_3$) δ 13.28 (s, 1H), 10.27 (s, 1H), 8.35 (s, 1H), 7.99 (s, 1H), 7.94 (d, J=7.6 Hz, 1H), 7.27 (d, J=7.6 Hz, 1H), 5.11 (s, 2H), 4.88-4.86 (m, 1H), 3.66-3.59 (m, 2H), 3.57 (s, 3H), 3.49 (s, 3H), 3.43 (s, 2H), 3.20 (t, J=4.4 Hz, 2H), 2.67 (t, J=4.4 Hz, 2H), 2.36 (s, 3H), 1.42-1.40 (m, 3H).

Example 19

3-(5-cyano-4-isopropoxypyrid-2-yl)-1-(6-formyl-5-((4-methyl-2-carbonylpiperazin-1-yl)methyl) pyrid-2-yl)-1-methylurea

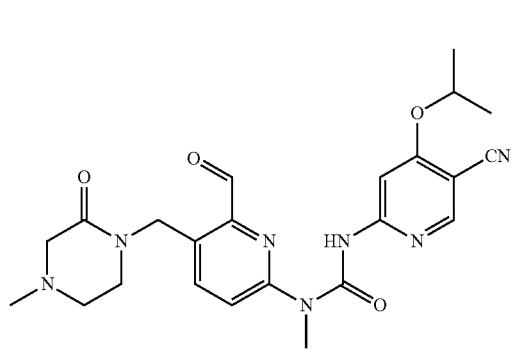

Example 19 was synthesized with reference to the operation steps of Example 18, except that isopropanol was substituted for (R)-1-methoxypropan-2-ol in Step 1.

MS m/z (ESI): 466 [M+1]

$^1$H NMR (400 MHz, CDCl$_3$) δ 13.28 (s, 1H), 10.26 (s, 1H), 8.34 (s, 1H), 7.96 (d, J=8.4 Hz, 1H), 7.93 (s, 1H), 7.26 (d, J=8.4 Hz, 1H), 5.10 (s, 2H), 4.85-4.83 (m, 1H), 3.49 (s, 3H), 3.38 (s, 2H), 3.21 (t, J=4.4 Hz, 2H), 2.69 (t, J=4.4 Hz, 2H), 2.36 (s, 3H), 1.45 (d, J=4.0 Hz, 6H).

Example 20

3-(5-cyano-4-(2-methoxyethoxy) pyrid-2-yl)-1-(6-formyl-5-((4-methyl-2-carbonylpiperazin-1-yl) methyl) pyrid-2-yl)-1-methylurea

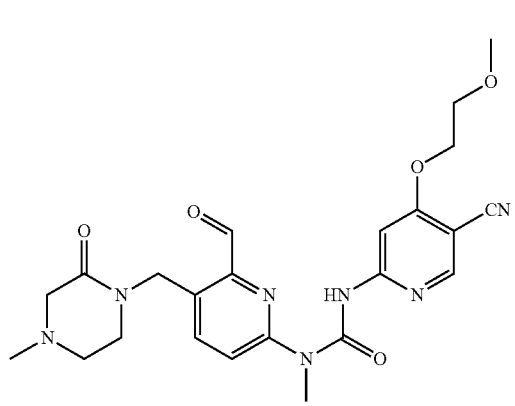

Example 20 was synthesized with reference to the operation steps of Example 18, except that 2-methoxy ethanol was substituted for (R)-1-methoxypropan-2-ol in Step 1.

MS m/z (ESI): 482 [M+1]

$^1$H NMR (400 MHz, CDCl$_3$) δ 13.34 (s, 1H), 10.27 (s, 1H), 8.36 (s, 1H), 7.96 (s, 1H), 7.95 (d, J=8.4 Hz, 1H), 7.31 (d, J=8.4 Hz, 1H), 5.11 (s, 2H), 4.35 (t, J=4.0 Hz, 2H), 3.83 (t, J=4.0 Hz, 2H), 3.53 (s, 3H), 3.48 (s, 3H), 3.37 (s, 2H), 3.20 (t, J=4.4 Hz, 2H), 2.67 (t, J=4.4 Hz, 2H), 2.36 (s, 3H).

Example 21

3-(5-cyano-4-((2-methoxyethyl)amino) pyrid-2-yl)-1-(6-formyl-5-(hydroxymethyl) pyrid-2-yl)-1-methylurea

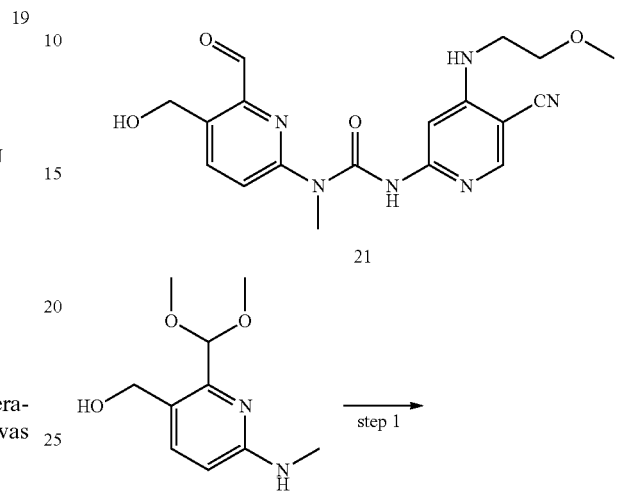

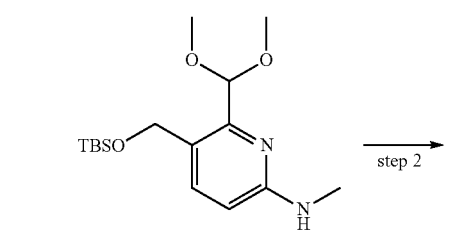

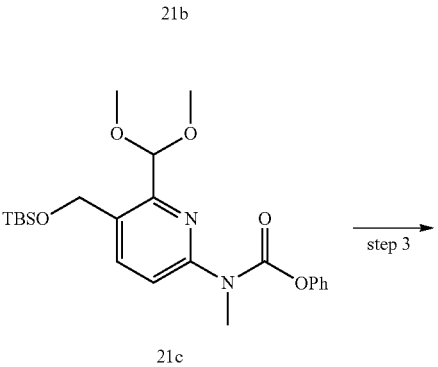

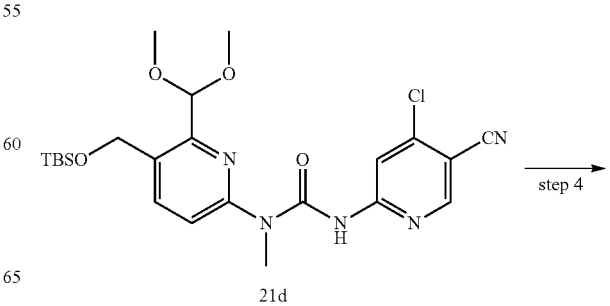

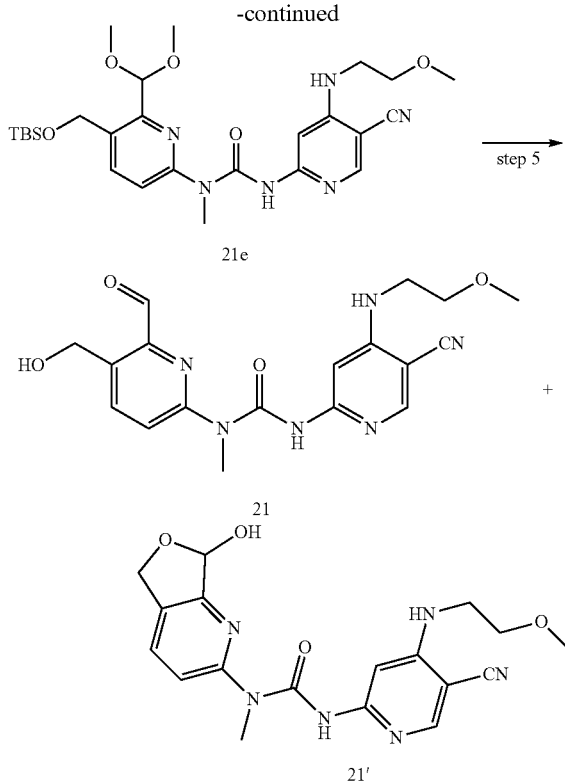

Step 1

5-(((t-butyldimethylsilyl) oxo)methyl)-6-(dimethoxymethyl)-N-methylpyridin-2-amine Compounds (2-(dimethoxymethyl)-6-(methylamino) pyrid-3-yl) methanol 21a (60 mg, 0.28 mmol), t-butyldimethylsilyl chloride (64 mg, 0.42 mmol), N-ethyl-N-isopropylpropan-2-amine (72 mg, 0.56 mmol), N,N-dimethylpyridin-4-amine (7 mg, 0.06 mmol) and dichloromethane (4 mL) were mixed, and stirred for 6 h at room temperature. This mixture was quenched with 20 mL of water, extracted with ethyl acetate (20 mL×2), and the organic phase was washed with saturated brine (20 mL×2). The organic phase was dried over anhydrous sodium sulfate, filtered to remove the drying agent, and subjected to exsolution under reduced pressure. The residuals were purified through a preparative silica gel plate (petroleum ether/ethyl acetate=15:1), to obtain the target product 5-(((t-butyldimethylsilyl)oxo)methyl)-6-(dimethoxymethyl)-N-methylpyridin-2-amine 21b (60 mg, colorless oil), at a yield of 65%.

MS m/z (ESI): 327 [M+1]

$^1$H NMR (400 MHz, CDCl$_3$) δ 7.57 (d, J=8.0 Hz, 1H), 6.28 (d, J=8.0 Hz, 1H), 5.21 (s, 1H), 4.69 (s, 2H), 4.57 (brs, 1H), 3.32 (s, 6H), 2.80 (s, 3H), 0.84 (s, 9H), 0.08 (s, 6H).

Step 2

Phenyl-(5-(((t-butyldimethylsilyl)oxo) methyl)-6-(dimethoxymethyl) pyrid-2-yl)(methyl) aminocarboxylate Compounds 5-(((t-butyldimethylsilyl) oxo)methyl)-6-(dimethoxymethyl)-N-methylpyridin-2-amine 21b (22 mg, 0.07 mmol), diphenyl carbonate (15 mg, 0.14 mmol), lithium hexamethyldisilazide (0.21 mL, 0.21 mmol, 1 M solution in tetrahydrofuran) and tetrahydrofuran (3 mL) were mixed and stirred for 0.5 h at 0° C. This mixture was quenched with 10 mL of a saturated ammonium chloride solution, extracted with ethyl acetate (20 mL×3), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 5:1), to obtain the target product phenyl-(5-(((t-butyldimethylsilyl) oxo)methyl)-6-(dimethoxymethyl) pyrid-2-yl)(methyl) aminocarboxylate 21c (18 mg, white solid), at a yield of 60%.

MS m/z (ESI): 447 [M+1]

$^1$H NMR (400 MHz, CDCl$_3$) δ 7.86 (d, J=8.4 Hz, 1H), 7.58 (d, J=7.2 Hz, 1H), 7.27-7.25 (m, 2H), 7.15-7.04 (m, 3H), 5.19 (s, 1H), 4.83 (s, 2H), 3.49 (s, 3H), 3.34 (s, 6H), 0.85 (s, 9H), 0.08 (s, 6H).

Step 3

1-(5-(((t-butyldimethylsilyl) oxo)methyl)-6-(dimethoxymethyl) pyrid-2-yl)-3-(4-chloro-5-cyanopyrid-2-yl)-1-methylurea Compounds phenyl-(5-(((t-butyldimethylsilyl) oxo)methyl)-6-(dimethoxymethyl) pyrid-2-yl)(methyl) aminocarboxylate 21c (18 mg, 0.04 mmol), 6-amino-4-chloronicotinonitrile (12 mg, 0.08 mmol), lithium hexamethyldisilazide (0.12 mL, 0.12 mmol, 1 M solution in tetrahydrofuran) and tetrahydrofuran (2 mL) were mixed, and stirred for 1 h at room temperature. This mixture was quenched with 10 mL of a saturated ammonium chloride solution, extracted with ethyl acetate (20 mL×3), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 3:1), to obtain the target product 1-(5-(((t-butyldimethylsilyl) oxo)methyl)-6-(dimethoxymethyl) pyrid-2-yl)-3-(4-chloro-5-cyanopyrid-2-yl)-1-methylurea 21 d (16 mg, white solid), at a yield of 79%.

MS m/z (ESI): 506 & 508 [M+1]

$^1$H NMR (400 MHz, CDCl$_3$) δ 13.78 (s, 1H), 8.40 (s, 1H), 8.34 (s, 1H), 7.95 (d, J=8.8 Hz, 1H), 6.97 (d, J=8.8 Hz, 1H), 5.35 (s, 1H), 4.78 (s, 2H), 3.37 (s, 3H), 3.33 (s, 6H), 0.83 (s, 9H), 0.02 (s, 6H).

Step 4

1-(5-(((t-butyldimethylsilyl) oxo)methyl)-6-(dimethoxymethyl) pyrid-2-yl)-3-(5-cyano-4-((2-methoxyethyl)amino) pyrid-2-yl)-1-methylurea Compounds 1-(5-(((t-butyldimethylsilyl) oxo)methyl)-6-(dimethoxymethyl) pyrid-2-yl)-3-(4-chloro-5-cyanopyrid-2-yl)-1-methylurea 21 d (10 mg, 0.02 mmol), 2-methoxy ethylamine (3 mg, 0.06 mmol), diisopropyl ethylamine (5 mg, 0.06 mmol) and N,N-dimethylacetamide (0.4 mL) were mixed and stirred for 16 h at 50° C. This mixture was diluted with 10 mL of water, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 3:1), to obtain the target product 1-(5-(((t-butyldimethylsilyl) oxo)methyl)-6-(dimethoxymethyl) pyrid-2-yl)-3-(5-cyano-4-((2-methoxyethyl)amino) pyrid-2-yl)-1-methylurea 21e (9 mg, white solid), at a yield of 76%.

MS m/z (ESI): 545 [M+1].

Step 5

3-(5-cyano-4-((2-methoxyethyl)amino) pyrid-2-yl)-1-(6-formyl-5-(hydroxymethyl) pyrid-2-yl)-1-methylurea Compounds 1-(5-(((t-butyldimethylsilyl) oxo)methyl)-6-(dimethoxymethyl) pyrid-2-yl)-3-(5-cyano-4-((2-methoxyethyl)amino) pyrid-2-yl)-1-methylurea 21e (9 mg, 0.02 mmol), hydrochloric acid (0.8 mL, 37%), water (1 mL) and tetrahydrofuran (2 mL) were mixed, and stirred for 1 h at room temperature. This mixture was quenched with a saturated sodium carbonate solution, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1:1), to obtain the target product 1-(5-(((t-butyldimethylsilyl)oxo)methyl)-6-(dimethoxymethyl) pyrid-2-yl)-3-(5-cyano-4-((2-methoxyethyl)amino) pyrid-2-yl)-1-methylurea 21 (3 mg, white solid), at a yield of 47%.

MS m/z (ESI): 385 [M+1]
$^1$H NMR (400 MHz, CDCl$_3$) δ major (21'): 12.60 (s, 1H), 8.08 (s, 1H), 7.70 (d, J=7.6 Hz, 1H), 7.58 (s, 1H), 7.07 (d, J=7.6 Hz, 1H), 6.53 (s, 1H), 5.31 (s, 1H), 5.25-5.23 (m, 1H), 5.05-5.02 (m, 1H), 3.63-3.61 (m, 2H), 3.51-3.50 (m, 2H), 3.49 (s, 3H), 3.41 (s, 3H). Minor (21): 12.94 (s, 1H), 10.25 (s, 1H), 8.17 (s, 1H), 8.06 (d, J=8.4 Hz, 1H), 7.57 (s, 1H), 7.27 (d, J=8.4 Hz, 1H), 6.53 (s, 1H), 5.31 (s, 1H), 5.25-5.23 (m, 1H), 5.05-5.02 (m, 1H), 3.63-3.61 (m, 2H), 3.51-3.50 (m, 2H), 3.49 (s, 3H), 3.41 (s, 3H).

Example 22

3-(4-chloro-5-cyanopyrid-2-yl)-1-(6-formyl-5-(hydroxymethyl) pyrid-2-yl)-1-methylurea Example 22 was synthesized with reference to the operation steps of Example 21, except that 1-(5-(((t-butyldimethylsilyl) oxo)methyl)-6-(dimethoxymethyl) pyrid-2-yl)-3-(4-chloro-5-cyanopyrid-2-yl)-1-methylurea was substituted for 3-(5-cyano-4-((2-m ethoxyethyl)amino)pyrid-2-yl)-1-(6-formyl-5-(hydroxymethyl) pyrid-2-yl)-1-methylurea in Step 5.

MS m/z (ESI): 346 & 348 [M+1]
$^1$H NMR (400 MHz, CDCl$_3$) δ major (22'): 13.10 (s, 1H), 8.46 (s, 1H), 8.45 (s, 1H), 7.77 (d, J=8.4 Hz, 1H), 7.13 (d, J=8.4 Hz, 1H), 6.51 (s, 1H), 5.29 (s, 1H), 5.11-5.08 (m, 2H), 3.53 (s, 3H). Minor (22): 13.55 (s, 1H), 10.25 (s, 1H), 8.48 (s, 1H), 8.47 (s, 1H), 8.10 (d, J=8.4 Hz, 1H), 7.35 (d, J=8.4 Hz, 1H), 4.97 (s, 2H), 4.08-4.06 (m, 1H), 3.57 (s, 3H).

Example 23

3-(5-cyano-4-((2-methoxyethyl)amino) pyrid-2-yl)-1-(6-formyl-5-(piperidin-4-yl) pyrid-2-yl)-1-methylurea

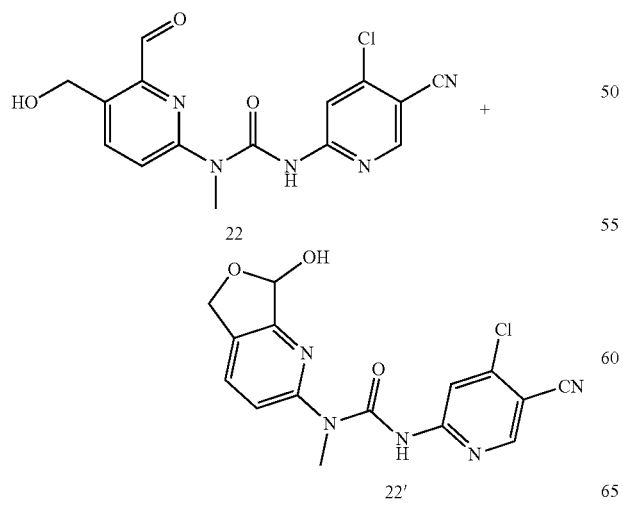

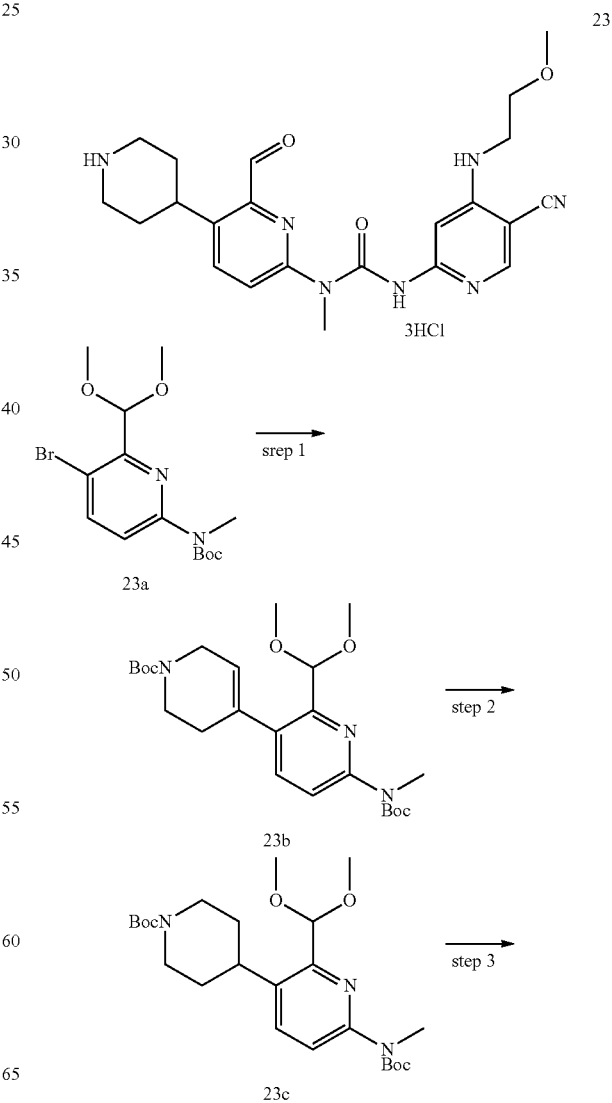

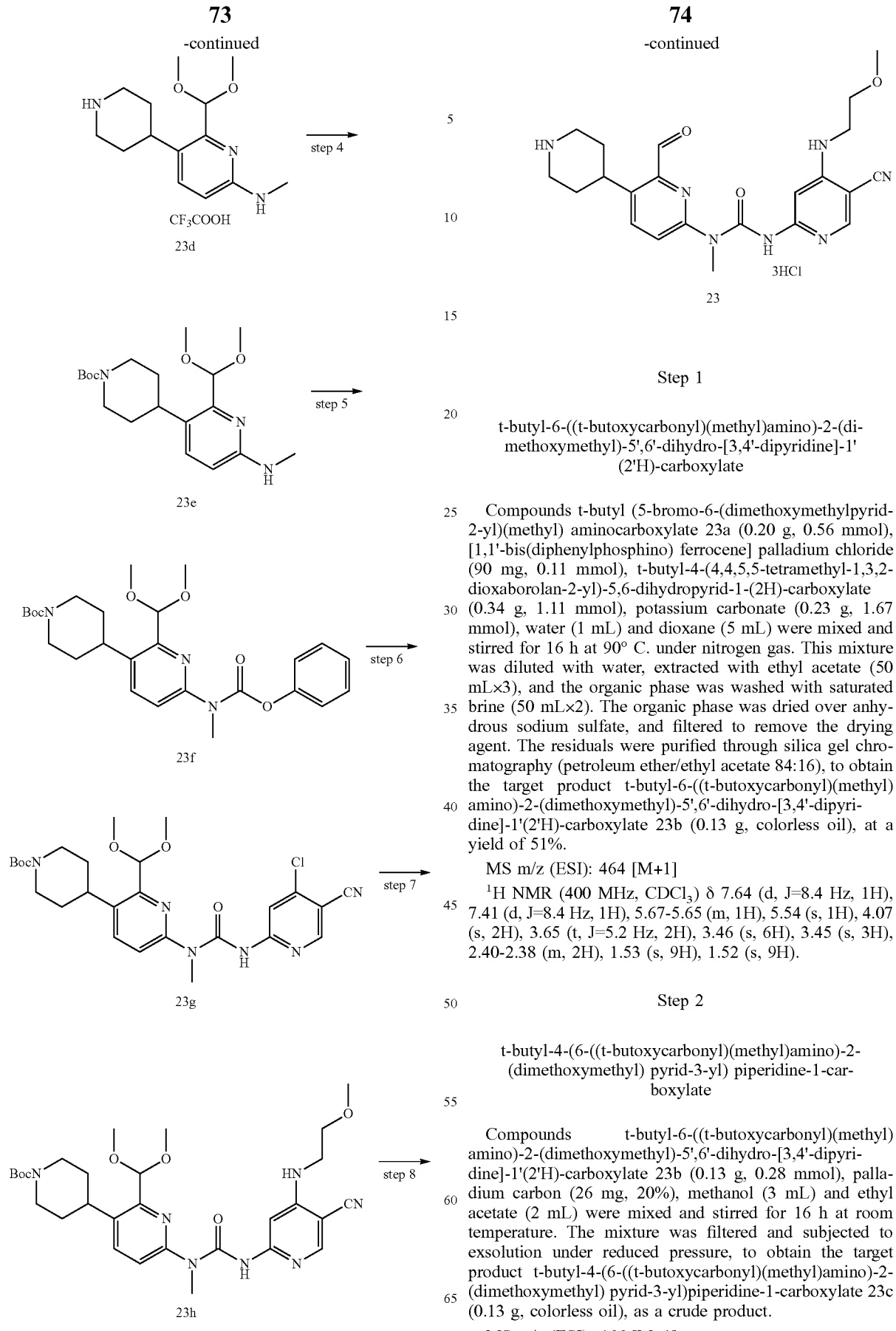

Step 1 t-butyl-6-((t-butoxycarbonyl)(methyl)amino)-2-(dimethoxymethyl)-5',6'-dihydro-[3,4'-dipyridine]-1'(2'H)-carboxylate Compounds t-butyl (5-bromo-6-(dimethoxymethylpyrid-2-yl)(methyl) aminocarboxylate 23a (0.20 g, 0.56 mmol), [1,1'-bis(diphenylphosphino) ferrocene] palladium chloride (90 mg, 0.11 mmol), t-butyl-4-(4,4,5,5-tetramethyl-1,3,2-dioxaborolan-2-yl)-5,6-dihydropyrid-1-(2H)-carboxylate (0.34 g, 1.11 mmol), potassium carbonate (0.23 g, 1.67 mmol), water (1 mL) and dioxane (5 mL) were mixed and stirred for 16 h at 90° C. under nitrogen gas. This mixture was diluted with water, extracted with ethyl acetate (50 mL×3), and the organic phase was washed with saturated brine (50 mL×2). The organic phase was dried over anhydrous sodium sulfate, and filtered to remove the drying agent. The residuals were purified through silica gel chromatography (petroleum ether/ethyl acetate 84:16), to obtain the target product t-butyl-6-((t-butoxycarbonyl)(methyl)amino)-2-(dimethoxymethyl)-5',6'-dihydro-[3,4'-dipyridine]-1'(2'H)-carboxylate 23b (0.13 g, colorless oil), at a yield of 51%.

MS m/z (ESI): 464 [M+1]

$^1$H NMR (400 MHz, CDCl$_3$) δ 7.64 (d, J=8.4 Hz, 1H), 7.41 (d, J=8.4 Hz, 1H), 5.67-5.65 (m, 1H), 5.54 (s, 1H), 4.07 (s, 2H), 3.65 (t, J=5.2 Hz, 2H), 3.46 (s, 6H), 3.45 (s, 3H), 2.40-2.38 (m, 2H), 1.53 (s, 9H), 1.52 (s, 9H).

Step 2 t-butyl-4-(6-((t-butoxycarbonyl)(methyl)amino)-2-(dimethoxymethyl) pyrid-3-yl) piperidine-1-carboxylate Compounds t-butyl-6-((t-butoxycarbonyl)(methyl)amino)-2-(dimethoxymethyl)-5',6'-dihydro-[3,4'-dipyridine]-1'(2'H)-carboxylate 23b (0.13 g, 0.28 mmol), palladium carbon (26 mg, 20%), methanol (3 mL) and ethyl acetate (2 mL) were mixed and stirred for 16 h at room temperature. The mixture was filtered and subjected to exsolution under reduced pressure, to obtain the target product t-butyl-4-(6-((t-butoxycarbonyl)(methyl)amino)-2-(dimethoxymethyl) pyrid-3-yl)piperidine-1-carboxylate 23c (0.13 g, colorless oil), as a crude product.

MS m/z (ESI): 466 [M+1].

Step 3

6-(dimethoxymethyl)-N-methyl-5-(piperidin-4-yl) pyridin-2-amine

Compounds t-butyl-4-(6-((t-butoxycarbonyl)(methyl) amino)-2-(dimethoxymethyl) pyrid-3-yl) piperidine-1-carboxylate 23c (0.13 g, 0.28 mmol), trifluoroacetic acid (1 mL) and dichloromethane (4 mL) were mixed, and stirred for 6 h at room temperature. The mixture was subjected to exsolution under reduced pressure, to obtain the target product 6-(dimethoxymethyl)-N-methyl-5-(piperidin-4-yl) pyridin-2-amine trifluoroacetate salt 23 d (95 mg, light-yellow solid), as a crude product.

MS m/z (ESI): 266 [M+1].

Step 4 t-butyl-4-(2-(dimethoxymethyl)-6-(methylamino) pyrid-3-yl) piperidine-1-carboxylate Compounds 6-(dimethoxymethyl)-N-methyl-5-(piperidin-4-yl) pyridin-2-amine trifluoroacetate salt 23 d (95 mg, 0.25 mmol), 2-t-butyl 2-carbonate (82 mg, 0.38 mmol), triethyl amine (76 mg, 0.75 mmol) and dichloromethane (4 mL) were mixed, and stirred for 6 h at room temperature. This mixture was quenched with 20 mL of water, extracted with ethyl acetate (20 mL×3), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 3:1), to obtain the target product t-butyl-4-(2-(dimethoxymethyl)-6-(methylamino) pyrid-3-yl)piperidine-1-carboxylate 23e (80 mg, white solid), at a yield of 65%.

MS m/z (ESI): 366 [M+1].

Step 5 t-butyl-4-(2-(dimethoxymethyl)-6-(methyl (phenoxycarbonyl) amino) pyrid-3-yl) piperidine-1-carboxylate Compounds t-butyl-4-(2-(dimethoxymethyl)-6-(methylamino) pyrid-3-yl)piperidine-1-carboxylate 23e (40 mg, 0.11 mmol), diphenyl carbonate (47 mg, 0.22 mmol), lithium hexamethyldisilazide (0.33 mL, 0.33 mmol, 1 M solution in tetrahydrofuran) and tetrahydrofuran (6 mL) were mixed and stirred for 0.5 h at 0° C. This mixture was quenched with 10 mL of a saturated ammonium chloride solution, extracted with ethyl acetate (20 mL×3), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 2:1), to obtain the target product t-butyl-4-(2-(dimethoxymethyl)-6-(methyl (phenoxycarbonyl) amino) pyrid-3-yl)piperidine-1-carboxylate 23f (20 mg, white solid), at a yield of 38%.

MS m/z (ESI): 486 [M+1].

Step 6 t-butyl-4-(6-(3-(4-chloro-5-cyanopyrid-2-yl)-1-methylureido)-2-(dimethoxymethyl) pyrid-3-yl)piperidine-1-carboxylate Compounds t-butyl-4-(2-(dimethoxymethyl)-6-(methyl (phenoxycarbonyl) amino) pyrid-3-yl)piperidine-1-carboxylate 23f (20 mg, 0.04 mmol), 6-amino-4-chloronicotinonitrile (12 mg, 0.08 mmol), lithium hexamethyldisilazide (0.12 mL, 0.12 mmol, 1 M solution in tetrahydrofuran) and tetrahydrofuran (2 mL) were mixed, and stirred for 1 h at room temperature. This mixture was quenched with 10 mL of a saturated ammonium chloride solution, extracted with ethyl acetate (20 mL×3), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1.5:1), to obtain the target product t-butyl-4-(6-(3-(4-chloro-5-cyanopyrid-2-yl)-1-methylureido)-2-(dimethoxymethyl) pyrid-3-yl)piperidine-1-carboxylate carboxylate 23g (10 mg, white solid), at a yield of 45%.

MS m/z (ESI): 545 & 547 [M+1].

Step 7 t-butyl-4-(6-(3-(5-cyano-4-((2-methoxyethyl)amino) pyrid-2-yl)-1-methylureido)-2-(dimethoxymethyl) pyrid-3-yl)piperidine-1-carboxylate Compounds t-butyl-4-(6-(3-(4-chloro-5-cyanopyrid-2-yl)-1-methylureido)-2-(dimethoxymethyl) pyrid-3-yl)piperidine-1-carboxylate 23g (10 mg, 0.02 mmol), 2-methoxy ethylamine (3 mg, 0.06 mmol), diisopropyl ethylamine (5 mg, 0.06 mmol) and N,N-dimethylacetamide (0.4 mL) were mixed and stirred for 16 h at 50° C. This mixture was diluted with 10 mL of water, extracted with ethyl acetate (20 mL×2), and the organic phase was washed with saturated brine (20 mL×2). The organic phase was dried over anhydrous sodium sulfate, and filtered to remove the drying agent. The residuals were purified through a preparative silica gel plate (petroleum ether/ethyl acetate 1.5:1), to obtain the target product t-butyl-4-(6-(3-(5-cyano-4-((2-methoxyethyl) amino) pyrid-2-yl)-1-methylureido)-2-(dimethoxymethyl) pyrid-3-yl)piperidine-1-carboxylate 23 h (6 mg, white solid), at a yield of 56%.

MS m/z (ESI): 584 [M+1].

Step 8

3-(5-cyano-4-((2-methoxyethyl)amino) pyrid-2-yl)-1-(6-formyl-5-(piperidin-4-yl) pyrid-2-yl)-1-methylurea Compounds t-butyl-4-(6-(3-(5-cyano-4-((2-methoxyethyl)amino) pyrid-2-yl)-1-methylureido)-2-(dimethoxymethyl) pyrid-3-yl)piperidine-1-carboxylate 23 h (6 mg, 0.01 mmol), hydrochloric acid (0.8 mL, 37%), water (1 mL) and tetrahydrofuran (2 mL) were mixed, and stirred for 1 h at room temperature. The mixture was subjected to exsolution under reduced pressure, to obtain the target product 3-(5-cyano-4-((2-methoxyethyl)amino) pyrid-2-yl)-1-(6-formyl-5-(piperidin-4-yl) pyrid-2-yl)-1-methylurea hydrochloride 23 (4 mg, white solid), at a yield of 89%.

MS m/z (ESI): 438 [M+1]

$^1$H NMR (400 MHz, CD$_3$OD) δ 8.40 (s, 1H), 8.01 (d, J=8.4 Hz, 1H), 7.37 (d, J=7.6 Hz, 1H), 6.92 (s, 1H), 6.07 (s, 1H), 3.71-3.58 (m, 6H), 3.55 (s, 3H), 3.43 (s, 3H), 3.25-3.20 (m, 2H), 3.19-3.15 (m, 1H), 2.12-1.95 (m, 4H).

Example 24

(S)-3-(5-cyano-4-((1-methoxyprop-2-yl)oxy) pyrid-2-yl)-1-(6-formyl-5-((4-methyl-2-carbonylpiperazin-1-yl)methyl) pyrid-2-yl)-1-methylurea

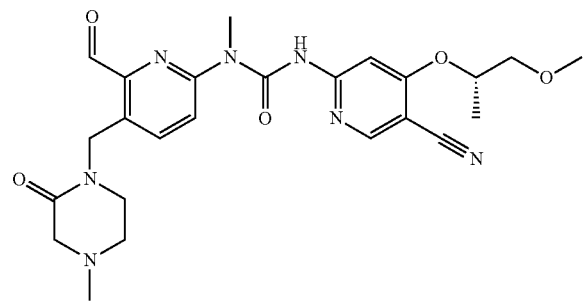

24

Example 24 was synthesized with reference to the operation steps of Example 18, except that (S)-1-methoxypropan-2-ol was substituted for (R)-1-methoxypropan-2-ol in Step 1.

MS m/z (ESI): 496 [M+1]

$^1$H NMR (400 MHz, CDCl$_3$) δ 13.31 (s, 1H), 10.26 (s, 1H), 8.34 (s, 1H), 7.99 (s, 1H), 7.94 (d, J=8.7 Hz, 1H), 7.29 (d, J=8.7 Hz, 1H), 5.10 (s, 2H), 4.99-4.74 (m, 1H), 3.73-3.55 (m, 2H), 3.52 (s, 3H), 3.43 (s, 3H), 3.37 (t, J=5.3 Hz, 2H), 3.20 (s, 2H), 2.67 (t, J=5.3 Hz, 2H), 2.36 (s, 3H), 1.41 (d, J=6.3 Hz, 3H).

Example 25

(R)-3-(5-cyano-4-((1-hydroxyprop-2-yl)oxy) pyrid-2-yl)-1-(6-formyl-5-((4-methyl-2-carbonylpiperazin-1-yl)methyl) pyrid-2-yl)-1-methylurea

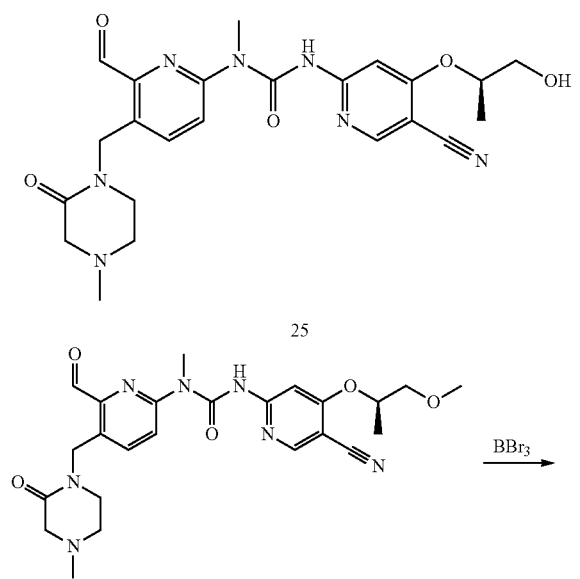

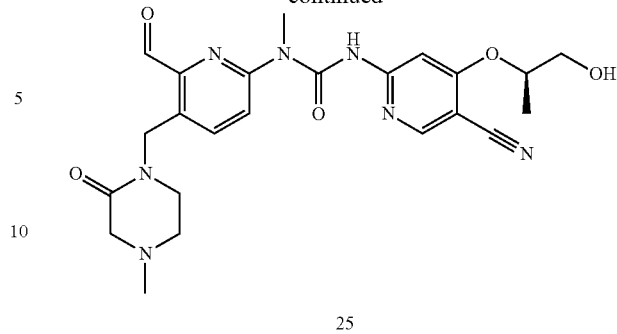

25

Compounds (R)-3-(5-cyano-4-((1-methoxyprop-2-yl)oxy) pyrid-2-yl)-1-(6-formyl-5-((4-methyl-2-carbonylpiperazin-1-yl)methyl) pyrid-2-yl)-1-methylurea 18 (4.0 g, 8 mmol) and dichloromethane (80 mL) were mixed. Boron tribromide (20.2 g, 81 mmol) was added therein dropwise, in an ice-salt bath. After the dropwise addition, the ice-salt bath was removed, and the mixture was further stirred for 30 min at room temperature. This mixture was quenched with ice water (300 mL) that was slowly poured therein, adjusted to pH 8-9 with an aqueous saturated sodium carbonate solution (200 ml), and extracted with dichloromethane (150 mL×3). Organic phases were combined, dried over anhydrous sodium sulfate, filtered to remove the drying agent, and subjected to exsolution under reduced pressure, to obtain a crude product, which was subjected to flash column chromatography (dichloromethane:methanol=20:1) to obtain the target product (R)-3-(5-cyano-4-((1-hydroxyprop-2-yl)oxy) pyrid-2-yl)-1-(6-formyl-5-((4-methyl-2-carbonylpiperazin-1-yl)methyl) pyrid-2-yl)-1-methylurea 25 (2.3 g, 4.8 mmol, white solid), at a yield of 60%.

MS m/z (ESI): 482 [M+1]

$^1$H NMR (400 MHz, CDCl$_3$) δ 13.36 (s, 1H), 10.26 (s, 1H), 8.35 (s, 1H), 7.99 (s, 1H), 7.94 (d, J=8.5 Hz, 1H), 7.30 (d, J=8.5 Hz, 1H), 5.10 (s, 2H), 4.88-4.76 (m, 1H), 3.91-3.78 (m, 2H), 3.53 (s, 3H), 3.42-3.38 (s, 2H), 3.20 (s, 2H), 2.75-2.63 (m, 2H), 2.36 (s, 3H), 1.41 (d, J=6.0 Hz, 3H).

Example 26

(S)-3-(5-cyano-4-((1-hydroxyprop-2-yl)oxy) pyrid-2-yl)-1-(6-formyl-5-((4-methyl-2-carbonylpiperazin-1-yl)methyl) pyrid-2-yl)-1-methylurea

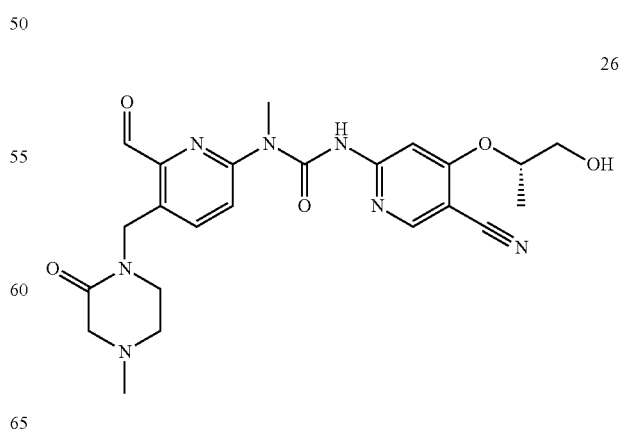

26

Example 26 was synthesized with reference to the operation steps of Example 25, except that (S)-3-(5-cyano-4-((1- methoxyprop-2-yl)oxy) pyrid-2-yl)-1-(6-formyl-5-((4-methyl-2-carbonylpiperazin-1-yl)methyl) pyrid-2-yl)-1-methylurea was substituted for (R)-3-(5-cyano-4-((1-methoxyprop-2-yl)oxy) pyrid-2-yl)-1-(6-formyl-5-((4-methyl-2-carbonylpiperazin-1-yl)methyl) pyrid-2-yl)-1-methylurea in Step 1.

MS m/z (ESI): 482 [M+1]

$^1$H NMR (400 MHz, CDCl$_3$) δ 13.37 (s, 1H), 10.26 (s, 1H), 8.34 (s, 1H), 7.97 (s, 1H), 7.95 (d, J=8.8 Hz, 1H), 7.32 (d, J=8.8 Hz, 1H), 5.11 (s, 2H), 4.91-4.74 (m, 1H), 3.96-3.76 (m, 2H), 3.54 (s, 3H), 3.46-3.33 (m, 2H), 3.22 (s, 2H), 2.79-2.62 (m, 2H), 2.38 (s, 3H), 1.42 (d, J=6.0 Hz, 3H).

Biological Experiment

FGFR4 Activity Inhibition Test

The influence of the compound according to the present invention on the activity of fibroblast growth factor receptor 4 (FGFR4) was evaluated by an in vitro kinase assay experiment.

The experimental method is summarized as follows:

The in vitro activity of FGFR4 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM MgCl$_2$, 1 mM DTT; the human recombinant FGFR4 catalytic structural domain protein (amino acids 460-802) was commercially available from Tsinghua Protein Research Technology Center, diluted with the reaction buffer to a 0.5 ng/μL kinase solution; the substrate reaction solution comprised a biotin labeled tyrosine kinase substrate diluted with the reaction buffer to 500 nM (Cisbio, catalog number 62TK0PEC), and 90 μM ATP, and the assay solution comprised an Eu$^{3+}$ labeled cage-shaped antibody (Cisbio, Catalog number 61T66KLB) diluted with the assay buffer (Cisbio, Catalog number 62SDBRDF) to 0.125 ng/μL, and 31.25 nM streptavidin labeled XL665 (Cisbio, Catalog number 610SAXLB).

The compound was dissolved and diluted in 100% DMSO to 100 μM, then 4-fold-series diluted with DMSO to a minimum concentration of 0.0061 μM, and each concentration point was then 40-fold diluted with the reaction buffer. If the IC$_{50}$ value of the compound was very low, the initial concentration of the compound could be reduced.

4 μL of a compound solution and 2 μL of an FGFR4 kinase solution were added into a 384 well assay plate (Thermo, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the Eu$^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision. The ratio of 665/620 is in positive correlation to the phosphorylation degree of the substrate, thereby to detect the FGFR4 kinase activity. In this experiment, the group without the protein added was used as a negative control (100% inhibition), and the group with the protein but without the compound added was used as a positive control (0% inhibition). The inhibition percentage of the compound against FGFR4 activity could be calculated with the following formula:

Inhibition percentage=100−100*(signal$_{compound}$−signal$_{negative\ control}$)/(signal$_{positive\ control}$−signal$_{negative\ control}$)

The IC$_{50}$ value of the compound was calculated by the following formula, from 10 concentration points, with XLfit (ID Business Solutions Ltd., UK):

Y=Bottom+(Top−Bottom)/(1+10^((Log IC$_{50}$−X)*slope factor))

Where, Y is the inhibition percentage, Bottom is the bottom plateau of the curve (the bottom plateau of the S-type curve), Top is the top plateau of the curve (the top plateau of the S-type curve), and X is the log value of the compound concentration to be measured.

FGFR1 Activity Inhibition Test

The influence of the compound according to the present invention on the activity of fibroblast growth factor receptor 1 (FGFR1) was evaluated by an in vitro kinase assay experiment.

The experimental method is summarized as follows:

The in vitro activity of FGFR1 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM MgCl$_2$, 1 mM DTT; the human recombinant FGFR1 catalytic structural domain protein (amino acids 308-731) was purified by the company itself, diluted with the reaction buffer to a 0.6 ng/μL kinase solution; the substrate reaction solution comprised a biotin labeled tyrosine kinase substrate diluted with the reaction buffer to 400 nM (Cisbio, catalog number 62TK0PEC), and 40 μM ATP, and the assay solution comprised an Eu$^{3+}$ labeled cage-shaped antibody (Cisbio, Catalog number 61T66KLB) diluted with the assay buffer (Cisbio, Catalog number 62SDBRDF) to 0.125 ng/μL, and 25 nM streptavidin labeled XL665 (Cisbio, Catalog number 610SAXLB).

The compound was dissolved and diluted in 100% DMSO to 1 mM, then 4-fold-series diluted with DMSO to a minimum concentration of 0.0061 μM, and each concentration point was then 40-fold diluted with the reaction buffer. If the IC$_{50}$ value of the compound was very low, the initial concentration of the compound could be reduced.

4 μL of a compound solution and 2 μL of an FGFR1 kinase solution were added into a 384 well assay plate (Thermo, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the Eu$^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision. The ratio of 665/620 is in positive correlation to the phosphorylation degree of the substrate, thereby to detect the FGFR4 kinase activity. In this experiment, the group without the protein added was used as a negative control (100% inhibition), and the group with the protein but without the compound added was used as a positive control (0% inhibition). The inhibition percentage of the compound against FGFR1 activity could be calculated with the following formula:

Inhibition percentage=100−100*(signal$_{compound}$−signal$_{negative\ control}$)/(signal$_{positive\ control}$−signal$_{negative\ control}$)

The IC$_{50}$ value of the compound was calculated by the following formula, from 10 concentration points, with XLfit (ID Business Solutions Ltd., UK):

$Y$=Bottom+(Top−Bottom)/(1+10^((Log IC$_{50}$−$X$)*slope factor))

Where, Y is the inhibition percentage, Bottom is the bottom plateau of the curve (the bottom plateau of the S-type curve), Top is the top plateau of the curve (the top plateau of the S-type curve), and X is the log value of the compound concentration to be measured.

FGFR2 Activity Inhibition Test

The influence of the compound according to the present invention on the activity of fibroblast growth factor receptor 2 (FGFR2) was evaluated by an in vitro kinase assay experiment.

The experimental method is summarized as follows:

The in vitro activity of FGFR2 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM MgCl$_2$, 1 mM DTT; the human recombinant FGFR2 catalytic structural domain protein (amino acids 400-821) was commercially available from Beijing Sino Biological Inc., diluted with the reaction buffer to a 0.045 ng/μL kinase solution; the substrate reaction solution comprised a biotin labeled tyrosine kinase substrate diluted with the reaction buffer to 800 nM (Cisbio, catalog number 62TK0PEC), and 50 μM ATP, and the assay solution comprised an Eu$^{3+}$ labeled cage-shaped antibody (Cisbio, Catalog number 61T66KLB) diluted with the assay buffer (Cisbio, Catalog number 62SDBRDF) to 0.125 ng/μL, and 50 nM streptavidin labeled XL665 (Cisbio, Catalog number 610SAXLB).

The compound was dissolved and diluted in 100% DMSO to 100 μM, then 4-fold-series diluted with DMSO to a minimum concentration of 0.0061 μM, and each concentration point was then 40-fold diluted with the reaction buffer. If the IC$_{50}$ value of the compound was very low, the initial concentration of the compound could be reduced.

4 μL of a compound solution and 2 μL of an FGFR2 kinase solution were added into a 384 well assay plate (Thermo, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the Eu$^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision. The ratio of 665/620 is in positive correlation to the phosphorylation degree of the substrate, thereby to detect the FGFR2 kinase activity. In this experiment, the group without the protein added was used as a negative control (100% inhibition), and the group with the protein but without the compound added was used as a positive control (0% inhibition). The inhibition percentage of the compound against FGFR2 activity could be calculated with the following formula:

Inhibition percentage=100−100*(signal$_{compound}$−signal$_{negative\ control}$)/(signal$_{positive\ control}$−signal$_{negative\ control}$)

The IC$_{50}$ value of the compound was calculated by the following formula, from 10 concentration points, with XLfit (ID Business Solutions Ltd., UK):

$Y$=Bottom+(Top−Bottom)/(1+10^((Log IC$_{50}$−$X$) *slope factor))

Where, Y is the inhibition percentage, Bottom is the bottom plateau of the curve (the bottom plateau of the S-type curve), Top is the top plateau of the curve (the top plateau of the S-type curve), and X is the log value of the compound concentration to be measured.

FGFR3 Activity Inhibition Test

The influence of the compound according to the present invention on the activity of fibroblast growth factor receptor 3 (FGFR3) was evaluated by an in vitro kinase assay experiment.

The experimental method is summarized as follows:

The in vitro activity of FGFR3 was determined by assaying the phosphorylation level of the substrate in the kinase reaction, by means of an HTRF kinase assay kit. The reaction buffer comprised the following components: 5-fold diluted Enzymatic buffer/kinase 5× (Cisbio, Catalog number 62EZBFDD) (main ingredient: 50 mM HEPES, pH 7.0), 5 mM MgCl$_2$, 1 mM DTT; the human recombinant FGFR3 catalytic structural domain protein (amino acids 399-806) was commercially available from Sino Biological Inc., diluted with the reaction buffer to a 0.3 ng/μL kinase solution; the substrate reaction solution comprised a biotin labeled tyrosine kinase substrate diluted with the reaction buffer to 1000 nM (Cisbio, catalog number 62TK0PEC), and 90 μM ATP, and the assay solution comprised an Eu$^{3+}$ labeled cage-shaped antibody (Cisbio, Catalog number 61T66KLB) diluted with the assay buffer (Cisbio, Catalog number 62SDBRDF) to 0.125 ng/μL, and 62.5 nM streptavidin labeled XL665 (Cisbio, Catalog number 610SAXLB).

The compound was dissolved and diluted in 100% DMSO to 100 μM, then 4-fold-series diluted with DMSO to a minimum concentration of 0.0061 μM, and each concentration point was then 40-fold diluted with the reaction buffer. If the IC$_{50}$ value of the compound was very low, the initial concentration of the compound could be reduced.

4 μL of a compound solution and 2 μL of an FGFR3 kinase solution were added into a 384 well assay plate (Thermo, Catalog number 264706), mixed uniformly and then incubated for 15 min at room temperature; subsequently, 4 μL of the substrate reaction solution was added therein, and the reaction mixture was incubated for 60 min at room temperature; and then 10 μL of an assay solution of an equal volume to the reaction was added therein and mixed uniformly, followed by placement at room temperature. After 60 min, the enzyme reaction was terminated by EDTA in the assay solution, and the phosphorylated products were identified by both the Eu$^{3+}$ labeled cage-shaped antibody (donor) and the streptavidin labeled XL665 antibody (receptor) at the same time. After the excitation with laser, the donors and receptors that were close to each other experienced energy resonance transfer, and the energy transferred from the donor (620 nm) to the receptor (665 nm) could be detected with Envision. The ratio of 665/620 is in positive correlation to the phosphorylation degree of the substrate, thereby to detect the FGFR3 kinase activity. In this experiment, the group without the protein added was used as a negative control (100% inhibition), and the group with the protein but without the compound added was used as a positive control (0% inhibition). The inhibition percentage of the compound against FGFR2 activity could be calculated with the following formula:

Inhibition percentage=100−100*(signal$_{compound}$−signal$_{negative\ control}$)/(signal$_{positive\ control}$−signal$_{negative\ control}$)

The IC$_{50}$ value of the compound was calculated by the following formula, from 10 concentration points, with XLfit (ID Business Solutions Ltd., UK):

$Y$=Bottom+(Top−Bottom)/(1+10^((Log IC$_{50}$−$X$)*slope factor))

Where, Y is the inhibition percentage, Bottom is the bottom plateau of the curve (the bottom plateau of the S-type curve), Top is the top plateau of the curve (the top plateau of the S-type curve), and X is the log value of the compound concentration to be measured.

Bioassay examples: A: <10 nM, B: 10-100 nM, C: 100-1000 nM, D: >1000 nM, ND: not detected

| Compound No. | FGFR4 IC$_{50}$ (nM) | FGFR1 IC$_{50}$ (nM) | FGFR2 IC$_{50}$ (nM) | FGFR3 IC$_{50}$ (nM) |
| --- | --- | --- | --- | --- |
| 1 | A | D | ND | ND |
| 2 | C | D | ND | ND |
| 3 | B | D | ND | ND |
| 4 | C | D | ND | ND |
| 5 | A | D | ND | ND |
| 6 | A | D | ND | ND |
| 7 | A | D | ND | ND |
| 8 | C | D | ND | ND |
| 9 | A | D | D | D |
| 10 | A | D | D | D |
| 11 | B | D | D | D |
| 12 | A | D | D | D |
| 13 | B | D | D | D |
| 14 | A | D | D | D |
| 15 | B | D | ND | ND |
| 16 | A | D | D | D |
| 17 | C | D | D | D |
| 18 | A | D | D | D |
| 19 | A | D | D | D |
| 20 | A | D | D | D |
| 21 | C | D | D | D |
| 22 | C | D | D | D |
| 23 | B | D | D | ND |
| 24 | A | D | D | D |
| 25 | A | D | D | D |
| 26 | A | D | D | D |

The compound according to the present invention has a selective inhibitory effect on FGFR4.

Hep3B Cell Proliferation Inhibition Test

The influence of the compound according to the present invention on Hep3B cell proliferation was evaluated by a luminescence cell viability test.

The experimental method is summarized as follows:

A CellTilter-Glo (CTG) assay kit was used to detect an indicator ATP of active cellular metabolism by means of a unique stable luciferase, and the luminous signal produced in the test was in direct proportion to the count of active cells in the medium, thereby to detect the cell proliferation of Hep3B.

A CellTilter-Glo agent (Promega, G7572) was comprised of a CellTilter-Glo lyophilized powder and a CellTilter-Glo buffer, and the lyophilized powder was dissolved into the buffer in use.

Hep3B cells (ATCC, HB-8064) (cell source: Shanghai Academy of Life Sciences, Chinese Academy of Sciences) were cultured in a DMEM complete medium (Thermofisher, 11995073) containing a 10% FBS (GBICO, 10099-141) and 100 units/ml mycillin mixed solution (Thermofisher, 15140122). When the cells coverage reached 80-90% in the culture vessel, after the cells were digested and blown about with 0.25% pancreatin (containing EDTA) (Thermofisher, 25200056), they were planted in a white 384 well plate (Thermofisher, 164610), with 1000 cells in each well (27 μl of a DMEM complete medium), and then the 384 well plate was placed into an incubator at 37° C. and 5% CO$_2$ and cultured overnight (18-20 h). The compound was dissolved and diluted in 100% DMSO to 100 μM, then 4-fold-series diluted with DMSO to a minimum concentration of 0.0061 μM, and each concentration point was 50-fold diluted with the FBS-free DMEM medium. If the IC$_{50}$ value of the compound was very low, the initial concentration of the compound could be reduced. After the overnight culture, 3 μl of the DMEM diluted compound was added into each well, and gently centrifugated and mixed uniformly, where a 10 μM BLU9931 group was added to serve as a negative control (100% inhibition) and a 0.2% DMSO group was added to serve as a positive control (0% inhibition). This 384 well plate was placed into an incubator at 37° C. and 5% CO$_2$ for further culture, taken out after 72 h, and stood at room temperature for 30 min. The CTG agent was also taken out and balanced to room temperature. 15 μl of the CTG agent was added into each well, and placed onto a shaker to be gently shaken for 3 min to ensure sufficient cell lysis. After 10 min of standing to allow the luminescence signal to be stable, the luminescence signal was read with EnVision (Perkin Elmer).

The inhibition percentage of the compound against Hep3B cell proliferation could be calculated with the following formula:

Inhibition percentage=100−100*(signal$_{compound}$−signal$_{negative\ control}$)/(signal$_{positive\ control}$−signal$_{negative\ control}$)

The IC$_{50}$ value of the compound was calculated by the following formula, from 8 concentration points, with XLfit (ID Business Solutions Ltd., UK):

$Y$=Bottom+(Top−Bottom)/(1+10^((Log IC$_{50}$−$X$)*slope factor))

Where, Y is the inhibition percentage, Bottom is the bottom plateau of the curve (the bottom plateau of the S-type curve), Top is the top plateau of the curve (the top plateau of the S-type curve), and X is the log value of the compound concentration to be measured.

Bioassay examples: A: <50 nM, B: 50-100 nM,

| Compound No. | Hep3B IC$_{50}$ (nM) |
| --- | --- |
| 9 | A |
| 10 | B |
| 12 | A |
| 14 | A |

| Compound No. | Hep3B IC$_{50}$ (nM) |
|---|---|
| 16 | A |
| 18 | A |
| 19 | B |
| 23 | B |

It can be seen from the above table that, the compound according to the present invention has a good inhibitory effect against the Hep3B cell proliferation.

Example 27

Efficacy of Compound 18 in Hep3B HCC Xenograft Model

The study was conducted to evaluate the in-vivo antitumor activity of compound 18 (see Example 18) in female BALB/c nude mice bearing FGF19/FGFR4-overexpressed Hep3B hepatocellular carcinoma (HCC) xenograft tumors.

Female nude mice (BALB/c nude) of 6-8 weeks old were ordered from Beijing Vital River Laboratory Animal Technology Co., Ltd. Tumor cell culture and inoculation: Hep3B cells were cultured with DMEM medium (Gibco) supplemented with 10% FBS (Gemini). The cells were harvested in 90% confluence and the viability was no less than 90%. Mice were implanted subcutaneously with 200 μL of 5×10$^6$ Hep3B cells in 50% Matrigel into the right flank with Hep3B cell and were orally treated with vehicle, compound 18 at 10, 30, 100 mg/kg, twice a day (BID) and 60 mg/kg, once a day (QD), or reference sorafenib at 40 mg/kg, QD. Dosing was initiated on day 0 and effects on tumor growth were evaluated by measuring percent tumor growth inhibition (TGI) at the end of the study. Tolerability was assessed by body weight loss, lethality, and clinical signs of adverse treatment-related side effects. Tumor volumes and body weights were measured twice per week in the administration period. The percentage of TGI was determined on day 18 of the study. The difference between the mean values of tumor volume in treatment and vehicle groups was analyzed for significance using one-way ANOVA (followed by Dennett's test) at each time point and a P<0.05 was considered to be statistically significant.

The efficacy results demonstrated that compound 18 dose-dependently reduced tumor size and tumor weight in the Hep3B model. The mean tumor size of the vehicle treated control mice reached 1,970 mm$^3$ at day 18 after treatment. Treatment with compound 18 at dose levels of 10, 30 and 100 mg/kg (BID for 18 days) and 60 mg/kg (QD for 18 days) produced significant antitumor activities; their mean tumor sizes were 230, 16, 0 and 86 mm$^3$, respectively, with TGI value of 96.4%, 108.3%, 109.2% and 104.4%, respectively (FIG. 1) (P<0.0001, 0.0001, 0.0001 and 0.0001). Reference drug sorafenib produced some antitumor activity too at 40 mg/kg, and compound 18 showed greater TGI at doses 100 mg/kg. Compound 18 at 100 mg/kg induced complete regression of Hep3B HCC xenograft tumors (TGI value=109.2%). The results of the tumor weights were essentially consistent with the tumor volumes.

Figure 2:
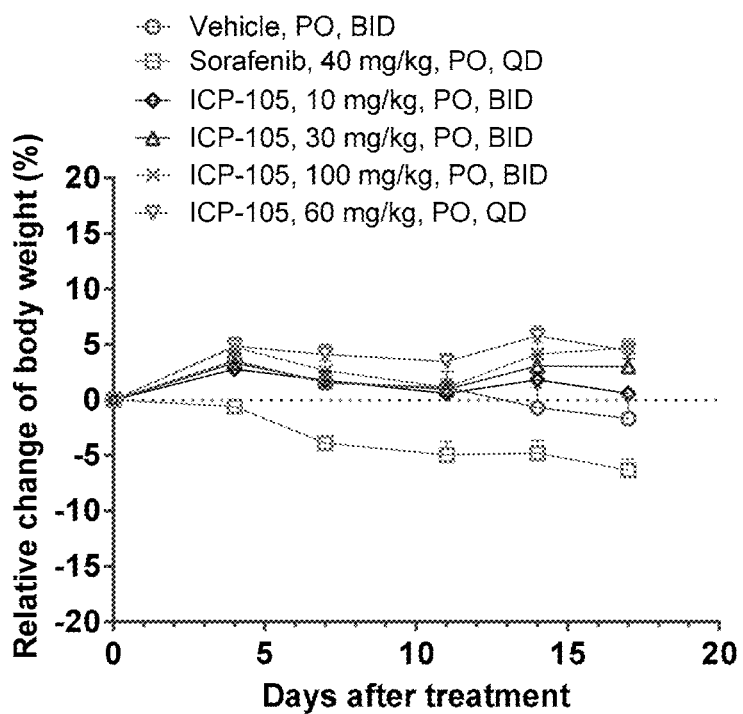
FIG. 2 shows the relative change of body weights (%) after treatments with compound 18 in Hep3B HCC xenograft model. The relative change of body weights (% RCBW) was calculated based on the following formula: RCBW (%)=(BWi−BW0)/BW0×100%, BWi was the body-weight on the day of dosing and BW0 was the bodyweight on the first day of administration. Data points represent percent group mean change in BW. Error bars represent standard error of the mean (SEM).

The test compound 18 at all dose levels were well-tolerated by the tumor-bearing animals. The mice in the all groups didn't exhibit significant body weight loss during the treatment (FIG. 2).

In summary, the results of this study demonstrated that compound 18 produced marked antitumor activities against the Hep3B human HCC xenograft model with FGF19/FGFR4 overexpression and it was well well-tolerated by the tumor-bearing animals. The results indicated that compound 18 is a safe and efficacious anticancer agent.

The invention claimed is:

1. A compound of Formula V or a pharmaceutically acceptable salt thereof:

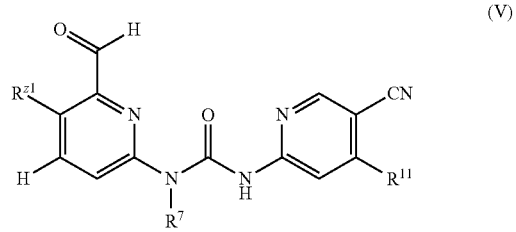

(V)

wherein $R^{Z1}$ is selected from the group consisting of, halogen, and C1-C4 alkyl optionally substituted with hydroxyl, or $R^{Z1}$ is

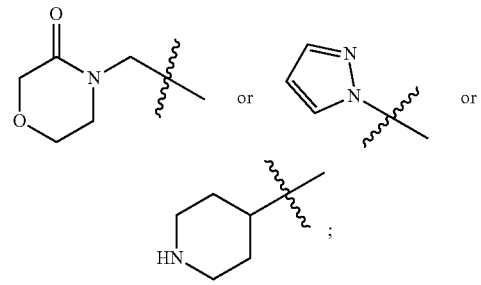

$R^7$ is hydrogen or C1-C4 alkyl;
$R^{11}$ is selected from the group consisting of NR$^2$R$^3$, halogen, and —O—(C1-C8 alkylene)-OR$^a$;
$R^2$, and $R^3$ are independently C1-C8 alkyl, wherein the alkyl is optional substituted by —OR$^b$; and
$R^a$ and $R^b$ are independently H or C1-C8 alkyl.

2. A compound of Formula V or a pharmaceutically acceptable salt thereof,

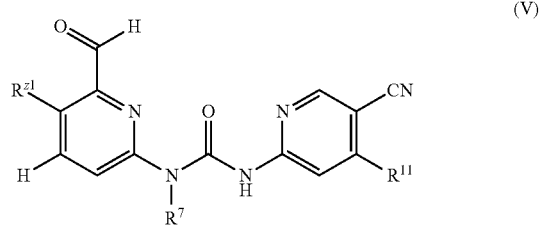

(V)

wherein $R^{Z1}$ is

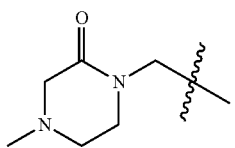 [SMILES: *CN1CCN(C)CC1=O]

R⁷ is hydrogen or C1-C4 alkyl;
R¹¹ is —O—(C1-C8 alkylene)-ORᵃ, and
Rᵃ is H or C1-C8 alkyl.

3. The compound according to claim 2, or the pharmaceutically acceptable salt thereof, wherein the compound is:

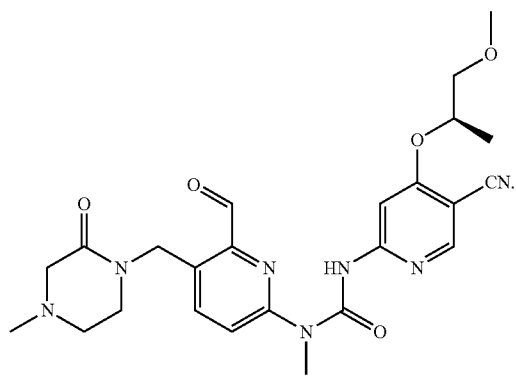 [SMILES: COC[C@@H](C)Oc1cc(NC(=O)N(C)c2ccc(CN3CCN(C)CC3=O)c(C=O)n2)ncc1C#N]

4. The compound according to claim 2, or the pharmaceutically acceptable salt thereof, wherein the compound is:

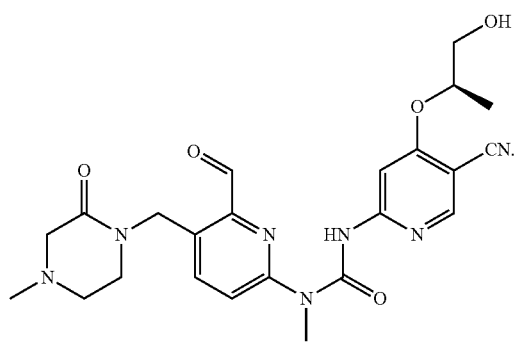 [SMILES: C[C@H](CO)Oc1cc(NC(=O)N(C)c2ccc(CN3CCN(C)CC3=O)c(C=O)n2)ncc1C#N]

5. A compound of Formula V' or a pharmaceutically acceptable salt thereof:

V'

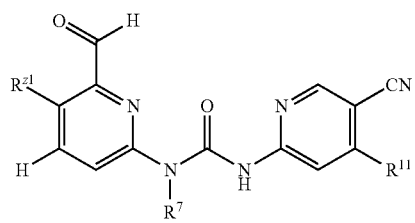

wherein R^{Z1} is

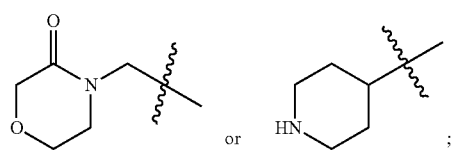 [SMILES: *CN1CCOCC1=O ; *C1CCNCC1]

;

R⁷ is hydrogen or C1-C4 alkyl;
R¹¹ is selected from the group consisting of NR²R³, halogen, C1-C3 alkoxy, and OR⁴;

R², R³ and R⁴ are independently H and C1-C8 alkyl, wherein the alkyl is optional substituted by —OR⁵; and
R⁵ is H or C1-C8 alkyl.

6. A compound having the following formula, or the pharmaceutically acceptable salt thereof:

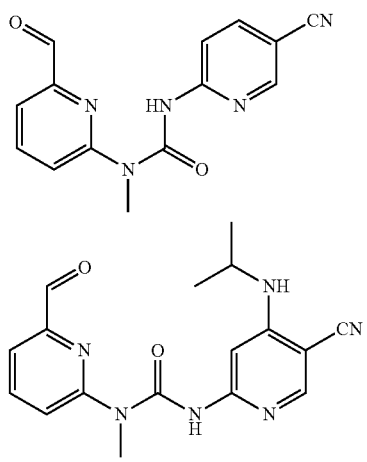

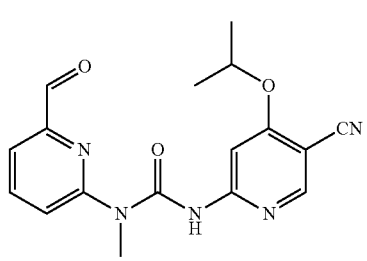

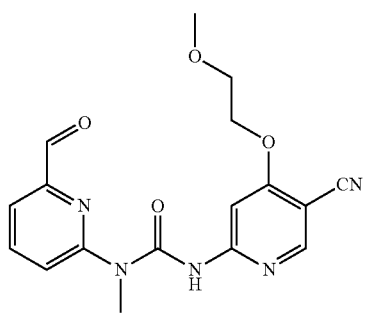

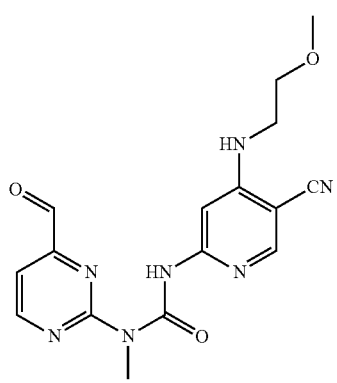

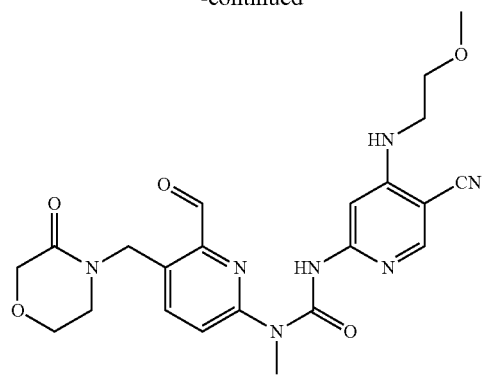
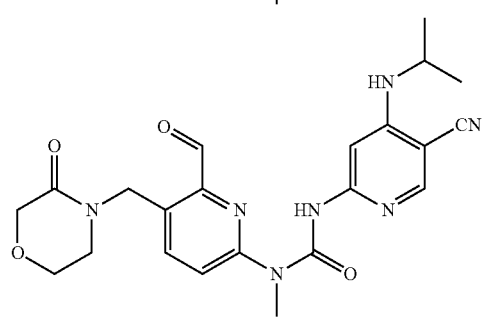
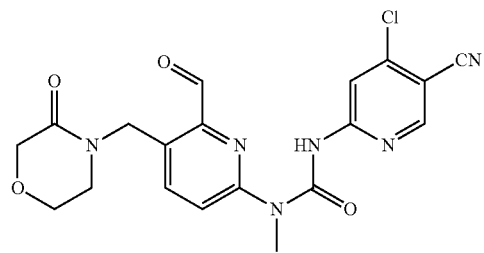
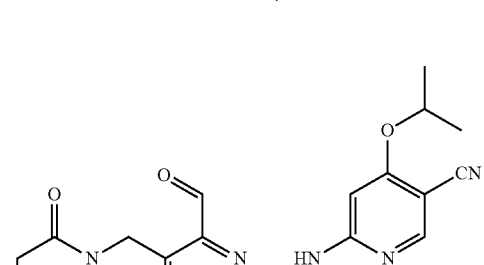
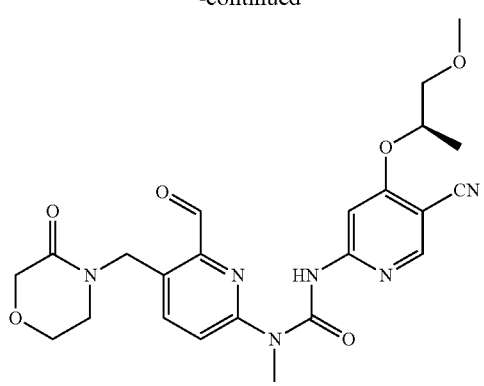
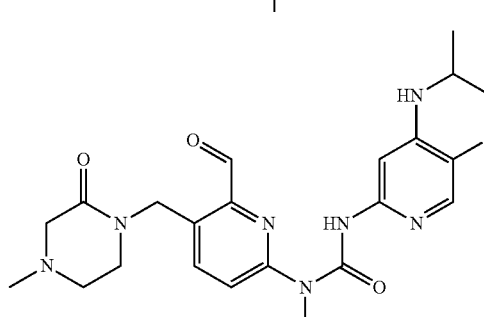
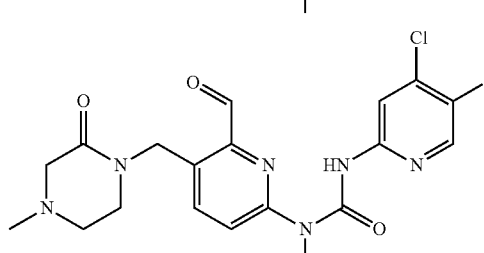
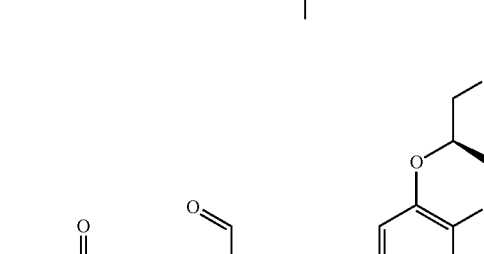
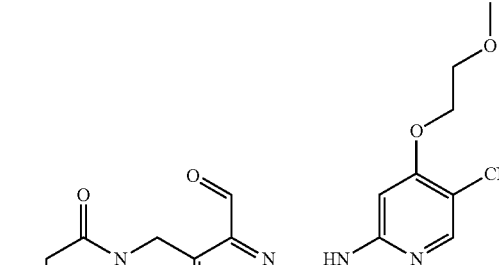

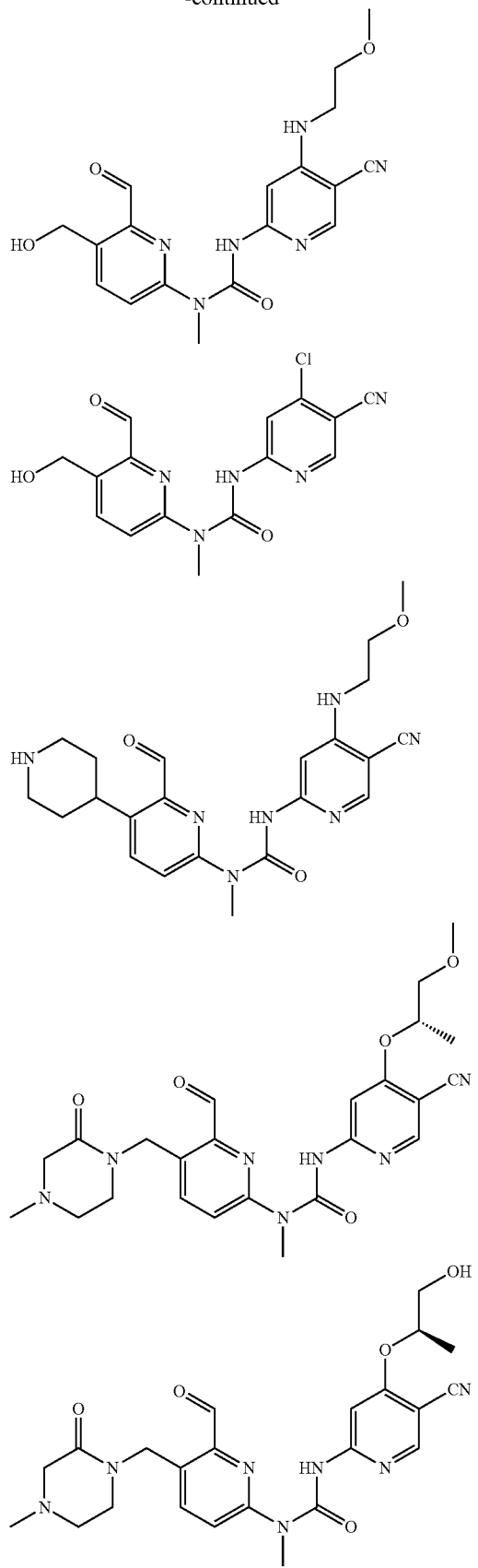

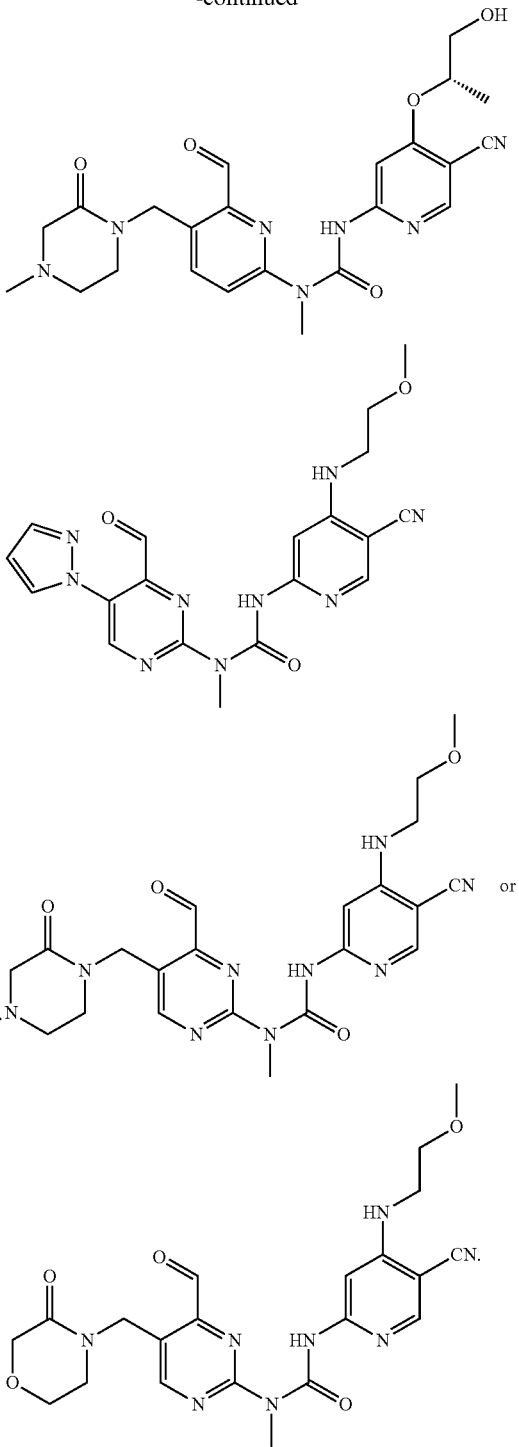

7. A pharmaceutical composition comprising the compound of claim 2 or the pharmaceutically acceptable salt thereof, and a pharmaceutically acceptable carrier, diluent, and/or excipient thereof.

8. A method for treating hepatocellular cancer, comprising administering a therapeutically effective amount of the compound of claim 2, or a pharmaceutically acceptable salt thereof, to a subject in need thereof.

* * * * *